(12) United States Patent
Ochsner et al.

(10) Patent No.: US 10,408,847 B2
(45) Date of Patent: Sep. 10, 2019

(54) TUBERCULOSIS BIOMARKERS AND USES THEREOF

(71) Applicant: SomaLogic, Inc., Boulder, CO (US)

(72) Inventors: Urs Ochsner, Boulder, CO (US); David G. Sterling, Boulder, CO (US); Nebojsa Janjic, Boulder, CO (US)

(73) Assignee: SomaLogic, Inc., Boulder, CO (US)

( * ) Notice: Subject to any disclaimer, the term of this patent is extended or adjusted under 35 U.S.C. 154(b) by 0 days.

(21) Appl. No.: 15/709,880

(22) Filed: Sep. 20, 2017

(65) Prior Publication Data

US 2018/0128839 A1 May 10, 2018

Related U.S. Application Data

(63) Continuation of application No. 14/968,276, filed on Dec. 14, 2015, now abandoned, which is a continuation of application No. 13/862,177, filed on Apr. 12, 2013, now abandoned.

(60) Provisional application No. 61/623,732, filed on Apr. 13, 2012.

(51) Int. Cl.
| | |
|---|---|
| *A61K 39/04* | (2006.01) |
| *A61K 39/02* | (2006.01) |
| *A61K 39/00* | (2006.01) |
| *G01N 33/68* | (2006.01) |
| *C12Q 1/6883* | (2018.01) |
| *G01N 33/569* | (2006.01) |
| *A61K 31/496* | (2006.01) |

(52) U.S. Cl.
CPC ....... *G01N 33/6893* (2013.01); *A61K 31/496* (2013.01); *C12Q 1/6883* (2013.01); *G01N 33/5695* (2013.01); *C12Q 2600/106* (2013.01); *C12Q 2600/158* (2013.01); *G01N 2570/00* (2013.01); *G01N 2800/52* (2013.01); *G01N 2800/60* (2013.01)

(58) Field of Classification Search
USPC .............. 424/130.1, 158.1, 184.1, 248.1
See application file for complete search history.

(56) References Cited

U.S. PATENT DOCUMENTS

| | | | |
|---|---|---|---|
| 2007/0015222 A1 | 1/2007 | Kaneko et al. | |
| 2009/0104602 A1 | 4/2009 | Fernandez-Reyes et al. | |
| 2010/0260771 A1* | 10/2010 | Dieplinger | G01N 33/6893 424/158.1 |
| 2011/0129817 A1 | 6/2011 | Banchereau et al. | |
| 2011/0196614 A1 | 8/2011 | Banchereau et al. | |
| 2011/0275794 A1 | 11/2011 | Rohloff et al. | |
| 2014/0155411 A1 | 6/2014 | Ochsner et al. | |

FOREIGN PATENT DOCUMENTS

| | | |
|---|---|---|
| JP | 2007-024631 | 2/2007 |
| JP | 2010-506144 | 2/2010 |
| JP | 2011-526152 | 10/2011 |
| WO | WO 2004/001070 | 12/2003 |
| WO | WO 2007/103770 | 9/2007 |
| WO | WO 2008/022177 | 2/2008 |
| WO | WO 2009/028880 | 3/2009 |
| WO | WO 2009/158521 | 12/2009 |
| WO | WO 2011/066008 | 6/2011 |
| WO | WO 2013/155460 | 10/2014 |

OTHER PUBLICATIONS

Blackberg et al. (1999) Pancreas 19(4):325-334 "Tissue Kallikrein in Severe Acute Pancreatitis in Patients Treated with High-Dose Intraperitoneal Aprotinin".

Agranoff et al. (Sep. 2006) "Identification of diagnostic markers for tuberculosis by proteomic fingerprinting of serum" Lancet 368:1012-1021.

Almeida et al.. (Jun. 2009) Transactions of the Royal Society of Tropical Medicine and Hygiene, Elsevier, GB, 103(6):575-580, "Alpha1-acid lycoprotein and alphal-antitrypsin as early markers of treatment response in patients receiving the intensive phase of tuberculosis therapy".

Aranday-Cortes et al. (2012) "Transcriptional profiling of disease-induced host responses in bovine tuberculosis and the identification of potential diagnostic biomarkers" PloS one 7(2): e30626.

Basaraba (2008) "Experimental tuberculosis: the role of comparative pathology in the discovery of improved tuberculosis treatment strategies" Tuberculosis 88:S35-S47.

Berry et al. (Aug. 2010) "An interferon-inducible neutrophil-driven blood transcriptional signature in human tuberculosis" Nature 466: 973-977.

Burman (2003) "The Hunt for the Elusive Surrogate Marker of Sterilizing Activity in Tuberculosis Treatment" American Journal of Respiratory and Critical Care Medicine 167:1299-1301.

Chakera et al. (2011) "Surrogate markers of infection: interrogation of the immune system" Biomarkers in Medicine 5(2):131-148.

(Continued)

*Primary Examiner* — Rodney P Swartz
(74) *Attorney, Agent, or Firm* — Adsero IP

(57) ABSTRACT

The present application includes biomarkers, methods, devices, reagents, systems, and kits for the detection, treatment and diagnosis of tuberculosis (TB). In one aspect, the present application includes the identification of biomarkers that can be used alone or in various combinations for the detection of TB, including those set forth in Tables 1, 2, 4, 5, and 8 to 12. In another aspect, the application provides biomarkers that can be used alone or in various combinations to diagnose or prognose TB or follow treatment response. In another aspect, methods are provided for diagnosing TB in an individual, where the methods include detecting, in a biological sample from an individual, at least one biomarker value corresponding to at least one biomarker selected from the group of biomarkers provided in Tables 1, 2, 4, 5, and 8 to 12, wherein the individual is classified as having TB, or the likelihood of the individual having TB is determined, based on the at least one biomarker value.

4 Claims, 32 Drawing Sheets

(56) References Cited

OTHER PUBLICATIONS

De la Paz Santangelo et al. (Nov. 2011) "Glycolytic and non-glycolytic functions of *Mycobacterium tuberculosis* fructose-1,6-bisphosphate aldolase, an essential enzyme produced by replicating and non-replicating bacilli" The Journal of Biological Chemistry 286(46):40219-40231.

Djoba Siawaya et al. (Apr. 2009) Clinical and Experimental Immunology 156(I):69-77, "Differential cytokine secretion and early treatment response in patients with pulmonary tuberculosis".

EP Partial Search Report issued in EP 13774934.7 dated Oct. 16, 2015.

EP Search Report issued in EP 13774934.7 dated Jan. 16, 2016.

Friedland et al. (2002) Differential regulation of MMP-1/9 and TIMP-1 secretion in human monocytic cells in response to *Mycobacterium tuberculosis* Matrix biology : Journal of the International Society for Matrix Biology 21:103-110.

Frolova et al. (Jun. 2012) "Thrombospondin-4 regulates fibrosis and remodeling of the myocardium in response to pressure overload" FASEB Journal : official publication of the Federation of American Societies for Experimental Biology; 26:2363-2373.

Gold et al. (Dec. 7, 2010) PLOS ONE, 5(12):el5004, "Aptamer-Based 1-8 Multiplexed Proteomic Technology for Biomarker Discovery".

International Preliminary Report on Patentability issued in PCT/US2013/36447 dated Oct. 14, 2014.

International Search Report and Written Opinion dated Aug. 6, 2013 in PCT/US2013/36447.

Jacobsen et al. (Feb. 2007) "Candidate biomarkers for discrimination between infection and disease caused by *Mycobacterium tuberculosis* ", J. Mol. Med. 85:613-621.

Juffermans et al. (Dec. 1998) "Serum concentrations of lipopolysaccharide activity-modulating proteins during tuberculosis" The Journal of Infectious Diseases 178:1839-1842.

Krishnan, Nitya et al., (Sep. 2007) "A transcriptomic 1-8 approach for studying the activation of dendritic cells in response to mycobacterial infections" Thesis UCL Eprints Retrieved from the Internet: URL:http://eprints.ucl.ac.uk/4929/*appendix VIII, p. 251, right-hand col (cited in EP Search Report issued in EP 13774934.7 dated Jan. 16, 2016).

Maertzdorf et al. (2012) "Common patterns and disease-related signatures in tuberculosis and sarcoidosis" Proceedings of the National Academy of Sciences of the United States of America, www.pnas.org/cgi/doi/10.1073/pnas.1121072109; pp. 1-6.

Marquis et al. (Jan. 2008) "Fibrotic response as a distinguishing feature of resistance and susceptibility to pulmonary infection with *Mycobacterium tuberculosis* in mice" Infection and Immunity 76:78-88.

McNerney and Daley (Mar. 2011) "Towards a point-of-care test for active tuberculosis: obstacles and opportunities", Nat Rev Microbiol 9(3):204-213.

Mistry et al. (Feb. 2007) "Gene-Expression Patterns in Whole Blood Identify Subjects at Risk for Recurrent Tuberculosis", The Journal of Infectious Diseases, 95:57-65.

Nahid et al. (2011) "CDC/NIH Workshop. Tuberculosis biomarker and surrogate endpoint research roadmap"Am J Respir Crit Care Med 184:972-979.

Nemeth et al. (2011) "Specific cytokine patterns of pulmonary tuberculosis in Central Africa", Clinical Immunology 138:50-59.

Pai et al. (2010) "New and improved tuberculosis diagnostics: evidence, policy, practice and impact", Curr Opin Pulm Med 16(3):271-284.

Qu and Lehrer (Jun. 1998) "Secretory phospholipase A2 is the principal bactericide for staphylococci and other gram-positive bacteria in human tears" Infection and Immunity 66: 2791-2797.

Rivera-Marrero et al. (2000) "Induction of MMP-9 mediated gelatinolytic activity in human monocytic cells by cell wall components of *Mycobacterium tuberculosis* " Microbial Pathogenesis 29:231-244.

Salgame (May 2011) "MMPs in tuberculosis: granuloma creators and tissue destroyers"The Journal of Clinical Investigation 121(5):1686-1688.

Sato et al. (Aug. 2003) "The fibrinolytic system in dissemination and matrix protein deposition during a *mycobacterium* infection" The American Journal of Pathology 163(2):517-531.

Schroder and Schumann (2005) "Non-LPS targets and actions of LPS binding protein (LBP)" Journal of Endotoxin Research 11(4):237-242.

Siawaya et al. (2009) Clinical and Experimental Immunology 156:69-77 "Differential cytokine secretion and early treatment response in patients with pulmonary tuberculosis".

Spigelman et al. (2010) "New initiative speeds tuberculosis drug development: novel drug regimens become possible in years, not decades", The International Journal of Tuberculosis and Lung Disease: The Official Journal of the International Union Against Tuberculosis and Lung Disease 14(6):663-664.

Tanaka et al. (2011) "Identification of tuberculosis-associated proteins in whole blood supernatant" BMC Infectious Diseases 11:71.

Wallis (2007) "Surrogate markers to assess new therapies for drug-resistant tuberculosis" Expert Rev Anti Infect Ther 5(2):163-168.

Wallis et al. (Mar. 2009) "Biomarkers for tuberculosis disease activity, cure, and relapse" The Lancet Infectious Diseases 9:162-172.

Walzl et al. (Aug. 2008) Journal of Infection 57(2):103-109, "Biomarkers for TB treatment response: Challenges and future strategies".

Weiner et al. (2012) "Biomarkers of inflammation, immunosuppression and stress with active disease are revealed by metabolomic profiling of tuberculosis patients" PloS one 7:e40221.

* cited by examiner

```
┌─────────────────────────────────────────────────────────┐
│ RETRIEVE ON A COMPUTER BIOMARKER INFORMATION FOR AN     │
│ INDIVIDUAL, WHEREIN THE BIOMARKER INFORMATION COMPRISES │
│ A BIOMARKER VALUE CORRESPONDING TO A BIOMARKER          │
│ SELECTED FROM THE BIOMARKERS LISTED IN TABLE 1          │
└─────────────────────────────────────────────────────────┘
                                                    └── 3204

┌──────────────────────────────┐
                    │ PERFORM WITH THE COMPUTER A  │
                    │ CLASSIFICATION OF THE BIOMARKER │
                    │           VALUE              │
                    └──────────────────────────────┘
                                                    └── 3208

┌──────────────────────────────────┐
                 │ INDICATE A LIKELIHOOD THAT THE   │
                 │ INDIVIDUAL HAS TUBURCULOSIS BASED│
                 │     UPON THE CLASSIFICATION      │
                 └──────────────────────────────────┘
                                                    └── 3212

S, Week 8 Slow-Responder
R, Week 8 Responder
A, All Baseline

TUBERCULOSIS BIOMARKERS AND USES THEREOF

RELATED APPLICATIONS

This application is a continuation of U.S. application Ser. No. 14/968,276, filed Dec. 14, 2015 (now abandoned), which is a continuation application of U.S. application Ser. No. 13/862,177, filed Apr. 12, 2013 (now abandoned). U.S. application Ser. No. 13/862,177 claims the benefit of U.S. Provisional Application Ser. No. 61/623,732, filed Apr. 13, 2012, each of which is incorporated herein by reference in its entirety.

FIELD OF THE INVENTION

The present invention relates generally to the identification and detection of biomarkers for Tuberculosis (TB). More specifically, the invention relates to one or more biomarkers, methods, devices, reagents, mathematical modeling, systems, and kits for the evaluation of TB infection and disease; wherein the evaluation may comprise diagnosis, prognosis, treatment, treatment response and treatment effects and treatment toxicity, determination of recurrence, reinfection, relapse or predicting reactivation from the latent infection to active disease of TB in an individual.

BACKGROUND

The following description provides a summary of information relevant to the present disclosure and is not an admission that any of the information provided or publications referenced herein is prior art to the present disclosure.

Tuberculosis (TB) causes 1.4 million deaths annually and is associated with substantial personal, social, public health, and economic costs, particularly in those individuals co-infected with HIV and other chronic diseases. Proper, accurate, and timely diagnosis of TB is essential to rapidly identify patients for treatment and targeted public health intervention to prevent spread of disease and minimize the emergence of drug resistant strains. Worldwide, most cases of TB are diagnosed using a sputum smear, clinical symptoms, and/or radiographs. There is a clear imperative for improved diagnostics, because the current diagnosis of mycobacterial disease by microscopic stain for acid-fast bacilli (AFB, e.g. Ziehl-Neelsen method) in sputum fails to detect mycobacteria in approximately 50% of cases of TB. This method of diagnosis performs poorly in HIV co-infected individuals and is particularly problematic when an individual is unable to produce a specimen (e.g. an infant unable to produce sputum) or has disease outside of the lung (extrapulmonary). According to the World Health Organization (WHO) estimates, the global case detection rate is just 63%, and only half of the TB cases in Africa are detected and notified (McNerney and Daley (2011) Nat Rev Microbiol 9(3):204-213). The under-diagnosis of TB is critically important in AIDS due to the high mortality associated with TB-HIV co-infection. Diagnosing TB in HIV negative patients with contagious disease is a priority intervention to continue progress in decreasing the worldwide TB incidence. An estimated 400,000 people died of HIV-related TB in 2009, which makes TB responsible for one in four AIDS deaths.

Undiagnosed patients are a major reservoir for spread of disease including drug resistant TB. Microbiological techniques required for specific identification and drug susceptibility can take days to weeks and are often not available in resource poor and remote areas. A rapid, accurate, and inexpensive TB test used by personnel in the clinic or local hospital would add tremendous value to public health in areas with limited resources by identifying those in need of treatment rapidly and hence decrease the spread of disease to others. The lack of a point-of-care (POC) test has been identified as a major gap in the existing pipeline of TB diagnostics (Pal et al. (2010) Curr Opin Pulm Med 16(3): 271-284).

Clinical response to treatment for tuberculosis is manifest by improvement in constitutional symptoms, decreased microbial burden, lessening risk of spread to others and fairly rapid return to well-being in patients treated with multiple drug therapy, but predicting who will ultimately relapse requires long-term clinical follow up. With new regimens that may significantly shorten TB treatment duration, more rapid surrogate markers for sterilizing regimens are needed. (Spigelman et al. (2010) The international journal of tuberculosis and lung disease: the official journal of the International Union against Tuberculosis and Lung Disease 14:663-664; Wallis et al. (2009) The Lancet infectious diseases 9:162-172). There is no perfect surrogate endpoint of cure (defined as the absence of relapse after 1 to 2 years of close clinical follow-up); however, the 8-week sputum culture status is the most widely accepted endpoint (Chakera et al. (2011) Biomarkers in medicine 5:131-148; Nemeth et al. (2011) Clinical immunology 138:50-59; Wallis et al. (2009) The Lancet infectious diseases 9:162-172).

The discovery of robust protein biomarkers for treatment response that could be used earlier in treatment assessments is expected to have implications for clinical trials and potentially be helpful for clinical care of patients. Due to the rarity of relapses (<5% of patients relapse in studies of drug susceptible disease using standard therapy) large sample sizes need to be included in clinical trials, typically 75-300 subjects per arm or comparison group. It has been suggested that in TB trials serial measurement of surrogate markers such as multiple serum proteins with large dynamic range could reduce patient sample sizes by 50-90% and decrease the time and monetary investment in desperately needed human trials. (Burman (2003) American journal of respiratory and critical care medicine 167:1299-1301; Nahid et al. (2011) American journal of respiratory and critical care medicine 184 (8):972-979e). Accordingly, a need exists for biomarkers, methods, devices, reagents, systems, and kits that enable the diagnosis, prognosis, treatment response markers and determination of recurrence or prediction of reactivation of TB.

Biomarker selection for a specific disease state involves first the identification of markers that have a measurable and statistically significant difference in a disease population compared to a control population for a specific medical application. Biomarkers can include secreted or shed molecules that parallel disease development or progression and readily diffuse into the blood stream or other body fluids from TB tissue or from surrounding tissues and circulating cells in response to a TB. The biomarker or set of biomarkers identified are generally clinically validated or shown to be a reliable indicator for the original intended use for which it was selected. Biomarkers can include small molecules, peptides, proteins, and nucleic acids. Some of the key issues that affect the identification of biomarkers include overfitting of the available data and bias in the data.

A variety of methods have been used in an attempt to identify biomarkers for evaluation, diagnosis, prognosis and determination of recurrence or reactivation of disease. For protein-based markers, these include two-dimensional electrophoresis, mass spectrometry, and immunoassay methods. For nucleic acid markers, these include mRNA expression profiles, microRNA profiles, fluorescence in situ hybridization (FISH), serial analysis of gene expression (SAGE), methylation profiles, and large-scale gene expression arrays.

The utility of two-dimensional electrophoresis is limited by low detection sensitivity; issues regarding protein solubility, charge, and hydrophobicity; gel reproducibility; and the possibility of a single spot representing multiple proteins. For mass spectrometry, depending on the format used, limitations revolve around the sample processing and separation, sensitivity to low abundance proteins, signal to noise considerations, and inability to immediately identify the detected protein, lipid or small molecule. Limitations in immunoassay approaches to biomarker discovery are centered on the inability of antibody-based multiplex assays to measure a large number of analytes. One might simply print an array of antibodies and, without sandwiches, measure the analytes bound to those antibodies. This would be the formal equivalent of using a whole genome of nucleic acid sequences to measure by hybridization all DNA or RNA sequences in an organism or a cell. The hybridization experiment works because hybridization can be a stringent test for identity. Even high-affinity antibodies are not stringent enough in selecting their binding partners to work in the context of blood or even cell extracts because the protein ensemble in those matrices have extremely different abundances. Thus, one must use a different approach with immunoassay-based approaches to biomarker discovery—one would need to use multiplexed ELISA assays (that is, sandwiches) to get sufficient stringency to measure many analytes simultaneously to decide which analytes are indeed biomarkers. Sandwich immunoassays do not scale to high content, and thus biomarker discovery using stringent sandwich immunoassays is not possible using standard array formats. Lastly, antibody reagents are subject to substantial lot variability and reagent instability. The instant platform for protein biomarker discovery overcomes these problems.

Many of these methods rely on or require some type of sample fractionation prior to the analysis. Thus the sample preparation required to run a sufficiently powered study designed to identify and discover statistically relevant biomarkers in a series of well-defined sample populations is extremely difficult, costly, and time consuming. During fractionation, a wide range of variability can be introduced into the various samples. For example, a potential marker could be unstable to the process, the concentration of the marker could be changed, inappropriate aggregation or disaggregation could occur, and inadvertent sample 'contamination could occur and thus obscure the subtle changes anticipated in early disease.

It is widely accepted that biomarker discovery and detection methods using these technologies have serious limitations for the identification of diagnostic biomarkers. These limitations include an inability to detect low-abundance biomarkers, an inability to consistently cover the entire dynamic range of the proteome, irreproducibility in sample processing and fractionation, and overall irreproducibility and lack of robustness of the method. Further, these methods have introduced biases into the data and not adequately addressed the complexity of the sample populations, including appropriate controls, in terms of the distribution and randomization required to identify and validate biomarkers within a target disease population.

Although efforts aimed at the discovery of new and effective TB biomarkers have gone on for several decades, the efforts have been largely unsuccessful. Biomarkers for various diseases typically have been identified in academic laboratories, usually through an accidental discovery while doing basic research on some disease process. Based on the discovery and with small amounts of clinical data, papers were published that suggested the identification of a new biomarker. Most of these proposed biomarkers, however, have not been confirmed as real or useful biomarkers, primarily because the small number of clinical samples tested, and have provided only weak statistical proof that an effective biomarker has in fact been found. That is, the initial identification was not rigorous with respect to the basic elements of statistics. In each of the years 1994 through 2003, a search of the scientific literature shows that thousands of references directed to biomarkers were published. During that same timeframe, however, the FDA approved for diagnostic use, at most, three new protein biomarkers in a year, and in several years, no new protein biomarkers were approved.

Based on the history of failed biomarker discovery efforts, mathematical theories have been proposed that further promote the general understanding that biomarkers for disease are rare and difficult to find. Biomarker research based on 2D gels or mass spectrometry supports these notions. Very few useful biomarkers have been identified through these approaches. However, it is usually overlooked that 2D gel and mass spectrometry measure proteins that are present in blood at approximately 1 nM concentrations and higher, and that this ensemble of proteins may well be the least likely to change with disease. Other than the instant biomarker discovery platform, proteomic biomarker discovery platforms that are able to accurately measure protein expression levels at much lower concentrations do not exist.

Much is known about biochemical pathways for complex human biology. Many biochemical pathways culminate in or are started by secreted proteins that work locally within the pathology, for example, growth factors are secreted to stimulate the replication of other cells in the pathology, and other factors are secreted to ward off the immune system, and so on. While many of these secreted proteins work in a paracrine fashion, some operate distally in the body. One skilled in the art with a basic understanding of biochemical pathways would understand that many pathology-specific proteins ought to exist in blood at concentrations below (even far below) the detection limits of 2D gels and mass spectrometry. What must precede the identification of this relatively abundant number of disease biomarkers is a proteomic platform that can analyze proteins at concentrations below those detectable by 2D gels or mass spectrometry.

SUMMARY

The present disclosure includes biomarkers, methods, reagents, devices, systems, mathematical modeling and kits for the evaluation of TB and subsequent TB treatment responses. The biomarkers of the present disclosure were identified using a multiplex aptamer-based assay, which is described in Example 1. By using the aptamer-based biomarker identification method described herein, this application describes a surprisingly large number of TB biomarkers that are useful for the evaluation and treatment of TB. In identifying these biomarkers, approximately 1030 proteins from individual participant samples were measured, some of which were at concentrations in the low femtomolar range. This is about four orders of magnitude lower than biomarker discovery experiments done with 2D gels or mass spectrometry.

While certain of the described TB biomarkers may be useful alone for detecting host responses to TB treatment and diagnosing TB, methods are described herein for the grouping of multiple subsets of the TB biomarkers that are useful as a panel of biomarkers to diagnose TB, detect sub-clinical or overt drug toxicity and predict successful response to therapy. Once an individual biomarker or subset of biomarkers is identified, the detection or diagnosis of TB and following TB treatment and response to treatment can be accomplished using any assay platform or format that is capable of measuring differences in the levels of the selected biomarker or biomarkers in a biological sample.

However, it was only by using the multiplex aptamer-based biomarker identification method described herein, wherein about 1030 separate potential biomarker values were individually screened from individuals diagnosed with TB and monitoring biomarkers that change with treatment that it was possible to identify the TB biomarkers disclosed herein. This discovery approach is in stark contrast to biomarker discovery using animal models or in vitro systems as it queries a more patient-relevant system and measures proteins and not RNA expression (Berry (August 2010) Nature 466, doi:10.1038/nature09247); an interferon-inducible neutrophil-driven blood transcriptional signature in human tuberculosis.

Thus, in one aspect of the instant application, one or more biomarkers are provided for use either alone or in various combinations to diagnose and treat TB. Exemplary embodiments include the biomarkers provided in Tables 1, 2, 4, 5 and 8 to 12, which as noted above were identified using a multiplex aptamer-based assay, as described in Examples 1 and 2. The markers could also be reflective of the effect of treatment agents on biomarkers and could prove to be markers of treatment toxicity or effects.

While certain of the described TB biomarkers are useful alone the evaluation of TB, methods are also described herein for the grouping of multiple subsets of the TB biomarkers that are each useful as a panel of two or more biomarkers. Thus, various embodiments of the instant application provide combinations comprising N biomarkers, wherein N is at least two; wherein N is at least 3; wherein N is at least 4; wherein N is at least 5; wherein N is at least 6; wherein N is at least 7; wherein N is at least 8; wherein N is at least 9; wherein N is at least 10; and so on; wherein N can be any number from 1 biomarker to 239 biomarkers.

As used herein, evaluation of TB refers to evaluating whether an individual has a first evaluation of no evidence of disease (NED) when at least one biomarker of one or more of Tables 1, 2, 4, 5 or 8 to 12 is not detected as differentially expressed from the control distribution, or has a second evaluation of evidence of disease (EVD) when at least one biomarker of one or more of Tables 1, 2, 4, 5 or 8 to 12 is detected as differentially expressed from the control distribution.

In another aspect, a method is provided for evaluating an individual for TB, wherein the method comprises diagnosing the individual as having or not having TB, prognosing a future course of the TB and its treatment, determining recurrence or predicting reactivation of TB in an individual who had been apparently cured of the active TB, has only the latent form of the disease and characterizing the response of the person to treatment of TB, or any combination thereof.

In another embodiment, the method of evaluating an individual for TB comprises diagnosing an individual by determining a detectable value corresponding to a biomarker of one or more of Tables 1, 2, 4, 5 or 8 to 12 in a biological sample of the individual, wherein the diagnosing comprises a first diagnosis of no evidence of disease (NED) and no TB when there is substantially no differential expression of the biomarker value of the individual relative to a biomarker value of the control population; or a second diagnosis of evidence of disease (EVD) and TB when there is differential expression of the biomarker value of the individual relative to the biomarker value of the control population. As noted above, various embodiments provide combinations comprising N biomarkers, wherein N is at least two; wherein N is at least 3; wherein N is at least 4; wherein N is at least 5; wherein N is at least 6; wherein N is at least 7; wherein N is at least 8; wherein N is at least 9; wherein N is at least 10; and so on; wherein N can be any number from 1 biomarker to 239 biomarkers.

In one aspect, the method of diagnosing comprises assaying a biological sample of an individual to determine a biomarker value corresponding to at least one biomarker of one or more of Tables 1, 2, 4, 5 or 8 to 12, comparing the biomarker value of the individual to a biomarker value of a control population to determine whether there is a differential expression; and classifying the individual as having the first diagnosis where there no differential expression relative to the control population, or with the second diagnosis where there is a differential expression relative to the control population. Various embodiments provide combinations comprising N biomarkers, wherein N is at least two; wherein N is at least 3; wherein N is at least 4; wherein N is at least 5; wherein N is at least 6; wherein N is at least 7; wherein N is at least 8; wherein N is at least 9; wherein N is at least 10; and so on; wherein N can be any number from 1 biomarker to 239 biomarkers.

In another aspect, the evaluating of TB comprises prognosing a first prognosis of no evidence of disease (NED) and a favorable prognosis, or a second prognosis of evidence of disease (EVD) and an unfavorable prognosis.

In one aspect, the prognosing method comprises assaying a biological sample of an individual to determine a biomarker value corresponding to at least one biomarker of one or more of Tables 1, 2, 4, 5 or 8 to 12, comparing the biomarker value of the individual to a biomarker value of a control population to determine if there is a differential expression; and classifying the individual as having the first prognosis for a negative TB diagnosis when there is no differential expression, or the second prognosis for a positive TB diagnosis when there is differential expression. In various embodiments, combinations comprising N biomarkers are provided, wherein N is at least two; wherein N is at least 3; wherein N is at least 4; wherein N is at least 5; wherein N is at least 6; wherein N is at least 7; wherein N is at least 8; wherein N is at least 9; wherein N is at least 10; and so on; wherein N can be any number from 1 biomarker to 239 biomarkers.

In one aspect, a method of evaluating response to treatment is provided that comprises: assaying a biological sample of an individual being treated to determine a value corresponding to at least one biomarker from one or more of Tables 8 to 12; comparing the biomarker value of the individual to a biomarker value of a control population to determine the extent of differential expression; and correlating the extent of differential expression of said biomarker value with an increased likelihood of positive response to treatment. In various embodiments, combinations comprising N biomarkers are provided, wherein N is at least two; wherein N is at least 3; wherein N is at least 4; wherein N is at least 5; wherein N is at least 6; wherein N is at least 7; wherein N is at least 8; wherein N is at least 9; wherein N is at least 10; and so on; wherein N can be any number from 1 biomarker to 122 biomarkers.

In another aspect, a method of evaluating response to treatment is provided that comprises assaying a biological sample of an individual being treated to determine a value corresponding to at least one biomarker from one or more of Tables 8 to 12; initiating treatment comprising antimicrobial therapies directed at the tubercle bacillus; and comparing the biomarker value before treatment with the biomarker value after some period of treatment, whereby a change in the biomarker value is indicative of response to treatment. In various embodiments, combinations comprising N biomarkers are provided, wherein N is at least two; wherein N is at least 3; wherein N is at least 4; wherein N is at least 5; wherein N is at least 6; wherein N is at least 7; wherein N is at least 8; wherein N is at least 9; wherein N is at least 10; and so on; wherein N can be any number from 1 biomarker to 122 biomarkers.

In another aspect, a method of evaluating is provided that comprises: determining the recurrence or reactivation of TB in an individual who had apparently been cured of active TB or had latent form of infection, wherein the determining of recurrence or reactivation comprises a first determination of no evidence of disease (NED) or a second determination of evidence of disease (EVD). The first determination of NED indicates no recurrence or reactivation of TB, and the second determination of EVD indicates treatment failure, recurrence or reactivation of the TB.

One method of determining recurrence or reactivation comprises: assaying a biological sample of an individual to determine a value corresponding to an at least one biomarker selected from one or more of Tables 1, 2, 4, 5 or 8 to 12; comparing the biomarker value of the individual to a biomarker value of a control population to determine if there is differential expression; and classifying the individual as having said first determination of no TB recurrence or reactivation when there is no differential expression relative to the control population, or said second determination of TB recurrence or reactivation when there is differential expression relative to the control value. In various embodiments, combinations comprising N biomarkers are provided, wherein N is at least two; wherein N is at least 3; wherein N is at least 4; wherein N is at least 5; wherein N is at least 6; wherein N is at least 7; wherein N is at least 8; wherein N is at least 9; wherein N is at least 10; and so on; wherein N can be any number from 1 biomarker to 239 biomarkers.

In another aspect, a method for treating tuberculosis infection in an individual is provided, comprising: diagnosing tuberculosis infection by causing to be determined a value corresponding to at least one biomarker selected from one or more of Tables 1, 2, 4, 5 or 8 to 12 in a biological sample of the individual, wherein said determination comprises comparing the biomarker value of the individual to the biomarker value in a control population for differential expression of the biomarker, wherein differential expression of the biomarker indicates the presence of tuberculosis infection in the individual; and administering treatment for tuberculosis infection to the individual thereby diagnosed with tuberculosis infection. In various embodiments, combinations comprising N biomarkers are provided, wherein N is at least two; wherein N is at least 3; wherein N is at least 4; wherein N is at least 5; wherein N is at least 6; wherein N is at least 7; wherein N is at least 8; wherein N is at least 9; wherein N is at least 10; and so on; wherein N can be any number from 1 biomarker to 239 biomarkers.

In yet another aspect, an assay for diagnosing tuberculosis infection in an individual, comprising: causing to be determined a value corresponding to at least one biomarker selected from one or more of Tables 1, 2, 4, 5 or 8 to 12 in a biological sample of the individual, wherein said determining comprises comparing the biomarker value of the individual to the biomarker value in a control population for differential expression of the biomarker, wherein differential expression of the biomarker indicates the presence of tuberculosis infection in the individual; and diagnosing an individual to have tuberculosis infection based on said differential expression of the biomarker. In various embodiments, combinations comprising N biomarkers are provided, wherein N is at least two; wherein N is at least 3; wherein N is at least 4; wherein N is at least 5; wherein N is at least 6; wherein N is at least 7; wherein N is at least 8; wherein N is at least 9; wherein N is at least 10; and so on; wherein N can be any number from 1 biomarker to 239 biomarkers.

In another embodiment, a method for diagnosing that an individual does or does not have tuberculosis is provided, the method comprising: contacting a biological sample from an individual with at least N aptamers wherein each aptamer has specific affinity for a biomarker corresponding to one of N biomarkers selected from one or more of Tables 1, 2, 4, 5 or 8 to 12; detecting the levels of the biomarkers, in the biological sample; and determining a biomarker value for each of said N biomarkers, wherein said individual is diagnosed as having or not having tuberculosis based on said biomarker values, and wherein N is any integer from 2 to 239.

In one embodiment, at least one biomarker is selected from Table 1 and/or Table 4 and/or Table 5. In one embodiment, at least two biomarkers are selected from Table 1 and/or Table 4 and/or Table 5. In one embodiment, at least three biomarkers are selected from Table 1 and/or Table 4 and/or Table 5. In one embodiment, at least four biomarkers are selected from Table 1 and/or Table 4 and/or Table 5. In one embodiment, at least five biomarkers are selected from Table 1 and/or Table 4 and/or Table 5. In one embodiment, at least six biomarkers are selected from Table 1 and/or Table 4 and/or Table 5. In one embodiment, at least seven biomarkers are selected from Table 1 and/or Table 4 and/or Table 5. In one embodiment, at least eight biomarkers are selected from Table 1 and/or Table 4 and/or Table 5. In one embodiment, at least nine biomarkers are selected from Table 1 and/or Table 4 and/or Table 5. In one embodiment, at least ten biomarkers are selected from Table 1 and/or Table 4 and/or Table 5, etc.

In one embodiment, at least one biomarker is selected from the group consisting of TSP4, TIMP-2, SEPR, MRC-2, Antithrombin III, SAA, CRP, NPS-PLA2, LEAP-1, and LBP. In one embodiment, at least two biomarkers are selected from the group consisting of TSP4, TIMP-2, SEPR, MRC-2, Antithrombin III, SAA, CRP, NPS-PLA2, LEAP-1, and LBP. In one embodiment, at least three biomarkers are selected from the group consisting of TSP4, TIMP-2, SEPR, MRC-2, Antithrombin III, SAA, CRP, NPS-PLA2, LEAP-1, and LBP. In one embodiment, at least four biomarkers are selected from the group consisting of TSP4, TIMP-2, SEPR, MRC-2, Antithrombin III, SAA, CRP, NPS-PLA2, LEAP-1, and LBP. In yet another embodiment, at least five biomarkers are selected from the group consisting of TSP4, TIMP-2, SEPR, MRC-2, Antithrombin III, SAA, CRP, NPS-PLA2, LEAP-1, and LBP, etc.

In one embodiment N is any integer from 3 to 239 or from 4 to 239 or from 5 to 239 or from 6 to 239 or from 7 to 239 or from 8 to 239 or from 9 to 239 or from 10 to 239 or from 15 to 239 or from 20 to 239, etc.

In another aspect, a method for determining whether treatment for tuberculosis infection should be administered to a patient is provided, comprising: a) causing an assay to be conducted for determining a biomarker value corresponding to at least one biomarker of 1, 2, 4 or 5 and Tables 8 to 12 in a biological sample of the individual, wherein said determining comprises comparing the biomarker value of the individual to the biomarker value in a control population for differential expression of the biomarker, wherein differential expression of the biomarker indicates the presence of tuberculosis infection in the individual; b) diagnosing an individual to have tuberculosis infection based on said differential expression of the biomarker; and c) administering treatment for tuberculosis infection. In one embodiment, at least one biomarker is selected from Table 1 and/or Table 4 and/or Table 5 and/or Table 9 and/or Table 10 and/or Table 11 and/or Table 12. In one embodiment, at least one biomarker is selected from the group consisting of TSP4, TIMP-2, SEPR, MRC-2, Antithrombin III, SAA, CRP, NPS-PLA2, LEAP-1, LBP, Coagulation factor V, XPNPEP1, PSME1, IL-11 Ra, HSP70, Galectin-8, a2-Antiplasmin, ECM1, YES, IGFBP-1, CATZ, BGN, LYNB, and IL-7.

In another embodiment, a method for determining whether treatment for tuberculosis should be administered is provided, the method comprising: a) contacting a biological sample from an individual with at least N aptamers wherein each aptamer has specific affinity for a biomarker corresponding to one of N biomarkers selected from Table 1, 2, 4, 5 or Tables 8 to 12; b) detecting the levels of the biomarkers, in the biological sample; and determining a biomarker value for each of said N biomarkers, c) diagnosing an individual to have tuberculosis infection based on said biomarker values, and administering treatment for tuberculosis infection; wherein N is any integer from 2 to 239.

In one embodiment, at least one biomarker is selected from Table 1 and/or Table 4 and/or Table 5 and/or Table 9 and/or Table 10 and/or Table 11 and/or Table 12. In one embodiment, at least one biomarker is selected from the group consisting of TSP4, TIMP-2, SEPR, MRC-2, Antithrombin III, SAA, CRP, NPS-PLA2, LEAP-1, LBP, Coagulation factor V, XPNPEP1, PSME1, IL-11 Ra, HSP70, Galectin-8, a2-Antiplasmin, ECM1, YES, IGFBP-1, CATZ, BGN, LYNB, and IL-7.

In one embodiment N is any integer from 3 to 239 or from 4 to 239 or from 5 to 239 or from 6 to 239 or from 7 to 239 or from 8 to 239 or from 9 to 239 or from 10 to 239 or from 15 to 239 or from 20 to 239 etc.

In another aspect, a method for evaluating the drug toxicity resulting from the administration of drugs for the treatment of tuberculosis in and individual is provided comprising: a) administering treatment for tuberculosis infection to the individual, wherein a value corresponding to at least one biomarker of one or more of Tables 1, 2, 4, 5 or 8 to 12 in a biological sample of the individual has been determined; and b) evaluating the toxicity of the drug used in treatment by comparing said biomarker value(s) subsequent to treatment.

In another aspect, a method for evaluating the effectiveness of treatment for tuberculosis in and individual is provided comprising: a) administering treatment for tuberculosis infection to the individual, wherein a value corresponding to at least one biomarker of Tables 8 to 12 in a biological sample of the individual has been determined; and b) evaluating the effectiveness of treatment by comparing said biomarker value(s) subsequent to treatment. In another aspect, at least one of said biomarkers is selected from Table 9 and/or Table 10 and/or Table 11 and/or Table 12. In another aspect, at least two of said biomarkers are selected from Table 9 and/or Table 10 and/or Table 11 and/or Table 12. In another aspect, at least three of said biomarkers are selected from Table 9 and/or Table 10 and/or Table 11 and/or Table 12. In another aspect, at least four of said biomarkers are selected from Table 9 and/or Table 10 and/or Table 11 and/or Table 12. In another aspect, at least five of said biomarkers are selected from Table 9 and/or Table 10 and/or Table 11 and/or Table 12, etc.

In yet another, aspect at least one biomarker is selected from the group consisting of Coagulation factor V, XPNPEP1, PSME1, IL-11 Ra, HSP70, Galectin-8, a2-Antiplasmin, SAA, ECM1, YES, IGFBP-1, CATZ, BGN, LYNB and IL-7. In yet another aspect, at least two biomarkers are selected from the group consisting of Coagulation factor V, XPNPEP1, PSME1, IL-11 Ra, HSP70, Galectin-8, a2-Antiplasmin, SAA, ECM1, YES, IGFBP-1, CATZ, BGN, LYNB and IL-7. In yet another, aspect at least three biomarkers are selected from the group consisting of Coagulation factor V, XPNPEP1, PSME1, IL-11 Ra, HSP70, Galectin-8, a2-Antiplasmin, SAA, ECM1, YES, IGFBP-1, CATZ, BGN, LYNB and IL-7. In yet another aspect, at least four biomarkers are selected from the group consisting of Coagulation factor V, XPNPEP1, PSME1, IL-11 Ra, HSP70, Galectin-8, a2-Antiplasmin, SAA, ECM1, YES, IGFBP-1, CATZ, BGN, LYNB and IL-7. In yet another, aspect at least five biomarkers are selected from the group consisting of Coagulation factor V, XPNPEP1, PSME1, IL-11 Ra, HSP70, Galectin-8, a2-Antiplasmin, SAA, ECM1, YES, IGFBP-1, CATZ, BGN, LYNB and IL-7, etc.

In another embodiment, a method for evaluating the effectiveness of treatment for tuberculosis is provided comprising: a) contacting a biological sample from an individual with at least N aptamers wherein each aptamer has specific affinity for a biomarker corresponding to one of N biomarkers selected from Tables 8 to 12; b) detecting the levels of the biomarkers, in the biological sample; and determining a biomarker value for each of said N biomarkers; c) diagnosing an individual to have tuberculosis infection based on said biomarker values; d) administering treatment for tuberculosis infection; wherein N is any integer from 2 to 23; and e) evaluating the effectiveness of treatment by comparing said biomarker value(s) subsequent to treatment.

In another aspect, at least two of said biomarkers are selected from Table 9 and/or Table 10 and/or Table 11 and/or Table 12. In another aspect, at least three of said biomarkers are selected from Table 9 and/or Table 10 and/or Table 11 and/or Table 12. In another aspect, at least four of said biomarkers are selected from Table 9 and/or Table 10 and/or Table 11 and/or Table 12. In another aspect, at least five of said biomarkers are selected from Table 9 and/or Table 10 and/or Table 11 and/or Table 12, etc.

In yet another, aspect, at least one biomarker is selected from the group consisting of Coagulation factor V, XPNPEP1, PSME1, IL-11 Ra, HSP70, Galectin-8, a2-Antiplasmin, SAA, ECM1, YES, IGFBP-1, CATZ, BGN, LYNB and IL-7. In yet another aspect, at least two biomarkers are selected from the group consisting of Coagulation factor V, XPNPEP1, PSME1, IL-11 Ra, HSP70, Galectin-8, a2-Antiplasmin, SAA, ECM1, YES, IGFBP-1, CATZ, BGN, LYNB and IL-7. In yet another, aspect at least three biomarkers are selected from the group consisting of Coagulation factor V, XPNPEP1, PSME1, IL-11 Ra, HSP70, Galectin-8, a2-Antiplasmin, SAA, ECM1, YES, IGFBP-1, CATZ, BGN, LYNB and IL-7. In yet another aspect, at least four biomarkers are selected from the group consisting of Coagulation factor V, XPNPEP1, PSME1, IL-11 Ra, HSP70, Galectin-8, a2-Antiplasmin, SAA, ECM1, YES, IGFBP-1, CATZ, BGN, LYNB and IL-7. In yet another aspect, at least five biomarkers are selected from the group consisting of Coagulation factor V, XPNPEP1, PSME1, IL-11 Ra, HSP70, Galectin-8, a2-Antiplasmin, SAA, ECM1, YES, IGFBP-1, CATZ, BGN, LYNB and IL-7, etc.

In one embodiment N is any integer from 3 to 239 or from 4 to 239 or from 5 to 239 or from 6 to 239 or from 7 to 239 or from 8 to 239 or from 9 to 239 or from 10 to 239 or from 15 to 239 or from 20 to 239, etc.

In another aspect, a method for treating recurrence or reactivation of tuberculosis infection in an individual is provided, said method comprising: diagnosing recurrence or reactivation of tuberculosis infection by causing to be determined a biomarker value corresponding to a biomarker of Tables 1, 2, 4, 5 or 8 to 12 in a biological sample of the individual, wherein said determination comprises comparing the biomarker value of the individual to the biomarker value in a control population for differential expression of the biomarker, wherein differential expression of the biomarker indicates the recurrence or reactivation of tuberculosis infection in the individual; and administering treatment for recurrence or reactivation of tuberculosis infection to the individual thereby diagnosed with recurrent or reactivated tuberculosis infection.

In one embodiment, at least one biomarker is selected from Table 1 and/or Table 4 and/or Table 5 and/or Table 9 and/or Table 10 and/or Table 11 and/or Table 12. In one embodiment, at least one biomarker is selected from the group consisting of TSP4, TIMP-2, SEPR, MRC-2, Antithrombin III, SAA, CRP, NPS-PLA2, LEAP-1, LBP, Coagulation factor V, XPNPEP1, PSME1, IL-11 Ra, HSP70, Galectin-8, a2-Antiplasmin, ECM1, YES, IGFBP-1, CATZ, BGN, LYNB, and IL-7.

In one embodiment N is any integer from 3 to 239 or from 4 to 239 or from 5 to 239 or from 6 to 239 or from 7 to 239 or from 8 to 239 or from 9 to 239 or from 10 to 239 or from 15 to 239 or from 20 to 239 etc.

In yet another aspect, a method is provided for modifying treatment of tuberculosis infection in an individual, comprising: evaluating the status of tuberculosis infection by causing to be determined a biomarker value corresponding to a biomarker of Tables 1, 2, 4, 5 or 8 to 12 in a biological sample of the individual, wherein said evaluation comprises comparing the biomarker value of the individual to the biomarker value in a control population for differential expression of the biomarker, wherein differential expression of the biomarker indicates the need to intensify treatment of tuberculosis infection in the individual, and intensifying treatment for tuberculosis infection to the individual thereby evaluated as in need of intensified treatment of tuberculosis infection.

In one embodiment, at least one biomarker is selected from Table 1 and/or Table 4 and/or Table 5 and/or Table 9 and/or Table 10 and/or Table 11 and/or Table 12. In one embodiment, at least two biomarkers are selected from Table 1 and/or Table 4 and/or Table 5 and/or Table 9 and/or Table 10 and/or Table 11 and/or Table 12, etc. In one embodiment, at least one biomarker is selected from the group consisting of TSP4, TIMP-2, SEPR, MRC-2, Antithrombin III, SAA, CRP, NPS-PLA2, LEAP-1, LBP, Coagulation factor V, XPNPEP1, PSME1, IL-11 Ra, HSP70, Galectin-8, a2-Antiplasmin, ECM1, YES, IGFBP-1, CATZ, BGN, LYNB and IL-7. In one embodiment, at least two biomarkers are selected from the group consisting of TSP4, TIMP-2, SEPR, MRC-2, Antithrombin III, SAA, CRP, NPS-PLA2, LEAP-1, LBP, Coagulation factor V, XPNPEP1, PSME1, IL-11 Ra, HSP70, Galectin-8, a2-Antiplasmin, ECM1, YES, IGFBP-1, CATZ, BGN, LYNB and IL-7, etc.

In another aspect, a computer-implemented method is provided for classifying an individual as either having a first evaluation of NED, or as having a second evaluation of EVD. The method comprises: a) retrieving on a computer biomarker information for an individual, wherein the biomarker information comprises a biomarker value that corresponds to the at least one biomarker of Tables 1, 2, 4, 5 or 8 to 12; b) comparing said biomarker value of step a) to a biomarker value of a control population to determine if there is differential expression, and c) classifying the individual as having a first evaluation of NED when there is no differential expression of the biomarker value of the individual relative to the control population, or as having a second evaluation of EVD when there is differential expression of the biomarker value of the individual relative to the control population.

In the computer-implemented method, the evaluation can comprise a diagnosis, treatment, prognosis, determination of recurrence or reactivation of TB, and/or a combination thereof. The evaluation of NED can be indicative of a diagnosis of no TB, a prognosis of an outcome of no TB at a selected future time point, a determination of no recurrence or reactivation of TB, and/or a combination thereof. The evaluation of EVD can be indicative of a diagnosis of the presence of TB, a prognosis of an outcome of TB at a selected future time point, a determination of recurrence or reactivation of TB, and/or a combination thereof.

In another aspect, a computer program product includes a computer readable medium embodying program code executable by a processor of a computing device or system, the program code comprising: code that retrieves data attributed to a biological sample from an individual, wherein the data comprises biomarker values that correspond to at least one of the biomarkers provided in Tables 1, 2, 4, 5 or 8 to 12; code for comparing the biomarker value of the individual to a biomarker value of a control population; and code that executes a classification method that indicates a first evaluation of NED when there is no differential expression of the individual's biomarker value relative to the control population, or a second evaluation of EVD when there is differential expression of the individual's biomarker value relative to the control population.

In another aspect, the computer-implemented classification of TB status of an individual by the computer program product or the computer readable medium can reflect a diagnosis, treatment plan, prognosis, determination of recurrence or reactivation of TB, and/or a combination thereof. The evaluation of NED can be indicative of a diagnosis classification of no TB, a prognosis classification of an outcome of no TB at a selected future time point, a determination classification of no recurrence or reactivation of TB, and/or a combination thereof. The evaluation of EVD can be indicative of a diagnosis classification of TB, a prognosis classification of an outcome of TB at a selected future time point, a determination classification of recurrence or reactivation of TB, and/or a combination thereof.

In certain aspects of the disclosure, the biomarker panel or the number of biomarker values considered are selected from at least two biomarkers, at least three biomarkers, at least 4 biomarkers, at least 5 biomarkers, at least 6 biomarkers, at least 7 biomarkers, at least 8 biomarkers, at least 9 biomarkers, at least 10 biomarkers, and so on; wherein N can be any number of biomarkers from 1 biomarker to 239 biomarkers.

In other aspects of the disclosure, at least one biomarker is selected from Table 1, and/or Table 4, and/or Table 5, and/or Table 9, and/or Table 10, and/or Table 11, and/or Table 12. In other aspects of the disclosure, at least two biomarkers are selected from Table 1, and/or Table 4, and/or Table 5, and/or Table 9, and/or Table 10, and/or Table 11, and/or Table 12. In other aspects of the disclosure, at least three biomarkers are selected from Table 1, and/or Table 4, and/or Table 5, and/or Table 9, and/or Table 10, and/or Table 11, and/or Table 12. In other aspects of the disclosure, at least four biomarkers are selected from Table 1, and/or Table 4, and/or Table 5, and/or Table 9, and/or Table 10, and/or Table 11, and/or Table 12. In other aspects of the disclosure, at least five biomarkers are selected from Table 1, and/or Table 4, and/or Table 5, and/or Table 9, and/or Table 10, and/or Table 11, and/or Table 12. In other aspects of the disclosure, at least six biomarkers are selected from Table 1, and/or Table 4, and/or Table 5, and/or Table 9, and/or Table 10, and/or Table 11, and/or Table 12. In other aspects of the disclosure, at least seven biomarkers are selected from Table 1, and/or Table 4, and/or Table 5, and/or Table 9, and/or Table 10, and/or Table 11, and/or Table 12. In other aspects of the disclosure, at least eight biomarkers are selected from Table 1, and/or Table 4, and/or Table 5, and/or Table 9, and/or Table 10, and/or Table 11, and/or Table 12. In other aspects of the disclosure, at least nine biomarkers are selected from Table 1, and/or Table 4, and/or Table 5, and/or Table 9, and/or Table 10, and/or Table 11, and/or Table 12. In other aspects of the disclosure, at least ten biomarkers are selected from Table 1, and/or Table 4, and/or Table 5, and/or Table 9, and/or Table 10, and/or Table 11, and/or Table 12, and so on.

In other aspects, at least one biomarker is selected from the group consisting of TSP4, TIMP-2, SEPR, MRC-2, Antithrombin III, SAA, CRP, NPS-PLA2, LEAP-1, LBP, Coagulation factor V, XPNPEP1, PSME1, IL-11 Ra, HSP70, Galectin-8, a2-Antiplasmin, ECM1, YES, IGFBP-1, CATZ, BGN, LYNB and IL-7. In other aspects, at least two biomarker are selected from the group consisting of TSP4, TIMP-2, SEPR, MRC-2, Antithrombin III, SAA, CRP, NPS-PLA2, LEAP-1, LBP, Coagulation factor V, XPNPEP1, PSME1, IL-11 Ra, HSP70, Galectin-8, a2-Antiplasmin, ECM1, YES, IGFBP-1, CATZ, BGN, LYNB and IL-7. In other aspects, at least three biomarker are selected from the group consisting of TSP4, TIMP-2, SEPR, MRC-2, Antithrombin III, SAA, CRP, NPS-PLA2, LEAP-1, LBP, Coagulation factor V, XPNPEP1, PSME1, IL-11 Ra, HSP70, Galectin-8, a2-Antiplasmin, ECM1, YES, IGFBP-1, CATZ, BGN, LYNB and IL-7. In other aspects, at least four biomarker are selected from the group consisting of TSP4, TIMP-2, SEPR, MRC-2, Antithrombin III, SAA, CRP, NPS-PLA2, LEAP-1, LBP, Coagulation factor V, XPNPEP1, PSME1, IL-11 Ra, HSP70, Galectin-8, a2-Antiplasmin, ECM1, YES, IGFBP-1, CATZ, BGN, LYNB and IL-7. In other aspects, at least five biomarker are selected from the group consisting of TSP4, TIMP-2, SEPR, MRC-2, Antithrombin III, SAA, CRP, NPS-PLA2, LEAP-1, LBP, Coagulation factor V, XPNPEP1, PSME1, IL-11 Ra, HSP70, Galectin-8, a2-Antiplasmin, ECM1, YES, IGFBP-1, CATZ, BGN, LYNB and IL-7, etc.

BRIEF DESCRIPTION OF THE DRAWINGS

FIG. 3 illustrates an exemplary computer system for use with various computer-implemented methods described herein. System 100 is comprised of hardware elements that are electrically coupled via bus 108, including a processor 101, input device 102, output device 103, storage device 104, computer-readable storage media reader 105a, communications system 106 processing acceleration (e.g., DSP or special-purpose processors) 107 and memory 109. Computer-readable storage media reader 105a is further coupled to computer-readable storage media 105b, the combination comprehensively representing remote, local, fixed and/or removable storage devices plus storage media, memory, etc. for temporarily and/or more permanently containing computer-readable information, which can include storage device 104, memory 109 and/or any other such accessible system 100 resource. System 100 also comprises software elements (shown as being currently located within working memory 191) including an operating system 192 and other code 193, such as programs, data and the like.

FIG. 5 is a flowchart 3200 for a method of indicating the likelihood that an individual has TB in accordance with one embodiment. In block 3204, a computer can be utilized to retrieve biomarker information for an individual. In block 3208, a classification of the biomarker value can be performed with the computer. In block 3212, an indication can be made as to the TB status of the individual based upon the classification.

FIGS. 8A-8D illustrate markers of disease severity identified via linear regression analysis of the protein concentration correlated with disease severity score at baseline. FIGS. 8E-8F illustrate levels of a2-antiplasmin and fibrinogen (respectively) relative to disease severity score at 8 weeks. FIGS. 8G-8I illustrate markers of disease severity based on a regression analysis of the expression shift from baseline to week 8. Each dot represents an individual TB patient, showing the measurement of the indicated protein at the indicated time (8A-8F) or the ratio of the protein measurements at the two time-points (8G-8I).

FIG. 17A shows KS distance plots of all 1030 proteins measured in samples from responders versus slow-responders after 8 weeks of treatment. Squares mark the top ten proteins that are higher in responders (open squares) or slow-responders (solid squares). The dashed line indicates a Bonferroni-corrected 30% significance level. FIG. 17B shows cumulative distribution function (CDF) plots of the most differentially expressed proteins in responders (R) versus slow-responders (S) at 8 weeks of TB treatment. Axis labels and scales for RFU (x-axis) and for cumulative fraction of all samples within each group (y-axis) were omitted for clarity.

FIG. 19A depicts an ROC curve, showing AUC=0.88 and 95% confidence interval (0.75, 0.98). FIG. 19B depicts training sample classification. Solid squares represent true positive classifications, solid circles are true negative classifications; open squares are false positive and open circles are false negative results. Two samples were from subjects with drug-resistant (dr) TB strain.

FIG. 20B shows CDF plots of representative candidate treatment response markers identified via this KS distance metric. This figure illustrates that week eight responder samples (R) track distinctly different from week eight slow-responder samples (S) and all baseline samples (A).

FIG. 21A depicts stability paths for L1-regularized logistic regression using randomized lasso (weakness=0.25, W=0.9) applied to combination of baseline measurements and clinical covariates to classify responders from non-responders. Dashed lines indicate the expected number of false positive (FP) discoveries at different selection probability thresholds computed from class-randomized observations. FIG. 21B depicts stability paths for L1-regularized logistic regression of 8-week measurements and clinical covariates to classify responders from non-responders. FIG. 21C depicts training sample classification based on (log) odds ratio produced by logistic regression model using five markers (IL-11 R$\alpha$, $\alpha$2-Antiplasmin, PSME1, SAA, and subject age) measured at baseline. Solid squares represent true positive classifications (responders), solid circles are true negative classifications (slow-responders); open squares are false positive and open circles are false negative results. Two samples from subjects with drug-resistant TB are marked (dr). FIG. 21D depicts the corresponding ROC curve and point wise 95% CI for this analysis of the training samples, showing AUC=0.96 and bootstrapped 95% CI (0.88, 0.99).

FIG. 22A depicts regression of baseline protein data (log 10 RFU) on TTCC. FIG. 22B depicts regression of week-8 protein data (log RFU) on TTCC.

FIG. 22C depicts differential expression of proteins based on the medians of the responder groups at baseline (top) and at 8 weeks (bottom). FIG. 22D depicts regression of SAA data (log 10 RFU) on TTCC at baseline (left) and at 8 weeks (right).

DETAILED DESCRIPTION

Figure 1A:
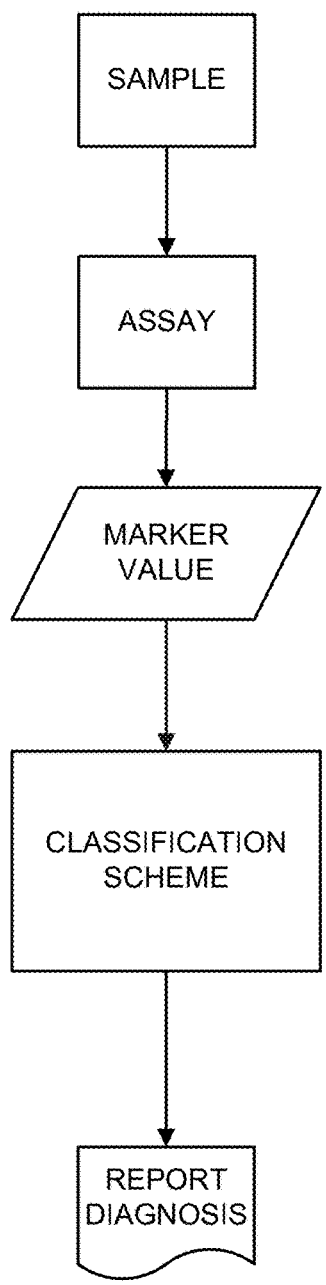
FIG. 1A is a flowchart for an exemplary method for detecting TB in a biological sample.
Figure 1B:
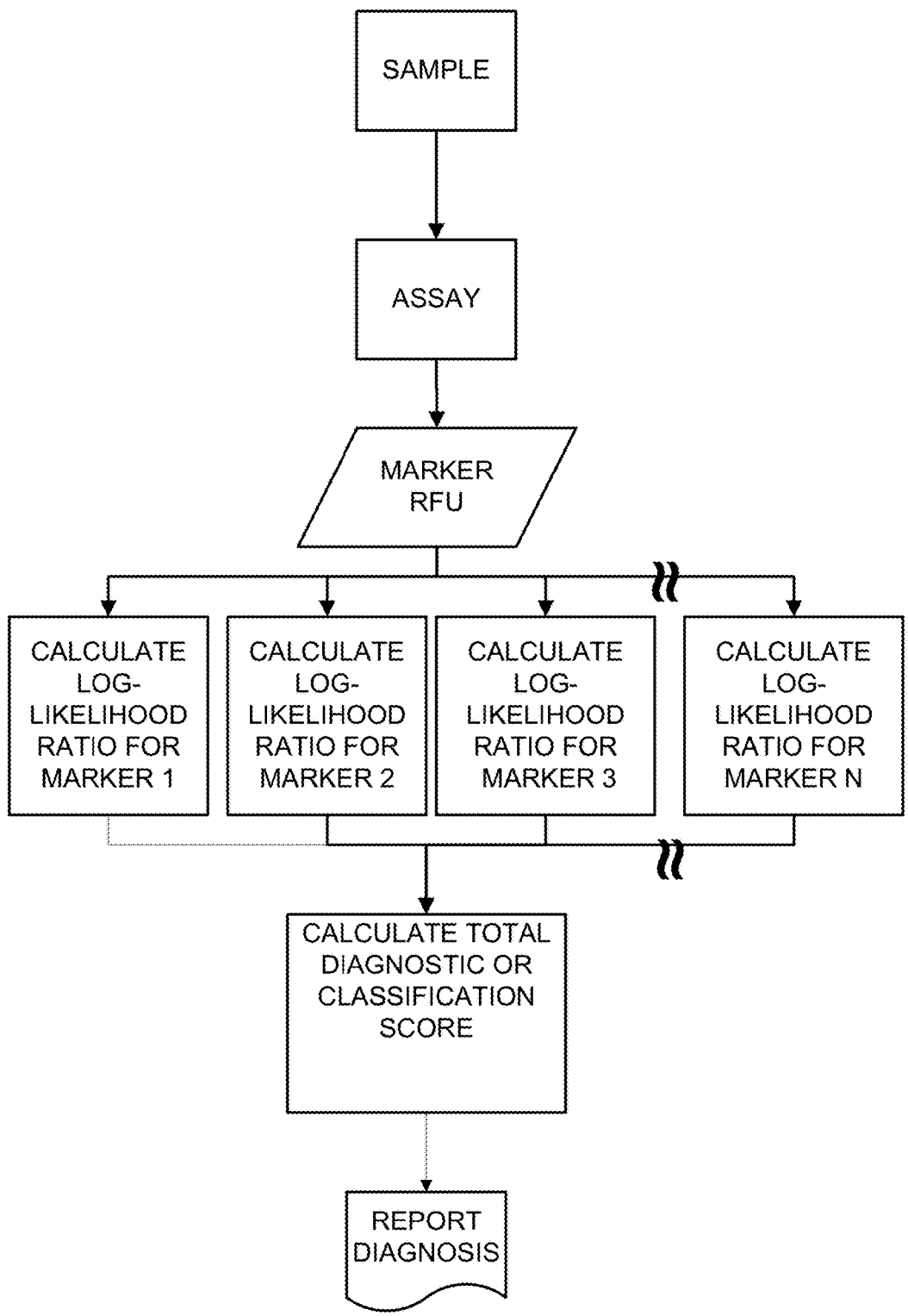
FIG. 1B is a flowchart for an exemplary method for detecting TB in a biological sample using a naïve Bayes classification method.

Reference will now be made in detail to representative embodiments of the invention. While the invention will be described in conjunction with the enumerated embodiments, it will be understood that the invention is not intended to be limited to those embodiments. On the contrary, the invention is intended to cover all alternatives, modifications, and equivalents that may be included within the scope of the present invention as defined by the claims.

One skilled in the art will recognize many methods and materials similar or equivalent to those described herein, which could be used in and are within the scope of the practice of the present invention. The present invention is in no way limited to the methods and materials described.

Unless defined otherwise, technical and scientific terms used herein have the same meaning as commonly understood by one of ordinary skill in the art to which this invention belongs. Although any methods, devices, and materials similar or equivalent to those described herein can be used in the practice or testing of the invention, the preferred methods, devices and materials are now described.

All publications, published patent documents, and patent applications cited in this application are indicative of the level of skill in the art(s) to which the application pertains. All publications, published patent documents, and patent applications cited herein are hereby incorporated by reference to the same extent as though each individual publication, published patent document, or patent application was specifically and individually indicated as being incorporated by reference.

As used in this application, including the appended claims, the singular forms "a," "an," and "the" include plural references, unless the content clearly dictates otherwise, and are used interchangeably with "at least one" and "one or more." Thus, reference to "an aptamer" includes mixtures of aptamers; reference to "a probe" includes mixtures of probes, and the like.

As used herein, the term "about" represents an insignificant modification or variation of the numerical value such that the basic function of the item to which the numerical value relates is unchanged.

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but may include other elements not expressly listed or inherent to such process, method, product-by-process, or composition of matter.

The present disclosure includes biomarkers, methods, devices, reagents, systems, and kits for the evaluation and treatment of TB, as well as the response to treatment in an individual. The specific intended uses and clinical applications for the subject invention include: 1) diagnosis of the presence or absence of TB; 2) treatment of TB; 3) prognosis during treatment and of the outcome of treatment for TB in an individual at a selected future time point; and 4) monitoring of recurrence or reactivation of TB in an individual that has apparently been cured of TB.

In one aspect, one or more biomarkers are provided for use either alone or in various combinations to evaluate TB, including the diagnosis of TB in an individual, treat TB upon diagnosis, the prognosis of the outcome of treatment for TB, the monitoring of recurrence or reactivation of TB, or the addressing other clinical indications. As described in detail below, exemplary embodiments include the biomarkers provided in Tables 1, 2, 4, 5, or 8 to 12, identified using a multiplex aptamer-based assay, as described generally in Example 1 and according to the method of Gold et al. (2010) PLoS ONE 5(12):e15004 doi:10.1371/journal.pone.0015004.

Tables 1, 2, 4, 5, or 8 to 12 set forth the findings obtained from analyzing serum samples from 39 individuals diagnosed with TB. The training group was designed to match the population with which a prognostic TB diagnostic test can have significant benefit. (These cases and controls were obtained from serum samples from 39 patients with pulmonary TB from Kampala, Uganda enrolled in the U.S. Center for Disease Control's TB Trials Consortium (CDC TBTC) Study 29). The potential biomarkers were measured in individual samples rather than pooling the disease samples; this allowed a better understanding of the individual and group variations in the phenotypes associated with the presence of disease at baseline and after 8 weeks of study therapy (in this case TB and its treatment). Since about 1030 protein measurements were made on each sample, and a total of 39 samples from the disease population were individually measured in all samples, Tables 1, 2, 4, 5, or 8 to 12 resulted from an analysis of a relatively large set of data.

The measurements were analyzed using the methods described in the section, "Classification of Biomarkers and Calculation of TB Prognosis Scores" herein.

While certain of the described TB biomarkers are useful alone for diagnosing, treating, prognosing, and/or determining the recurrence or reactivation of TB, methods are also described herein for the grouping of multiple subsets of the biomarkers, where each grouping or subset selection is useful as a panel of two or more biomarkers, interchangeably referred to herein as a "biomarker panel" and a "panel." Thus, various embodiments of the instant application provide combinations comprising N biomarkers, wherein N is selected from at least two, at least 3; at least 4, at least 5, at least 6, at least 7, at least 8, at least 9, at least 10, etc.

In one embodiment, the number of biomarkers useful for a biomarker subset or panel is based on the sensitivity and specificity value for the particular combination of biomarker values. The terms "sensitivity" and "specificity" are used herein with respect to the ability to correctly classify the TB diagnosis, TB prognosis and TB recurrence after apparent cure for an individual, based on one or more biomarker values detected in their biological sample. "Sensitivity" indicates the performance of the biomarker(s) with respect to correctly classifying individuals that have a positive TB diagnosis, a positive TB prognosis (EVD), or a positive TB recurrence after apparent cure, i.e., evidence of disease (EVD). "Specificity" indicates the performance of the biomarker(s) with respect to correctly classifying individuals who have a negative TB diagnosis, a negative TB prognosis (NED), or a negative TB recurrence following apparent cure of TB. For example, 85% specificity and 90% sensitivity for a panel of markers used to test a set of control samples and TB diagnosis samples indicates that 85% of the control samples were correctly classified as NED samples by the panel, and 90% of the positive samples were correctly classified as EVD samples by the panel.

The TB biomarkers identified herein represent a considerable number of choices for subsets or panels of biomarkers that can be used to effectively evaluate an individual for TB. Selection of the desired number of such biomarkers depends on the specific combination of biomarkers chosen. It is important to remember that panels of biomarkers for evaluation of TB in an individual may also include biomarkers not found in Tables 2 and 8 to 12, and that the inclusion of additional biomarkers not found in Tables 2 and 8 to 12 may reduce the number of biomarkers in the particular subset or panel that is selected from Tables 2 and 8 to 12. The number of biomarkers from Tables 2 and 8 to 12 used in a subset or panel may also be reduced if additional biomedical information is used in conjunction with the biomarker values to establish acceptable sensitivity and specificity values for a given assay.

Another factor that can affect the number of biomarkers to be used in a subset or panel of biomarkers is the procedures used to obtain biological samples from individuals who are being evaluated for TB. In a carefully controlled sample procurement environment, the number of biomarkers necessary to meet desired sensitivity and specificity values will be lower than in a situation where there can be more variation in sample collection, handling and storage.

In one embodiment, the subject invention comprises obtaining a biological sample from an individual or individuals of interest. The biological sample is then assayed to detect the presence of one or more (N) biomarkers of interest and to determine a biomarker value for each of said N biomarkers (typically measured as marker RFU (relative fluorescence units)). Once a biomarker has been detected and a biomarker value assigned, each marker is scored or classified as described in detail herein. The marker scores are then combined to provide a total evaluation score, which reflects whether the individual has evidence of disease, i.e., current TB diagnosis, prognosis of a future TB outcome, or current evidence of the recurrence of TB after an apparent cure.

"Biological sample", "sample", and "test sample" are used interchangeably herein to refer to any material, biological fluid, tissue, or cell obtained or otherwise derived from an individual. This includes blood (including whole blood, leukocytes, peripheral blood mononuclear cells, buffy coat, plasma, and serum), sputum, tears, mucus, nasal washes, nasal aspirate, breath, urine, semen, saliva, cyst fluid, meningeal fluid, amniotic fluid, glandular fluid, lymph fluid, nipple aspirate, bronchial aspirate, pleural fluid, peritoneal fluid, synovial fluid, joint aspirate, ascites, cells, a cellular extract, and cerebrospinal fluid. This also includes experimentally separated fractions of all of the preceding. For example, a blood sample can be fractionated into serum or into fractions containing particular types of blood cells, such as red blood cells or white blood cells (leukocytes). If desired, a sample can be a combination of samples from an individual, such as a combination of a tissue and fluid sample. The term "biological sample" also includes materials containing homogenized solid material, such as from a stool sample, a tissue sample, or a tissue biopsy, for example. The term "biological sample" also includes materials derived from a tissue culture or a cell culture. Any suitable methods for obtaining a biological sample may be employed; exemplary methods include, e.g., phlebotomy, urine collection, sputum collection, swab (e.g., buccal swab), lavage, and a fine needle aspirate biopsy procedure. Samples can also be collected, e.g., by micro dissection (e.g., laser capture micro dissection (LCM) or laser micro dissection (LMD), sputum, bronchoalveolar fluid, lung, fluid, lymph node or other relevant tissues. A "biological sample" obtained or derived from an individual includes any such sample that has been processed in any suitable manner after being obtained from the individual.

Further, it should be realized that a biological sample can be derived by taking biological samples from a number of individuals and pooling them or pooling an aliquot of each individual's biological sample. The pooled sample can be treated as a sample from a single individual and if the TB evaluation indicates evidence of disease (EVD) in the pooled sample, then each individual biological sample can be re-tested to determine which individuals have EVD.

For purposes of this specification, the phrase "data attributed to a biological sample from an individual" is intended to mean that the data in some form derived from, or were generated using, the biological sample of the individual. The data may have been reformatted, revised, or mathematically altered to some degree after having been generated, such as by conversion from units in one measurement system to units in another measurement system; but, the data are understood to have been derived from, or were generated using, the biological sample.

"Target", "target molecule", and "analyte" are used interchangeably herein to refer to any molecule of interest that may be present in a biological sample. A "molecule of interest" includes any minor variation of a particular molecule, such as, in the case of a protein, for example, minor variations in amino acid sequence, disulfide bond formation, glycosylation, lipidation, acetylation, phosphorylation, or any other manipulation or modification, such as conjugation with a labeling component, which does not substantially alter the identity of the molecule. A "target molecule", "target", or "analyte" is a set of copies of one type or species of molecule or multi-molecular structure. "Target molecules", "targets", and "analytes" refer to more than one such set of molecules. Exemplary target molecules include proteins, polypeptides, nucleic acids, carbohydrates, lipids, polysaccharides, glycoproteins, hormones, receptors, methylated nucleic acid, antigens, antibodies, affybodies, antibody mimics, viruses, pathogens, toxic substances, substrates, metabolites, transition state analogs, cofactors, inhibitors, drugs, dyes, nutrients, growth factors, cells, tissues, and any fragment or portion of any of the foregoing.

As used herein, "polypeptide," "peptide," and "protein" are used interchangeably to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Polypeptides can be single chains or associated chains. Also included within the definition are preproteins and intact mature proteins; peptides or polypeptides derived from a mature protein; fragments of a protein; splice variants; recombinant forms of a protein; protein variants with amino acid modifications, deletions, or substitutions; digests; and post-translational modifications, such as glycosylation, acetylation, phosphorylation, and the like.

As used herein, "marker" and "biomarker" are used interchangeably to refer to a target molecule that indicates or is a sign of a normal or abnormal process in an individual or of a disease or other condition in an individual. More specifically, a "marker" or "biomarker" is an anatomic, physiologic, biochemical, or molecular parameter associated with the presence of a specific physiological state or process, whether normal or abnormal, and, if abnormal, whether chronic or acute. Biomarkers are detectable and measurable by a variety of methods including laboratory assays and medical imaging. When a biomarker is a protein, it is also possible to use the expression of the corresponding gene as a surrogate measure of the amount or presence or absence of the corresponding protein biomarker in a biological sample or methylation state of the gene encoding the biomarker or proteins that control expression of the biomarker.

As used herein, "biomarker value", "value", "biomarker level", and "level" are used interchangeably to refer to a measurement that is made using any analytical method for detecting the biomarker in a biological sample and that indicates the presence, absence, absolute amount or concentration, relative amount or concentration, titer, a level, an expression level, a ratio of measured levels, or the like, of, for, or corresponding to the biomarker in the biological sample. The exact nature of the "value" or "level" depends on the specific design and components of the particular analytical method employed to detect the biomarker.

When a biomarker indicates or is a sign of an abnormal process or a disease or other condition in an individual, that biomarker is generally described as being either over-expressed or under-expressed as compared to an expression level or value of the biomarker that indicates or is a sign of a normal process or an absence of a disease or other condition in an individual. "Up-regulation", "up-regulated", "over-expression", "over-expressed", and any variations thereof are used interchangeably to refer to a value or level of a biomarker in a biological sample that is greater than a value or level (or range of values or levels) of the biomarker that is typically detected in similar biological samples from healthy or normal individuals. The terms may also refer to a value or level of a biomarker in a biological sample that is greater than a value or level (or range of values or levels) of the biomarker that may be detected at a different stage of a particular disease.

"Down-regulation", "down-regulated", "under-expression", "under-expressed", and any variations thereof are used interchangeably to refer to a value or level of a biomarker in a biological sample that is less than a value or level (or range of values or levels) of the biomarker that is typically detected in similar biological samples from healthy or normal individuals. The terms may also refer to a value or level of a biomarker in a biological sample that is less than a value or level (or range of values or levels) of the biomarker that may be detected at a different stage of a particular disease.

Further, a biomarker that is either over-expressed or under-expressed can also be referred to as being "differentially expressed" or as having a "differential level" or "differential value" as compared to a "normal" or "control" expression level or value of the biomarker that indicates or is a sign of a normal or a control process or an absence of a disease or other condition in an individual. Thus, "differential expression" of a biomarker can also be referred to as a variation from a "normal" or "control" expression level of the biomarker.

The term "differential gene expression" and "differential expression" are used interchangeably to refer to a gene (or its corresponding protein expression product) whose expression is activated to a higher or lower level in a subject suffering from a specific disease, relative to its expression in a normal or control subject. The terms also include genes (or the corresponding protein expression products) whose expression is activated to a higher or lower level at different stages of the same disease. It is also understood that a differentially expressed gene may be either activated or inhibited at the nucleic acid level or protein level, or may be subject to alternative splicing to result in a different polypeptide product. Such differences may be evidenced by a variety of changes including mRNA levels, surface expression, secretion or other partitioning of a polypeptide. Differential gene expression may include a comparison of expression between two or more genes or their gene products; or a comparison of the ratios of the expression between two or more genes or their gene products; or even a comparison of two differently processed products of the same gene, which differ between normal subjects and subjects suffering from a disease; or between various stages of the same disease. Differential expression includes both quantitative, as well as qualitative, differences in the temporal or cellular expression pattern in a gene or its expression products among, for example, normal and diseased cells, or among cells which have undergone different disease events or disease stages.

As used herein, "individual" refers to a test subject or patient. The individual can be a mammal or a non-mammal. In various embodiments, the individual is a mammal. A mammalian individual can be a human or non-human. In various embodiments, the individual is a human. A healthy or normal individual is an individual in which the disease or condition of interest is not detectable by conventional diagnostic methods.

"Diagnose", "diagnosing", "diagnosis", and variations thereof refer to the detection, determination, or recognition of a health status or condition of an individual based on one or more signs, symptoms, data, or other information pertaining to that individual. The health status of an individual can be diagnosed as healthy/normal (i.e., a diagnosis of the absence of a disease or condition) or diagnosed as ill/abnormal (i.e., a diagnosis of the presence, or an assessment of the characteristics, of a disease or condition). The terms "diagnose", "diagnosing", "diagnosis", etc., encompass, with respect to a particular disease or condition, the initial detection of the disease; the characterization or classification of the disease; the detection of the progression, remission, or recurrence or reactivation of the disease; and the detection of disease response after the administration of a treatment or therapy to the individual. The diagnosis of TB includes distinguishing individuals who have TB from individuals who do not.

"Prognose", "prognosing", "prognosis", and variations thereof refer to the prediction of a future course of a disease or condition in an individual who has the disease or condition (e.g., predicting patient survival), and such terms encompass the evaluation of disease response to the administration of a treatment or therapy to the individual. "Prognosing" and variants thereof can also mean predicting evidence of disease (EVD) or no evidence of disease (NED) in the individual at a future preselected time point. The date of prognosing can be referred to as time point 1 (TP1), and the preselected future time point may be referred to as time point 2 (TP2) and can include a specific future date or range of dates, for example post-treatment follow-up.

"Evaluate", "evaluating", "evaluation", and variations thereof encompass "diagnosing," "treating," "prognosing" and monitoring of recurrence in a treated individual. "Evaluating" TB can include any of the following: 1) diagnosing TB, i.e., initially detecting the presence or absence of TB; 2) prognosing at time point 1 (TP1), the future outcome of TB treatment at time point 2 (TP2), i.e., where TP2 may follow TB therapy; 3) detecting or monitoring TB progression or recurrence after apparent cure of TB, i.e., wherein "monitoring after apparent cure of TB" means testing an individual a time point after he or she has received successful treatment for TB, and/or 4) detecting progression from latent infection to active disease.

"Treatment," as used herein refers to an intervention performed with the intention of preventing the development or altering the pathology of a disorder. Accordingly, "treatment" refers to both therapeutic and prophylactic or preventative measures. Those in need of treatment include those already with the disorder as well as those in which the disorder is to be prevented. Standard treatment for TB currently comprises a standard regimen of rifampin in combination with isoniazid, ethambutol and pyrazinamide for the treatment of drug-susceptible TB, or second line antibiotics for drug-resistant TB.

"Therapy" as used herein refers to an intervention performed with the intention of preventing the development or altering the pathology of a disorder. "Therapy" refers to various methods that target particular diseases with particular disease fighting agents. For example, a targeted TB therapy might involve antimicrobial or immunomodulatory therapy directed at eradication the tubercle bacillus.

As used herein, "additional biomedical information" refers to one or more evaluations of an individual, other than using any of the biomarkers described herein, that are associated with TB risk. "Additional biomedical information" includes any of the following: signs and symptoms of disease, physical descriptors of an individual; the height and/or weight (BMI) of an individual; change in weight; the gender and ethnicity of an individual; relevant secondary diagnosis (e.g. extrapulmonary or pleural involvement); additional comorbid disease information (e.g. HIV, malaria, malignancies, hepatic disorders, diabetes, etc.); current prescription and non-prescription drug use (e.g. TB regimen and how many days of treatment received before sample taken, other medications); tobacco, alcohol, recreational drug use; any lab results (relevant culture results, i.e. bacillary burden in the sample, time to culture positivity or time to culture conversion to the negative if available, sputum smear results; CXR cavitation, extent if available); occupational history; family history; the presence of a genetic marker(s) correlating with a higher risk of TB in the individual or a family member; other clinical symptoms such as persistent cough, fever, weight loss. Additional biomedical information can be obtained from an individual using routine techniques known in the art, such as from the individual themselves by use of a routine patient questionnaire or health history questionnaire, etc., or from a medical practitioner, etc. Alternately, additional biomedical information can be obtained from study investigators, data collection forms, interviews etc.

Testing of biomarker levels in combination with an evaluation of any additional biomedical information, including other laboratory tests, may, for example, improve sensitivity, specificity, and/or AUC for detecting TB (or other TB-related uses) as compared to biomarker testing alone or evaluating any particular item of additional biomedical information alone.

The term "area under the curve" or "AUC" refers to the area under the curve of a receiver operating characteristic (ROC) curve, both of which are well known in the art. AUC measures are useful for comparing the accuracy of a classifier across the complete data range. Classifiers with a greater AUC have a greater capacity to classify unknowns correctly between two groups of interest (e.g., TB samples and normal or control samples or TB samples from patients with different forms of the TB disease (e.g. severe vs. mild, pulmonary vs. extrapulmonary disease). ROC curves are useful for plotting the performance of a particular feature (e.g., any of the biomarkers described herein and/or any item of additional biomedical information such as responders to treatment vs. non-responders) in distinguishing between two populations (e.g., cases having TB and controls without TB or those who fail treatment or are likely to be slowly responding to TB treatment). Typically, the feature data across the entire population (e.g., the cases and controls) are sorted in ascending order based on the value of a single feature. Then, for each value for that feature, the true positive and false positive rates for the data are calculated. The true positive rate is determined by counting the number of cases above the value for that feature and then dividing by the total number of cases. The false positive rate is determined by counting the number of controls above the value for that feature and then dividing by the total number of controls. Although this definition refers to scenarios in which a feature is elevated in cases compared to controls, this definition also applies to scenarios in which a feature is lower in cases compared to the controls (in such a scenario, samples below the value for that feature would be counted). ROC curves can be generated for a single feature as well as for other single outputs, for example, a combination of two or more features can be mathematically combined (e.g., added, subtracted, multiplied, etc.) to provide a single sum value, and this single sum value can be plotted in a ROC curve. Additionally, any combination of multiple features, in which the combination derives a single output value, can be plotted in a ROC curve. These combinations of features may comprise a test. The ROC curve is the plot of the true positive rate (sensitivity) of a test against the false positive rate (1-specificity) of the test.

As used herein, "detecting" or "determining" with respect to a biomarker value includes the use of both the instrument required to observe and record a signal corresponding to a biomarker value and the material/s required to generate that signal. In various embodiments, the biomarker value is detected using any suitable method, including fluorescence, chemiluminescence, surface plasmon resonance, surface acoustic waves, mass spectrometry, infrared spectroscopy, Raman spectroscopy, atomic force microscopy, scanning tunneling microscopy, electrochemical detection methods, nuclear magnetic resonance, quantum dots, and the like. "Detecting" and "determining," used interchangeably herein, both refer to the identification or observation of the presence of a biomarker in a biological sample, and/or to the measurement of the biomarker value.

"Solid support" refers herein to any substrate having a surface to which molecules may be attached, directly or indirectly, through either covalent or non-covalent bonds. A "solid support" can have a variety of physical formats, which can include, for example, a membrane; a chip (e.g., a protein chip); a slide (e.g., a glass slide or coverslip); a column; a hollow, solid, semi-solid, pore- or cavity-containing particle, such as, for example, a bead; a gel; a fiber, including a fiber optic material; a matrix; and a sample receptacle. Exemplary sample receptacles include sample wells, tubes, capillaries, vials, and any other vessel, groove or indentation capable of holding a sample. A sample receptacle can be contained on a multi-sample platform, such as a microtiter plate, slide, microfluidics device, and the like. A support can be composed of a natural or synthetic material, an organic or inorganic material. The composition of the solid support on which capture reagents are attached generally depends on the method of attachment (e.g., covalent attachment). Other exemplary receptacles include microdroplets and microfluidic controlled or bulk oil/aqueous emulsions within which assays and related manipulations can occur. Suitable solid supports include, for example, plastics, resins, polysaccharides, silica or silica-based materials, functionalized glass, modified silicon, carbon, metals, inorganic glasses, membranes, nylon, natural fibers (such as, for example, silk, wool and cotton), polymers, and the like. The material composing the solid support can include reactive groups such as, for example, carboxy, amino, or hydroxyl groups, which are used for attachment of the capture reagents. Polymeric solid supports can include, e.g., polystyrene, polyethylene glycol tetraphthalate, polyvinyl acetate, polyvinyl chloride, polyvinyl pyrrolidone, polyacrylonitrile, polymethyl methacrylate, polytetrafluoroethylene, butyl rubber, styrenebutadiene rubber, natural rubber, polyethylene, polypropylene, (poly)tetrafluoroethylene, (poly)vinylidenefluoride, polycarbonate, and polymethylpentene. Suitable solid support particles that can be used include, e.g., encoded particles, such as Luminex®-type encoded particles, magnetic particles, and glass particles.

Exemplary Uses of Biomarkers

In various exemplary embodiments, methods are provided for diagnosing TB in an individual by detecting one or more biomarker values corresponding to one or more biomarkers that are present in the circulation of an individual, such as in serum or plasma or secreted or excreted in the urine or present in the sputum, by any number of analytical methods, including any of the analytical methods described herein. These biomarkers are, for example, differentially expressed in individuals with TB as compared to individuals without TB. Detection of the differential expression of a biomarker in an individual can be used, for example, to permit the early diagnosis of TB, to treat TB once detected, to prognose future outcome of TB in an individual following therapy and/or to monitor TB recurrence after therapy, predicting who might go on from latent infection to active disease or for other clinical indications.

Any of the biomarkers described herein may be used in a variety of clinical indications for TB, including, but not limited to detection of TB (such as in a high-risk or symptomatic individual or population); treating TB, determining TB prognosis; monitoring TB progression or monitoring for TB recurrence; monitoring treatment selection; monitoring response to a therapeutic agent or other treatment; combining biomarker testing with additional biomedical information, as detailed above; and facilitating decisions regarding clinical follow-up. Furthermore, the described biomarkers may also be useful in permitting certain of these uses before indications of TB are detected by imaging modalities or other clinical correlates, or before symptoms appear.

As an example of the manner in which any of the biomarkers described herein can be used to diagnose TB, differential expression of one or more of the described biomarkers in an individual who is not known to have TB may indicate that the individual has TB, thereby enabling detection of TB at an early stage of the disease when treatment is most effective, perhaps before the TB is detected by other means or before symptoms appear. Increased differential expression from "normal" (since some biomarkers may be down-regulated with disease) of one or more of the biomarkers during the course of TB may be indicative of TB progression (and thus indicate a poor prognosis), whereas a decrease in the degree to which one or more of the biomarkers is differentially expressed (i.e., in subsequent biomarker tests, the expression level in the individual is moving toward or approaching a "normal" expression level) may be indicative of TB resolution (and thus indicate a good or better prognosis and indicate a positive response to therapy). Similarly, an increase in the degree to which one or more of the biomarkers is differentially expressed (i.e., in subsequent biomarker tests, the expression level in the individual is moving further away from a "normal" expression level) during the course of TB treatment may indicate that the TB is progressing or that drug resistant TB is present and therefore indicate that the treatment is ineffective or be an early indicator that the TB bacillus is resistant to one or more of the drugs the patient is being treated with, whereas a decrease in differential expression of one or more of the biomarkers during the course of TB treatment may be indicative of TB response to treatment and therefore indicate that the treatment is working successfully. Additionally, an increase or decrease in the differential expression of one or more of the biomarkers after an individual has apparently been cured of TB may be indicative of TB recurrence. In a situation such as this, for example, the individual can be restarted on therapy. Furthermore, a differential expression level of one or more of the biomarkers in an individual may be predictive of the individual's response to a particular therapeutic agent. In monitoring for TB recurrence or progression, changes in the biomarker expression levels may indicate the need for repetitive biomarker assays or repeat imaging, such as to determine TB infection status or burden or to determine the need for changes in treatment or to inform clinical trial investigators of the superiority of one test regimen over another. Measuring biomarker changes longitudinally within an individual establishes a personal baseline and provides a sensitive method to detect changes that may be evident prior to clinical emergence of altered disease state.

Detection of any of the biomarkers described herein may be particularly useful following, or in conjunction with, TB treatment, such as to evaluate the success of the treatment or to monitor TB, recurrence, reactivation, and/or progression following treatment. TB treatment may include, for example, administration of one or more therapeutic agent to the individual or any other type of TB treatment used in the art, and any combination of these treatments. For example, any of the biomarkers may be detected at least once after treatment or may be detected multiple times after treatment (such as at periodic intervals), or may be detected both before and after treatment. Differential expression levels of any of the biomarkers in an individual over time may be indicative of TB progression, recurrence or reactivation examples of which include any of the following: an increase or decrease in the expression level of the biomarkers after treatment compared with the expression level of the biomarker before treatment; an increase or decrease in the expression level of the biomarker at a later time point after treatment compared with the expression level of the biomarker at an earlier time point after treatment; and a differential expression level of the biomarker at a single time point after treatment compared with normal levels of the biomarker.

In addition to testing biomarker levels in conjunction with relevant symptoms, physical signs, microbiological data or imaging data, information regarding the biomarkers can also be evaluated in conjunction with other types of data, particularly data that indicates an individual's risk for TB (e.g., body fluid, tissue culture for the causative agent of TB, patient clinical history, radiographic severity of disease, symptoms, family history of TB, risk factors such as the presence of a genetic marker(s), and/or status of other biomarkers, clinical symptoms, etc.). These various data can be assessed by automated methods, such as a computer program/software, which can be embodied in a computer or other apparatus/device.

Any of the described biomarkers may also be used in imaging tests. For example, an imaging agent can be coupled to any of the described biomarkers, which can be used to aid in TB diagnosis, to prognose outcome following treatment, to monitor disease progression/remission, to monitor for disease recurrence, reactivation or to monitor response to therapy, among other uses.

Detection and Determination of Biomarkers and Biomarker Values

A biomarker value for the biomarkers described herein can be detected using any of a variety of known analytical methods. In one embodiment, a biomarker value is detected using a capture reagent. As used herein, a "capture agent" or "capture reagent" refers to a molecule that is capable of binding specifically to a biomarker. In various embodiments, the capture reagent can be exposed to the biomarker in solution or can be exposed to the biomarker while the capture reagent is immobilized on a solid support. In other embodiments, the capture reagent contains a feature that is reactive with a secondary feature on a solid support. In these embodiments, the capture reagent can be exposed to the biomarker in solution, and then the feature on the capture reagent can be used in conjunction with the secondary feature on the solid support to immobilize the biomarker on the solid support. The capture reagent is selected based on the type of analysis to be conducted. Capture reagents include but are not limited to aptamers, antibodies, adnectins, ankyrins, other antibody mimetics and other protein scaffolds, autoantibodies, chimeras, small molecules, an F(ab')$_2$ fragment, a single chain antibody fragment, an Fv fragment, a single chain Fv fragment, a nucleic acid, a lectin, a ligand-binding receptor, affybodies, nanobodies, imprinted polymers, avimers, peptidomimetics, a hormone receptor, a cytokine receptor, and synthetic receptors, and modifications and fragments of these.

In some embodiments, a biomarker value is detected using a biomarker/capture reagent complex.

In other embodiments, the biomarker value is derived from the biomarker/capture reagent complex and is detected indirectly, such as, for example, as a result of a reaction that is subsequent to the biomarker/capture reagent interaction, but is dependent on the formation of the biomarker/capture reagent complex.

In some embodiments, the biomarker value is detected directly from the biomarker in a biological sample.

In one embodiment, the biomarkers are detected using a multiplexed format that allows for the simultaneous detection of two or more biomarkers in a biological sample. In one embodiment of the multiplexed format, capture reagents are immobilized, directly or indirectly, covalently or non-covalently, in discrete locations on a solid support. In another embodiment, a multiplexed format uses discrete solid supports where each solid support has a unique capture reagent associated with that solid support, such as, for example quantum dots. In another embodiment, an individual device is used for the detection of each one of multiple biomarkers to be detected in a biological sample. Individual devices can be configured to permit each biomarker in the biological sample to be processed simultaneously. For example, a microtiter plate can be used such that each well in the plate is used to uniquely analyze one of multiple biomarkers to be detected in a biological sample.

In one or more of the foregoing embodiments, a fluorescent tag can be used to label a component of the biomarker/capture complex to enable the detection of the biomarker value. In various embodiments, the fluorescent label can be conjugated to a capture reagent specific to any of the biomarkers described herein using known techniques, and the fluorescent label can then be used to detect the corresponding biomarker value. Suitable fluorescent labels include rare earth chelates, fluorescein and its derivatives, rhodamine and its derivatives, dansyl, allophycocyanin, PBXL-3, Qdot 605, Lissamine, phycoerythrin, Texas Red, and other such compounds.

In one embodiment, the fluorescent label is a fluorescent dye molecule. In some embodiments, the fluorescent dye molecule includes at least one substituted indolium ring system in which the substituent on the 3-carbon of the indolium ring contains a chemically reactive group or a conjugated substance. In some embodiments, the dye molecule includes an AlexaFluor molecule, such as, for example, AlexaFluor 488, AlexaFluor 532, AlexaFluor 647, AlexaFluor 680, or AlexaFluor 700. In other embodiments, the dye molecule includes a first type and a second type of dye molecule, such as, e.g., two different AlexaFluor molecules. In other embodiments, the dye molecule includes a first type and a second type of dye molecule, and the two dye molecules have different emission spectra.

Fluorescence can be measured with a variety of instrumentation compatible with a wide range of assay formats. For example, spectrofluorimeters have been designed to analyze microtiter plates, microscope slides, printed arrays, cuvettes, etc. (Principles of Fluorescence Spectroscopy, by J. R. Lakowicz, Springer Science+Business Media, Inc., (2004); Bioluminescence & Chemiluminescence: Progress & Current Applications; Philip E. Stanley and Larry J. Kricka editors, World Scientific Publishing Company, January (2002)).

In one or more of the foregoing embodiments, a chemiluminescence tag can optionally be used to label a component of the biomarker/capture complex to enable the detection of a biomarker value. Suitable chemiluminescent materials include any of oxalyl chloride, Rodamin 6G, Ru(bipy)$_3^{2+}$, TMAE (tetrakis(dimethylamino)ethylene), Pyrogallol (1,2,3-trihydroxibenzene), Lucigenin, peroxyoxalates, Aryl oxalates, Acridinium esters, dioxetanes, and others.

In yet other embodiments, the detection method includes an enzyme/substrate combination that generates a detectable signal that corresponds to the biomarker value. Generally, the enzyme catalyzes a chemical alteration of the chromogenic substrate which can be measured using various techniques, including spectrophotometry, fluorescence, and chemiluminescence. Suitable enzymes include, for example, luciferases, luciferin, malate dehydrogenase, urease, horseradish peroxidase (HRPO), alkaline phosphatase, beta-galactosidase, glucoamylase, lysozyme, glucose oxidase, galactose oxidase, and glucose-6-phosphate dehydrogenase, uricase, xanthine oxidase, lactoperoxidase, microperoxidase, and the like.

In yet other embodiments, the detection method can be a combination of fluorescence, chemiluminescence, radionuclide or enzyme/substrate combinations that generate a measurable signal. Multimodal signaling could have unique and advantageous characteristics in biomarker assay formats.

More specifically, the biomarker values for the biomarkers described herein can be detected using known analytical methods including, singleplex aptamer assays, multiplexed aptamer assays, singleplex or multiplexed immunoassays, mRNA expression profiling, miRNA expression profiling, mass spectrometric analysis, histological/cytological methods, etc. as detailed below.

Determination of Biomarker Values Using Aptamer-Based Assays

Assays directed to the detection and quantification of physiologically significant molecules in biological samples and other samples are important tools in scientific research and in the health care field. One class of such assays involves the use of a microarray that includes one or more aptamers immobilized on a solid support. The aptamers are each capable of binding to a target molecule in a highly specific manner and with very high affinity. See, e.g., U.S. Pat. No. 5,475,096 entitled "Nucleic Acid Ligands," see also, e.g., U.S. Pat. Nos. 6,242,246, 6,458,543, and 6,503,715, each of which is entitled "Nucleic Acid Ligand Diagnostic Biochip." Once the microarray is contacted with a sample, the aptamers bind to their respective target molecules present in the sample and thereby enable a determination of a biomarker value corresponding to a biomarker.

As used herein, an "aptamer" refers to a nucleic acid that has a specific binding affinity for a target molecule. It is recognized that affinity interactions are a matter of degree; however, in this context, the "specific binding affinity" of an aptamer for its target means that the aptamer binds to its target generally with a much higher degree of affinity than it binds to other components in a test sample. An "aptamer" is a set of copies of one type or species of nucleic acid molecule that has a particular nucleotide sequence. An aptamer can include any suitable number of nucleotides, including any number of chemically modified nucleotides. "Aptamers" refers to more than one such set of molecules. Different aptamers can have either the same or a different numbers of nucleotides. Aptamers can be DNA or RNA or chemically modified nucleic acids and can be single stranded, double stranded, or contain double stranded regions, and can include higher ordered structures. An aptamer may be a slow off rate modified aptamer or SOMAmer™ aptamer. (See, e.g., U.S. Pat. No. 7,947,447, entitled "A Method for Generating Aptamers with Improved Off-Rates.") An aptamer can also be a photoaptamer, where a photoreactive or chemically reactive functional group is included in the aptamer to allow it to be covalently linked to its corresponding target. Any of the aptamer methods disclosed herein can include the use of two or more aptamers that specifically bind the same target molecule. As further described below, an aptamer may include a tag. If an aptamer includes a tag, all copies of the aptamer need not have the same tag. Moreover, if different aptamers each include a tag, these different aptamers can have either the same tag or a different tag.

An aptamer can be identified using any known method, including the SELEX process. Once identified, an aptamer can be prepared or synthesized in accordance with any known method, including chemical synthetic methods and enzymatic synthetic methods.

The terms "SELEX" and "SELEX process" are used interchangeably herein to refer generally to a combination of (1) the selection of aptamers that interact with a target molecule in a desirable manner, for example binding with high affinity to a protein, with (2) the amplification of those selected nucleic acids. The SELEX process can be used to identify aptamers with high affinity to a specific target or biomarker.

SELEX generally includes preparing a candidate mixture of nucleic acids, binding of the candidate mixture to the desired target molecule to form an affinity complex, separating the affinity complexes from the unbound candidate nucleic acids, separating and isolating the nucleic acid from the affinity complex, purifying the nucleic acid, and identifying a specific aptamer sequence. The process may include multiple rounds to further refine the affinity of the selected aptamer. The process can include amplification steps at one or more points in the process. See, e.g., U.S. Pat. No. 5,475,096, entitled "Nucleic Acid Ligands". The SELEX process can be used to generate an aptamer that covalently binds its target as well as an aptamer that non-covalently binds its target. See, e.g., U.S. Pat. No. 5,705,337 entitled "Systematic Evolution of Nucleic Acid Ligands by Exponential Enrichment: Chemi-SELEX."

The SELEX process can be used to identify high-affinity aptamers containing modified nucleotides that confer improved characteristics on the aptamer, such as, for example, improved in vivo stability or improved delivery characteristics. Examples of such modifications include chemical substitutions at the ribose and/or phosphate and/or base positions. SELEX process-identified aptamers containing modified nucleotides are described in U.S. Pat. No. 5,660,985, entitled "High Affinity Nucleic Acid Ligands Containing Modified Nucleotides", which describes oligonucleotides containing nucleotide derivatives chemically modified at the 5'- and 2'-positions of pyrimidines. U.S. Pat. No. 5,580,737, see supra, describes highly specific aptamers containing one or more nucleotides modified with 2'-amino (2'-NH2), 2'-fluoro (2'-F), and/or 2'-O-methyl (2'-OMe). See also, U.S. Patent Application Publication 2009/0098549, entitled "SELEX and PHOTOSELEX", which describes nucleic acid libraries having expanded physical and chemical properties and their use in SELEX and photoSELEX.

A variation of this assay employs aptamers that include photoreactive functional groups that enable the aptamers to covalently bind or "photocrosslink" their target molecules. See, e.g., U.S. Pat. No. 6,544,776 entitled "Nucleic Acid Ligand Diagnostic Biochip". These photoreactive aptamers are also referred to as photoaptamers. See, e.g., U.S. Pat. Nos. 5,763,177, 6,001,577, and 6,291,184, each of which is entitled "Systematic Evolution of Nucleic Acid Ligands by Exponential Enrichment: Photoselection of Nucleic Acid Ligands and Solution SELEX"; see also, e.g., U.S. Pat. No. 6,458,539, entitled "Photoselection of Nucleic Acid Ligands". After the microarray is contacted with the sample and the photoaptamers have had an opportunity to bind to their target molecules, the photoaptamers are photoactivated, and the solid support is washed to remove any non-specifically bound molecules. Harsh wash conditions may be used, since target molecules that are bound to the photoaptamers are generally not removed, due to the covalent bonds created by the photoactivated functional group(s) on the photoaptamers. In this manner, the assay enables the detection of a biomarker value corresponding to a biomarker in the test sample.

In both of these assay formats, the aptamers are immobilized on the solid support prior to being contacted with the sample. Under certain circumstances, however, immobilization of the aptamers prior to contact with the sample may not provide an optimal assay. For example, pre-immobilization of the aptamers may result in inefficient mixing of the aptamers with the target molecules on the surface of the solid support, perhaps leading to lengthy reaction times and, therefore, extended incubation periods to permit efficient binding of the aptamers to their target molecules. Further, when photoaptamers are employed in the assay and depending upon the material utilized as a solid support, the solid support may tend to scatter or absorb the light used to effect the formation of covalent bonds between the photoaptamers and their target molecules. Moreover, depending upon the method employed, detection of target molecules bound to their aptamers can be subject to imprecision, since the surface of the solid support may also be exposed to and affected by any labeling agents that are used. Finally, immobilization of the aptamers on the solid support generally involves an aptamer-preparation step (i.e., the immobilization) prior to exposure of the aptamers to the sample, and this preparation step may affect the activity or functionality of the aptamers.

Aptamer assays that permit an aptamer to capture its target in solution and then employ separation steps that are designed to remove specific components of the aptamer-target mixture prior to detection have also been described (see U.S. Pat. No. 7,947,447, entitled "Multiplexed Analyses of Test Samples"). The described aptamer assay methods enable the detection and quantification of a non-nucleic acid target (e.g., a protein target) in a test sample by detecting and quantifying a nucleic acid (i.e., an aptamer). The described methods create a nucleic acid surrogate (i.e., the aptamer) for detecting and quantifying a non-nucleic acid target, thus allowing the wide variety of nucleic acid technologies, including amplification, to be applied to a broader range of desired targets, including protein targets.

Aptamers can be constructed to facilitate the separation of the assay components from an aptamer biomarker complex (or photoaptamer biomarker covalent complex) and permit isolation of the aptamer for detection and/or quantification. In one embodiment, these constructs can include a cleavable or releasable element within the aptamer sequence. In other embodiments, additional functionality can be introduced into the aptamer, for example, a labeled or detectable component, a spacer component, or a specific binding tag or immobilization element. For example, the aptamer can include a tag connected to the aptamer via a cleavable moiety, a label, a spacer component separating the label, and the cleavable moiety. In one embodiment, a cleavable element is a photocleavable linker. The photocleavable linker can be attached to a biotin moiety and a spacer section, can include an NHS group for derivatization of amines, and can be used to introduce a biotin group to an aptamer, thereby allowing for the release of the aptamer later in an assay method.

Homogenous assays, done with all assay components in solution, do not require separation of sample and reagents prior to the detection of signal. These methods are rapid and easy to use. These methods generate signal based on a molecular capture or binding reagent that reacts with its specific target. For TB, the molecular capture reagents would be an aptamer or an antibody or the like and the specific target would be a TB biomarker of Tables 2 or 8 to 12.

In one embodiment, a method for signal generation takes advantage of anisotropy signal change due to the interaction of a fluorophore-labeled capture reagent with its specific biomarker target. When the labeled capture reacts with its target, the increased molecular weight causes the rotational motion of the fluorophore attached to the complex to become much slower changing the anisotropy value. By monitoring the anisotropy change, binding events may be used to quantitatively measure the biomarkers in solutions. Other methods include fluorescence polarization assays, molecular beacon methods, time resolved fluorescence quenching, chemiluminescence, fluorescence resonance energy transfer, and the like.

An exemplary solution-based aptamer assay that can be used to detect a biomarker value corresponding to a biomarker in a biological sample includes the following: (a) preparing a mixture by contacting the biological sample with an aptamer that includes a first tag and has a specific affinity for the biomarker, wherein an aptamer affinity complex is formed when the biomarker is present in the sample; (b) exposing the mixture to a first solid support including a first capture element, and allowing the first tag to associate with the first capture element; (c) removing any components of the mixture not associated with the first solid support; (d) attaching a second tag to the biomarker component of the aptamer affinity complex; (e) releasing the aptamer affinity complex from the first solid support; (f) exposing the released aptamer affinity complex to a second solid support that includes a second capture element and allowing the second tag to associate with the second capture element; (g) removing any non-complexed aptamer from the mixture by partitioning the non-complexed aptamer from the aptamer affinity complex; (h) eluting the aptamer from the solid support; and (i) detecting the biomarker by detecting the aptamer component of the aptamer affinity complex.

SELEX can also be used to identify aptamers that have desirable off-rate characteristics. See U.S. Pat. No. 7,947, 447, entitled "Method for Generating Aptamers with Improved Off-Rates", which describes improved SELEX methods for generating aptamers that can bind to target molecules. Methods for producing aptamers and photoaptamers having slower rates of dissociation from their respective target molecules (also referred to herein as SOMAmer™ aptamers) are described. The methods involve contacting the candidate mixture with the target molecule, allowing the formation of nucleic acid-target complexes to occur, and performing a slow off-rate enrichment process wherein nucleic acid-target complexes with fast dissociation rates will dissociate and not reform, while complexes with slow dissociation rates will remain intact. Additionally, the methods include the use of modified nucleotides in the production of candidate nucleic acid mixtures to generate aptamers with improved off-rate performance.

Regarding their use in diagnostic applications, aptamers, including slow off-rate aptamers have several advantages over antibodies, including lower molecular weight, higher multiplexing capabilities (low cross-reactivity, universally-applicable assay conditions), chemical stability (to heat, drying, and solvents, reversible renaturation), ease of reagent manufacturing, consistent lot-to-lot performance and lower cost (fully synthetic). They are stable at room temperature and over a range of physiochemical conditions.

Any means known in the art can be used to detect a biomarker value by detecting the aptamer component of an aptamer affinity complex. A number of different detection methods can be used to detect the aptamer component of an affinity complex, such as, for example, hybridization assays, mass spectroscopy, or QPCR. In some embodiments, nucleic acid sequencing methods can be used to detect the aptamer component of an aptamer affinity complex and thereby detect a biomarker value. Briefly, a test sample can be subjected to any kind of nucleic acid sequencing method to identify and quantify the sequence or sequences of one or more aptamers present in the test sample.

In some embodiments, the sequence includes the entire aptamer molecule or any portion of the molecule that may be used to uniquely identify the molecule. In other embodiments, the identifying sequencing is a specific sequence added to the aptamer; such sequences are often referred to as "tags," "barcodes," or "zipcodes."

In some embodiments, the sequencing method includes enzymatic steps to amplify the aptamer sequence or to convert any kind of nucleic acid, including RNA and DNA that contain chemical modifications to any position, to any other kind of nucleic acid appropriate for sequencing.

In some embodiments, the sequencing method includes one or more cloning steps. In other embodiments the sequencing method includes a direct sequencing method without cloning.

In some embodiments, the sequencing method includes a directed approach with specific primers that target one or more aptamers in the test sample. In other embodiments, the sequencing method includes a shotgun approach that targets all aptamers in the test sample.

In some embodiments, the sequencing method includes enzymatic steps to amplify the molecule targeted for sequencing. In other embodiments, the sequencing method directly sequences single molecules.

An exemplary nucleic acid sequencing-based method that can be used to detect a biomarker value corresponding to a biomarker in a biological sample includes the following: (a) converting a mixture of aptamers that contain chemically modified nucleotides to unmodified nucleic acids with an enzymatic step; (b) shotgun sequencing the resulting unmodified nucleic acids with a massively parallel sequencing platform such as, for example, the 454 Sequencing System (454 Life Sciences/Roche), the Illumina Sequencing System (Illumina), the ABI SOLiD SequencingSystem (Applied Biosystems), the HeliScope Single Molecule Sequencer (Helicos Biosciences), or the Pacific Biosciences Real Time Single-Molecule Sequencing System (Pacific BioSciences) or the Polonator G Sequencing System (Dover Systems); and (c) identifying and quantifying the aptamers present in the mixture by specific sequence and sequence count.

Determination of Biomarker Values Using Immunoassays

Immunoassay methods are based on the reaction of an antibody to its corresponding target or analyte and can detect the analyte in a sample depending on the specific assay format. To improve specificity and sensitivity of an assay method based on immuno-reactivity, monoclonal antibodies are often used because of their specific epitope recognition. Polyclonal antibodies have also been successfully used in various immunoassays due to their increased affinity for the target as compared to monoclonal antibodies. Immunoassays have been designed for use with a wide range of biological sample matrices. Immunoassay formats have been designed to provide qualitative, semi-quantitative, and quantitative results.

Quantitative results are generated through the use of a standard curve created with known concentrations of the specific analyte to be detected. The response or signal from an unknown sample is plotted onto the standard curve, and a quantity or value corresponding to the target in the unknown sample is established.

Numerous immunoassay formats have been designed. ELISA or EIA can be quantitative for the detection of an analyte. This method relies on attachment of a label to either the analyte or the antibody and the label component includes, either directly or indirectly, an enzyme. ELISA tests may be formatted for direct, indirect, competitive, or sandwich detection of the analyte. Other methods rely on labels such as, for example, radioisotopes ($I^{125}$) or fluorescence. Additional techniques include, for example, agglutination, nephelometry, turbidimetry, Western blot, immunoprecipitation, immunocytochemistry, immunohistochemistry, flow cytometry, Luminex assay, and others (see ImmunoAssay: A Practical Guide, edited by Brian Law, published by Taylor & Francis, Ltd., 2005 edition).

Exemplary assay formats include enzyme-linked immunosorbent assay (ELISA), radioimmunoassay, fluorescent, chemiluminescence, and fluorescence resonance energy transfer (FRET) or time resolved-FRET (TR-FRET) immunoassays. Examples of procedures for detecting biomarkers include biomarker immunoprecipitation followed by quantitative methods that allow size and peptide level discrimination, such as gel electrophoresis, capillary electrophoresis, planar electrochromatography, and the like.

Methods of detecting and/or quantifying a detectable label or signal generating material depend on the nature of the label. The products of reactions catalyzed by appropriate enzymes (where the detectable label is an enzyme; see above) can be, without limitation, fluorescent, luminescent, or radioactive or they may absorb visible or ultraviolet light. Examples of detectors suitable for detecting such detectable labels include, without limitation, x-ray film, radioactivity counters, scintillation counters, spectrophotometers, colorimeters, fluorometers, luminometers, and densitometers.

Any of the methods for detection can be performed in any format that allows for any suitable preparation, processing, and analysis of the reactions. This can be, for example, in multi-well assay plates (e.g., 96 wells or 384 wells) or using any suitable array or microarray. Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting a detectable label.

Determination of Biomarker Values Using Gene Expression Profiling

Measuring mRNA in a biological sample may be used as a surrogate for detection of the level of the corresponding protein in the biological sample. Thus, any of the biomarkers or biomarker panels described herein can also be detected by detecting the appropriate RNA.

mRNA expression levels are measured by reverse transcription quantitative polymerase chain reaction (RT-PCR followed with qPCR). RT-PCR is used to create a cDNA from the mRNA. The cDNA may be used in a qPCR assay to produce fluorescence as the DNA amplification process progresses. By comparison to a standard curve, qPCR can produce an absolute measurement such as number of copies of mRNA per cell. Northern blots, microarrays, Invader assays, and RT-PCR combined with capillary electrophoresis have all been used to measure expression levels of mRNA in a sample. See Gene Expression Profiling: Methods and Protocols, Richard A. Shimkets, editor, Humana Press, 2004.

miRNA molecules are small RNAs that are non-coding but may regulate gene expression. Any of the methods suited to the measurement of mRNA expression levels can also be used for the corresponding miRNA. Recently many laboratories have investigated the use of miRNAs as biomarkers for disease. Many diseases involve wide spread transcriptional regulation, and it is not surprising that miRNAs might find a role as biomarkers. The connection between miRNA concentrations and disease is often even less clear than the connections between protein levels and disease, yet the value of miRNA biomarkers might be substantial. Of course, as with any RNA expressed differentially during disease, the problems facing the development of an in vitro diagnostic product will include the requirement that the miRNAs survive in the diseased cell and are easily extracted for analysis, or that the miRNAs are released into blood or other matrices where they must survive long enough to be measured. Protein biomarkers have similar requirements, although many potential protein biomarkers are secreted intentionally at the site of pathology and function, during disease, in a paracrine fashion. Many potential protein biomarkers are designed to function outside the cells within which those proteins are synthesized.

Detection of Biomarkers Using In Vivo Molecular Imaging Technologies

Any of the described biomarkers (see Tables 1, 2, 4, 5 and 8 to 12 may also be used in molecular imaging tests. For example, an imaging agent can be coupled to any of the described biomarkers, which can be used to aid in TB diagnosis, prognosis, to monitor disease progression, to monitor for disease recurrence, or to monitor response to therapy, among other uses.

In vivo imaging technologies provide non-invasive methods for determining the state of a particular disease in the body of an individual. For example, entire portions of the body, or even the entire body, may be viewed as a three dimensional image, thereby providing valuable information concerning morphology and structures in the body. Such technologies may be combined with the detection of the biomarkers described herein to provide information concerning TB status, in particular the TB status, of an individual.

The use of in vivo molecular imaging technologies is expanding due to various advances in technology. These advances include the development of new contrast agents or labels, such as radiolabels and/or fluorescent labels, which can provide strong signals within the body; and the development of powerful new imaging technology, which can detect and analyze these signals from outside the body, with sufficient sensitivity and accuracy to provide useful information. The contrast agent can be visualized in an appropriate imaging system, thereby providing an image of the portion or portions of the body in which the contrast agent is located. The contrast agent may be bound to or associated with a capture reagent, such as an aptamer or an antibody, for example, and/or with a peptide or protein, or an oligonucleotide (for example, for the detection of gene expression), or a complex containing any of these with one or more macromolecules and/or other particulate forms.

The contrast agent may also feature a radioactive atom that is useful in imaging. Suitable radioactive atoms include technetium-99m or iodine-123 for scintigraphic studies. Other readily detectable moieties include, for example, spin labels for magnetic resonance imaging (MRI) such as, for example, iodine-123 again, iodine-131, indium-111, fluorine-19, carbon-13, nitrogen-15, oxygen-17, gadolinium, manganese or iron. Such labels are well known in the art and could easily be selected by one of ordinary skill in the art.

Standard imaging techniques include but are not limited to magnetic resonance imaging, contrast-enhanced abdominal or transvaginal ultrasound, computed tomography (CT) scanning, positron emission tomography (PET), single photon emission computed tomography (SPECT), and the like. For diagnostic in vivo imaging, the type of detection instrument available is a major factor in selecting a given contrast agent, such as a given radionuclide and the particular biomarker that it is used to target (protein, mRNA, and the like). The radionuclide chosen typically has a type of decay that is detectable by a given type of instrument. In addition, when selecting a radionuclide for in vivo diagnosis, its half-life should be long enough to enable detection at the time of maximum uptake by the target tissue but short enough that deleterious radiation of the host is minimized.

Exemplary imaging techniques include but are not limited to PET and SPECT, which are imaging techniques in which a radionuclide is synthetically or locally administered to an individual. The subsequent uptake of the radiotracer is measured over time and used to obtain information about the targeted tissue and the biomarker. Because of the high-energy (gamma-ray) emissions of the specific isotopes employed and the sensitivity and sophistication of the instruments used to detect them, the two-dimensional distribution of radioactivity may be inferred from outside of the body.

Commonly used positron-emitting nuclides in PET include, for example, carbon-11, nitrogen-13, oxygen-15, and fluorine-18. Isotopes that decay by electron capture and/or gamma-emission are used in SPECT and include, for example iodine-123 and technetium-99m. An exemplary method for labeling amino acids with technetium-99m is the reduction of pertechnetate ion in the presence of a chelating precursor to form the labile technetium-99m-precursor complex, which, in turn, reacts with the metal binding group of a bifunctionally modified chemotactic peptide to form a technetium-99m-chemotactic peptide conjugate.

Antibodies are frequently used for such in vivo imaging diagnostic methods. The preparation and use of antibodies for in vivo diagnosis is well known in the art. Labeled antibodies which specifically bind any of the biomarkers in Tables 2 and 8 to 12 can be injected into an individual suspected of having a certain type of disease (e.g., TB), detectable according to the particular biomarker used, for the purpose of diagnosing or evaluating the disease status of the individual. The label used will be selected in accordance with the imaging modality to be used, as previously described. The amount of label within an organ or tissue also allows determination of the presence or absence of disease in that organ or tissue.

Similarly, aptamers may be used for such in vivo imaging diagnostic methods. For example, an aptamer that was used to identify a particular biomarker described in Tables 2 and 8 to 12 (and therefore binds specifically to that particular biomarker) may be appropriately labeled and injected into an individual suspected of having TB, detectable according to the particular biomarker, for the purpose of diagnosing or evaluating the TB status of the individual. The label used will be selected in accordance with the imaging modality to be used, as previously described. The amount of label within an organ or tissue also allows determination of the presence or absence of TB in that organ or tissue. Aptamer-directed imaging agents could have unique and advantageous characteristics relating to tissue penetration, tissue distribution, kinetics, elimination, potency, and selectivity as compared to other imaging agents.

Such techniques may also optionally be performed with labeled oligonucleotides, for example, for detection of gene expression through imaging with antisense oligonucleotides. These methods are used for in situ hybridization, for example, with fluorescent molecules or radionuclides as the label. Other methods for detection of gene expression include, for example, detection of the activity of a reporter gene.

Another general type of imaging technology is optical imaging, in which fluorescent signals within the subject are detected by an optical device that is external to the subject. These signals may be due to actual fluorescence and/or to bioluminescence. Improvements in the sensitivity of optical detection devices have increased the usefulness of optical imaging for in vivo diagnostic assays.

The use of in vivo molecular biomarker imaging is increasing, including for clinical trials, for example, to more rapidly measure clinical efficacy in trials for new disease therapies and/or to avoid prolonged treatment with a placebo for those diseases, such as multiple sclerosis, in which such prolonged treatment may be considered to be ethically questionable.

For a review of other techniques, see N. Blow, Nature Methods, 6, 465-469, 2009.

Determination of Biomarker Values Using Histology or Cytology Methods

For evaluation of TB, a variety of tissue and fluid body samples may be used in histological or cytological methods. Sample selection depends on the location of the disease and sample availability. For example, sputum collection, fine needle aspirates, cutting needles, core biopsies and resected, sampled or biopsied infected fluids or tissue can be used for histology. Any of the biomarkers identified herein that were shown to be up-regulated in the individuals with TB EVD can be used to stain a histological specimen as an indication of disease.

In one embodiment, one or more capture reagents specific to the corresponding biomarker is used in a cytological evaluation of a TB sample and may include one or more of the following: collecting a sputum or other body fluid or tissue cell sample, fixing the cell sample, dehydrating, clearing, immobilizing the cell sample on a microscope slide, permeabilizing the cell sample, treating for analyte retrieval, staining, destaining, washing, blocking, and reacting with one or more capture reagent/s in a buffered solution. In another embodiment, the cell sample is produced from a cell block.

In another embodiment, one or more capture reagents specific to the corresponding biomarker is used in a histological evaluation of a TB tissue sample and may include one or more of the following: collecting a tissue specimen, fixing the tissue sample, dehydrating, clearing, immobilizing the tissue sample on a microscope slide, permeabilizing the tissue sample, treating for analyte retrieval, staining, destaining, washing, blocking, rehydrating, and reacting with capture reagent/s in a buffered solution. In another embodiment, fixing and dehydrating are replaced with freezing.

In another embodiment, the one or more aptamers specific to the corresponding biomarker is reacted with the histological or cytological sample and can serve as the nucleic acid target in a nucleic acid amplification method. Suitable nucleic acid amplification methods include, for example, PCR, q-beta replicase, rolling circle amplification, strand displacement, helicase dependent amplification, loop mediated isothermal amplification, ligase chain reaction, and restriction and circularization aided rolling circle amplification.

In one embodiment, the one or more capture reagent/s specific to the corresponding biomarkers for use in the histological or cytological evaluation are mixed in a buffered solution that can include any of the following: blocking materials, competitors, detergents, stabilizers, carrier nucleic acid, polyanionic materials, etc.

A "cytology protocol" generally includes sample collection, sample fixation, sample immobilization, and staining. "Cell preparation" can include several processing steps after sample collection, including the use of one or more slow off-rate aptamers for the staining of the prepared cells.

Sample collection can include directly placing the sample in an untreated transport container, placing the sample in a transport container containing some type of media, or placing the sample directly onto a slide (immobilization) without any treatment or fixation.

Sample immobilization can be improved by applying a portion of the collected specimen to a glass slide that is treated with polylysine, gelatin, or a silane. Slides can be prepared by smearing a thin and even layer of cells across the slide. Care is generally taken to minimize mechanical distortion and drying artifacts. Liquid specimens can be processed in a cell block method. Alternatively, liquid specimens can be mixed 1:1 with the fixative solution for about ten minutes at room temperature.

Cell blocks can be prepared from residual effusions, sputum, urine sediments, gastrointestinal fluids, cell scraping, ascites, or fine needle aspirates. Cells are concentrated or packed by centrifugation or membrane filtration. A number of methods for cell block preparation have been developed. Representative procedures include the fixed sediment, bacterial agar, or membrane filtration methods. In the fixed sediment method, the cell sediment is mixed with a fixative like Bouins, picric acid, or buffered formalin and then the mixture is centrifuged to pellet the fixed cells. The supernatant is removed, drying the cell pellet as completely as possible. The pellet is collected and wrapped in lens paper and then placed in a tissue cassette. The tissue cassette is placed in a jar with additional fixative and processed as a tissue sample. Agar method is very similar but the pellet is removed and dried on paper towel and then cut in half. The cut side is placed in a drop of melted agar on a glass slide and then the pellet is covered with agar making sure that no bubbles form in the agar. The agar is allowed to harden and then any excess agar is trimmed away. This is placed in a tissue cassette and the tissue process completed. Alternatively, the pellet may be directly suspended in 2% liquid agar at 65° C. and the sample centrifuged. The agar cell pellet is allowed to solidify for an hour at 4° C. The solid agar may be removed from the centrifuge tube and sliced in half. The agar is wrapped in filter paper and then the tissue cassette. Processing from this point forward is as described above. Centrifugation can be replaced in any these procedures with membrane filtration. Any of these processes may be used to generate a "cell block sample."

Cell blocks can be prepared using specialized resin including Lowicryl resins, LR White, LR Gold, Unicryl, and MonoStep. These resins have low viscosity and can be polymerized at low temperatures and with ultra violet (UV) light. The embedding process relies on progressively cooling the sample during dehydration, transferring the sample to the resin, and polymerizing a block at the final low temperature at the appropriate UV wavelength.

Cell block sections can be stained with hematoxylin-eosin for cytomorphological examination while additional sections are used for examination for specific markers.

Whether the process is cytological or histological, the sample may be fixed prior to additional processing to prevent sample degradation. This process is called "fixation" and describes a wide range of materials and procedures that may be used interchangeably. The sample fixation protocol and reagents are best selected empirically based on the targets to be detected and the specific cell/tissue type to be analyzed. Sample fixation relies on reagents such as ethanol, polyethylene glycol, methanol, formalin, or isopropanol. The samples should be fixed as soon after collection and affixation to the slide as possible. However, the fixative selected can introduce structural changes into various molecular targets making their subsequent detection more difficult. The fixation and immobilization processes and their sequence can modify the appearance of the cell and these changes must be anticipated and recognized by the cytotechnologist. Fixatives can cause shrinkage of certain cell types and cause the cytoplasm to appear granular or reticular. Many fixatives function by crosslinking cellular components. This can damage or modify specific epitopes, generate new epitopes, cause molecular associations, and reduce membrane permeability. Formalin fixation is one of the most common cytological and histological approaches. Formalin forms methyl bridges between neighboring proteins or within proteins. Precipitation or coagulation is also used for fixation and ethanol is frequently used in this type of fixation. A combination of crosslinking and precipitation can also be used for fixation. A strong fixation process is best at preserving morphological information while a weaker fixation process is best for the preservation of molecular. However, given that virulent *Mycobacterium tuberculosis* is a biosafety level 3 organism any processing that has risk of aerosol generation should be assured of decontamination efficiency to prevent inadvertent exposures to laboratory personnel.

A representative fixative is 50% absolute ethanol, 2 mM polyethylene glycol (PEG), 1.85% formaldehyde. Variations on this formulation include ethanol (50% to 95%), methanol (20%-50%), and formalin (formaldehyde) only. Another common fixative is 2% PEG 1500, 50% ethanol, and 3% methanol. Slides are placed in the fixative for about 10 to 15 minutes at room temperature and then removed and allowed to dry. Once slides are fixed they can be rinsed with a buffered solution like PBS.

A wide range of dyes can be used to differentially highlight and contrast or "stain" cellular, sub-cellular, and tissue features or morphological structures. Hematoylin is used to stain nuclei a blue or black color. Orange G-6 and Eosin Azure both stain the cell's cytoplasm. Orange G stains keratin and glycogen containing cells yellow. Eosin Y is used to stain nucleoli, cilia, red blood cells, and superficial epithelial squamous cells. Romanowsky stains are used for air dried slides and are useful in enhancing pleomorphism and distinguishing extracellular from intracytoplasmic material.

The staining process can include a treatment to increase the permeability of the cells to the stain. Treatment of the cells with a detergent can be used to increase permeability. To increase cell and tissue permeability, fixed samples can be further treated with solvents, saponins, or non-ionic detergents. Enzymatic digestion can also improve the accessibility of specific targets in a tissue sample.

After staining, the sample is dehydrated using a succession of alcohol rinses with increasing alcohol concentration. The final wash is done with xylene or a xylene substitute, such as a citrus terpene, that has a refractive index close to that of the coverslip to be applied to the slide. This final step is referred to as clearing. Once the sample is dehydrated and cleared, a mounting medium is applied. The mounting medium is selected to have a refractive index close to the glass and is capable of bonding the coverslip to the slide. It will also inhibit the additional drying, shrinking, or fading of the cell sample.

Regardless of the stains or processing used, the final evaluation of the renal cytological specimen is made by some type of microscopy to permit a visual inspection of the morphology and a determination of the marker's presence or absence. Exemplary microscopic methods include brightfield, phase contrast, fluorescence, and differential interference contrast.

If secondary tests are required on the sample after examination, the coverslip may be removed and the slide destained. Destaining involves using the original solvent systems used in staining the slide originally without the added dye and in a reverse order to the original staining procedure. Destaining may also be completed by soaking the slide in an acid alcohol until the cells are colorless. Once colorless the slides are rinsed well in a water bath and the second staining procedure applied.

In addition, specific molecular differentiation may be possible in conjunction with the cellular morphological analysis through the use of specific molecular reagents such as antibodies or nucleic acid probes or aptamers. This improves the accuracy of diagnostic cytology. Micro-dissection can be used to isolate a subset of cells for additional evaluation, in particular, for genetic evaluation of abnormal chromosomes, gene expression, or mutations.

Preparation of a tissue sample for histological evaluation involves disinfection, fixation, dehydration, infiltration, embedding, and sectioning. The fixation reagents used in histology are very similar or identical to those used in cytology and have the same issues of preserving morphological features at the expense of molecular ones such as individual proteins. Time can be saved if the tissue sample is not fixed and dehydrated but instead is frozen and then sectioned while frozen. This is a more gentle processing procedure and can preserve more individual markers. However, freezing is not acceptable for long term storage of a tissue sample as subcellular information is lost due to the introduction of ice crystals. Ice in the frozen tissue sample also prevents the sectioning process from producing a very thin slice and thus some microscopic resolution and imaging of subcellular structures can be lost. In addition to formalin fixation, osmium tetroxide is used to fix and stain phospholipids (membranes).

Dehydration of tissues or sputum or other fluid is accomplished with successive washes of increasing alcohol concentration. Clearing employs a material that is miscible with alcohol and the embedding material and involves a stepwise process starting at 50:50 alcohol clearing reagent and then 100% clearing agent (xylene or xylene substitute). Infiltration involves incubating the tissue with a liquid form of the embedding agent (warm wax, nitrocellulose solution) first at 50:50 embedding agent: clearing agent and the 100% embedding agent. Embedding is completed by placing the tissue in a mold or cassette and filling with melted embedding agent such as wax, agar, or gelatin. The embedding agent is allowed to harden. The hardened tissue sample may then be sliced into thin section for staining and subsequent examination.

Prior to staining, the tissue section is dewaxed and rehydrated. Xylene is used to dewax the section, one or more changes of xylene may be used, and the tissue is rehydrated by successive washes in alcohol of decreasing concentration. Prior to dewax, the tissue section may be heat immobilized to a glass slide at about 80° C. for about 20 minutes.

Laser capture micro-dissection allows the isolation of a subset of cells for further analysis from a tissue section.

As in cytology, to enhance the visualization of the microscopic features, the tissue section or block or slice can be stained with a variety of stains. A large menu of commercially available stains can be used to enhance or identify specific features.

To further increase the interaction of molecular reagents with cytological or histological samples, a number of techniques for "analyte retrieval" have been developed. The first such technique uses high temperature heating of a fixed sample. This method is also referred to as heat-induced epitope retrieval or HIER. A variety of heating techniques have been used, including steam heating, microwaving, autoclaving, water baths, and pressure cooking or a combination of these methods of heating. Analyte retrieval solutions include, for example, water, citrate, and normal saline buffers. The key to analyte retrieval is the time at high temperature but lower temperatures for longer times have also been successfully used. Another key to analyte retrieval is the pH of the heating solution. Low pH has been found to provide the best immunostaining but also gives rise to backgrounds that frequently require the use of a second tissue section as a negative control. The most consistent benefit (increased immunostaining without increase in background) is generally obtained with a high pH solution regardless of the buffer composition. The analyte retrieval process for a specific target is empirically optimized for the target using heat, time, pH, and buffer composition as variables for process optimization. Using the microwave analyte retrieval method allows for sequential staining of different targets with antibody reagents. However, the time required to achieve antibody and enzyme complexes between staining steps has also been shown to degrade cell membrane analytes. Microwave heating methods have improved in situ hybridization methods as well.

To initiate the analyte retrieval process, the section is first dewaxed and hydrated. The slide is then placed in 10 mM sodium citrate buffer pH 6.0 in a dish or jar. A representative procedure uses an 1100 W microwave and microwaves the slide at 100% power for 2 minutes followed by microwaving the slides using 20% power for 18 minutes after checking to be sure the slide remains covered in liquid. The slide is then allowed to cool in the uncovered container and then rinsed with distilled water. HIER may be used in combination with an enzymatic digestion to improve the reactivity of the target to immunochemical reagents.

One such enzymatic digestion protocol uses proteinase K. A 20 µg/ml concentration of proteinase K is prepared in 50 mM Tris Base, 1 mM EDTA, 0.5% Triton X-100, pH 8.0 buffer. The process first involves dewaxing sections in 2 changes of xylene, 5 minutes each. Then the sample is hydrated in 2 changes of 100% ethanol for 3 minutes each, 95% and 80% ethanol for 1 minute each, and then rinsed in distilled water. Sections are covered with Proteinase K working solution and incubated 10-20 minutes at 37° C. in humidified chamber (optimal incubation time may vary depending on tissue type and degree of fixation). The sections are cooled at room temperature for 10 minutes and then rinsed in PBS Tween 20 for 2×2 min. If desired, sections can be blocked to eliminate potential interference from endogenous compounds and enzymes. The section is then incubated with primary antibody at appropriate dilution in primary antibody dilution buffer for 1 hour at room temperature or overnight at 4° C. The section is then rinsed with PBS Tween 20 for 2×2 min. Additional blocking can be performed, if required for the specific application, followed by additional rinsing with PBS Tween 20 for 3×2 min and then finally the immunostaining protocol completed.

A simple treatment with 1% SDS at room temperature has also been demonstrated to improve immunohistochemical staining. Analyte retrieval methods have been applied to slide mounted sections as well as free floating sections. Another treatment option is to place the slide in a jar containing citric acid and 0.1 Nonident P40 at pH 6.0 and heating to 95° C. The slide is then washed with a buffer solution like PBS.

For immunological staining of tissues it may be useful to block non-specific association of the antibody with tissue proteins by soaking the section in a protein solution like serum or non-fat dry milk.

Blocking reactions may include the need to do any of the following, either alone or in combination: reduce the level of endogenous biotin; eliminate endogenous charge effects; inactivate endogenous nucleases; and inactivate endogenous enzymes like peroxidase and alkaline phosphatase. Endogenous nucleases may be inactivated by degradation with proteinase K, by heat treatment, use of a chelating agent such as EDTA or EGTA, the introduction of carrier DNA or RNA, treatment with a chaotrope such as urea, thiourea, guanidine hydrochloride, guanidine thiocyanate, lithium perchlorate, etc., or diethyl pyrocarbonate. Alkaline phosphatase may be inactivated by treatment with 0.1N HCl for 5 minutes at room temperature or treatment with 1 mM levamisole. Peroxidase activity may be eliminated by treatment with 0.03% hydrogen peroxide. Endogenous biotin may be blocked by soaking the slide or section in an avidin (streptavidin, neutravidin may be substituted) solution for at least 15 minutes at room temperature. The slide or section is then washed for at least 10 minutes in buffer. This may be repeated at least three times. Then the slide or section is soaked in a biotin solution for 10 minutes. This may be repeated at least three times with a fresh biotin solution each time. The buffer wash procedure is repeated. Blocking protocols should be minimized to prevent damaging either the cell or tissue structure or the target or targets of interest but one or more of these protocols could be combined to "block" a slide or section prior to reaction with one or more slow off-rate aptamers. See Basic Medical Histology: the Biology of Cells, Tissues and Organs, authored by Richard G. Kessel, Oxford University Press, 1998.

Determination of Biomarker Values Using Mass Spectrometry Methods

A variety of configurations of mass spectrometers can be used to detect biomarker values. Several types of mass spectrometers are available or can be produced with various configurations. In general, a mass spectrometer has the following major components: a sample inlet, an ion source, a mass analyzer, a detector, a vacuum system, and instrument-control system, and a data system. Differences in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nanospray and microspray or matrix-assisted laser desorption. Common mass analyzers include a quadrupole mass filter, ion trap mass analyzer and time-of-flight mass analyzer. Additional mass spectrometry methods are well known in the art (see Burlingame et al. (1998) Anal. Chem. 70:647 R-716R; Kinter and Sherman, New York (2000)).

Protein biomarkers and biomarker values can be detected and measured by any of the following: electrospray ionization mass spectrometry (ESI-MS), ESI-MS/MS, ESI-MS/(MS)n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), tandem time-of-flight (TOF/TOF) technology, called ultraflex III TOF/TOF, atmospheric pressure chemical ionization mass spectrometry (APCI-MS), APCI-MS/MS, APCI-$(MS)^N$, atmospheric pressure photoionization mass spectrometry (APPI-MS), APPI-MS/MS, and APPI-$(MS)^N$, quadrupole mass spectrometry, Fourier transform mass spectrometry (FTMS), quantitative mass spectrometry, and ion trap mass spectrometry.

Sample preparation strategies are used to label and enrich samples before mass spectroscopic characterization of protein biomarkers and determination biomarker values. Labeling methods include but are not limited to isobaric tag for relative and absolute quantitation (iTRAQ) and stable isotope labeling with amino acids in cell culture (SILAC). Capture reagents used to selectively enrich samples for candidate biomarker proteins prior to mass spectroscopic analysis include but are not limited to aptamers, antibodies, nucleic acid probes, chimeras, small molecules, an F(ab')$_2$ fragment, a single chain antibody fragment, an Fv fragment, a single chain Fv fragment, a nucleic acid, a lectin, a ligand-binding receptor, affybodies, nanobodies, ankyrins, domain antibodies, alternative antibody scaffolds (e.g. diabodies etc.) imprinted polymers, avimers, peptidomimetics, peptoids, peptide nucleic acids, threose nucleic acid, a hormone receptor, a cytokine receptor, and synthetic receptors, and modifications and fragments of these.

Determination of Biomarker Values Using a Proximity Ligation Assay

A proximity ligation assay can be used to determine biomarker values. Briefly, a test sample is contacted with a pair of affinity probes that may be a pair of antibodies or a pair of aptamers, with each member of the pair extended with an oligonucleotide. The targets for the pair of affinity probes may be two distinct determinates on one protein or one determinate on each of two different proteins, which may exist as homo- or hetero-multimeric complexes. When probes bind to the target determinates, the free ends of the oligonucleotide extensions are brought into sufficiently close proximity to hybridize together. The hybridization of the oligonucleotide extensions is facilitated by a common connector oligonucleotide, which serves to bridge together the oligonucleotide extensions when they are positioned in sufficient proximity. Once the oligonucleotide extensions of the probes are hybridized, the ends of the extensions are joined together by enzymatic DNA ligation.

Each oligonucleotide extension comprises a primer site for PCR amplification. Once the oligonucleotide extensions are ligated together, the oligonucleotides form a continuous DNA sequence, which, through PCR amplification, reveals information regarding the identity and amount of the target protein as well as information regarding protein-protein interactions where the target determinates are on two different proteins. Proximity ligation can provide a highly sensitive and specific assay for real-time protein concentration and interaction information through use of real-time PCR. Probes that do not bind the determinates of interest do not have the corresponding oligonucleotide extensions brought into proximity and no ligation or PCR amplification can proceed, resulting in no signal being produced.

Aptamer Based Assay

The SomaLogic proteomics technology is an aptamer based assay, which may include the use of aptamers with improved binding properties (also referred to as slow off-rate aptamers), due to long dissociation rates (>30 minutes) and the incorporation of modified nucleotides that lead to unparalleled affinity of these reagents compared to standard RNA or DNA aptamers. Slow off-rate aptamers are typically made from single-stranded DNA (ssDNA) that may contain pyrimidine residues modified at their 5-position to mimic amino acid side-chains. The affinity of these aptamers for their targets is a consequence of the three-dimensional shape and these side chain modifications rather than the nucleotide sequence.

Slow off-rate aptamers are selected in vitro by the SELEX process (as described in detail above). To date, there are >1,000 slow off-rate aptamers developed to bind to human proteins. Regarding their use in diagnostic applications, aptamers, including slow off-rate aptamers, have several advantages over antibodies used for ELISAs, including better performance (affinity, accuracy), higher multiplexing capabilities (low cross-reactivity, identical assay conditions), chemical stability (heat, drying, denaturation), ease and reproducibility of reagent manufacturing, and lower cost (fully synthetic).

The current version of the aptamer based assay described herein measures quantitatively approximately 1,030 human proteins simultaneously using only 8 µL of sample (serum, plasma, CSF, blood, urine, sputum, lavage or tissue lysate). The small sample volume reflects the high sensitivity of the assay (hybridization to an array and fluorescence scanning), however, the actual sample volume at the front end is not limited, and larger samples (e.g., 0.5 ml serum) can be used. The assay can include an affinity column to enrich for pathogen analytes and pathogens themselves. Such enrichment procedures have been successfully performed with bead-immobilized, target-specific aptamers to concentrate samples (e.g. from 0.5 ml to <50 µL) to detect very low abundance biomarkers.

Using this assay, serum is currently tested at three different concentrations (5%, 0.3%, 0.01%). These serum dilutions are used simply for practical reasons to obtain accurate measurements for low-, medium-, and high-abundant proteins, respectively. For the quantitative determination of analytes in serum the data points should lay well within the linear range of the assay and between the lower limit of quantitation (LLOQ) and upper limit of quantitation (ULOQ). Dilution of serum may be advisable for the most abundant proteins where the linear range of the assay is typically between 0.003% and 0.1% of serum, and a plateau of the signal is reached at serum concentrations of 1% or above.

In contrast, low abundance proteins are measured more accurately and are easier to detect in less diluted serum. While the assay works perfectly to measure nearly all low abundance human proteins tested to date in 5% serum, such a 20-fold dilution of serum is not required for the assay. In fact, the assay performs well in 50% serum, resulting in a several-fold increased signal compared to the signal in 5% serum. Together, the use of larger sample sizes and less diluted serum will further improve the sensitivity of detection of extremely low abundance proteins such as may be the case for *Mycobacterium tuberculosis* (Mtb) (pathogen-derived) markers.

Slow off-rate aptamers have an average sensitivity of 100 fM, and the aptamer based assay has a dynamic range of >5 logs, and a median coefficient of variation (% CV) of 5% for individual proteins measured repeatedly in replicate runs of serum and plasma sample. Performance data are available for all of the more than 1,000 slow off-rate aptamers, including measured signal in standard curves obtained by spiking purified protein into buffer and precision profiles showing the % CV over the concentration range between the LLOQ and ULOQ.

The sensitivity of the aptamers is excellent and not adversely affected by multiplexing for over a thousand analytes in a single assay. The median LLOQ is 300 fM, which is 6 pg/mL for a small, 20 kDa protein. The limit of detection (LOD) for each aptamer correlates well with its affinity ($K_d$) for its target. Over the past several years, the affinities ($K_d$'s) of aptamers have improved by several orders of magnitude. Compared to standard DNA or RNA aptamers with $K_d$'s in the high nanomolar range, slow off-rate aptamers have typical $K_d$'s in the picomolar range. Such high affinity aptamers result in low femtomolar LODs in the assay. The concentration of Mtb pathogen markers in blood is largely unknown; antigen 85 levels in sputum are in the 100 pg/ml range, which is 3 pM and thus well within the sensitivity of the assay. Moreover, the affinity of the reagents can often be further increased by incorporating of alternate 5-position modified nucleotides into the aptamers. The utility of this assay has been demonstrated in oncology, cardiovascular, kidney, neurological and infectious diseases (Ostroff et al. (2010) PloS one 5:e15003).

This aptamer based assay is a powerful tool to identify and then validate serum proteomic signatures typical for the medical condition of interest. Once a subset of biomarkers has been identified, a corresponding "small-plex" aptamer panel can be assembled (that is, a panel consisting of a few analytes). The aptamer assay is easily adapted to multiple formats and platforms besides hybridization to a slide-array, including standard clinical laboratory assays (e.g., Luminex), but also very simple sandwich-type assays with beads, plates, or membranes, and a variety of signal enhancing and detection methods can be used. The latter methods are well suited for point-of-care applications. The envisioned aptamer-based TB test will not require staining, or expensive equipment typically needed for molecular amplification assays. It also has the potential for independence from electricity for refrigeration of reagents or the need for powering detection devices. These comparative advantages of the diagnostic reagents and proteomics platform are encouraging toward the development of a simple, rapid, and inexpensive TB test that can have a very favorable impact on this global health problem.

The foregoing assays enable the detection of biomarker values that are useful in methods for evaluating or diagnosing TB, where the methods comprise detecting, in a biological sample from an individual, at least N biomarker values that each correspond to a biomarker selected from the group consisting of the biomarkers provided in Tables 2 and 8 to 12, wherein a classification, as described in detail below, using the biomarker values indicates whether the individual has TB EVD. While certain of the described TB biomarkers are useful alone for detecting, evaluating and diagnosing TB, methods are also described herein for the grouping of multiple subsets of the TB biomarkers that are each useful as a panel of two, three, four or more biomarkers. In accordance with any of the methods described herein, biomarker values can be detected and classified individually or they can be detected and classified collectively, as for example in a multiplex assay format.

In another aspect, methods are provided for detecting an absence of TB, the methods comprising detecting, in a biological sample from an individual, at least N biomarker values that each correspond to a biomarker selected from the group consisting of the biomarkers provided in Tables 2 and 8 to 12, wherein a classification, as described in detail below, of the biomarker values indicates an absence of TB in the individual. In accordance with any of the methods described herein, biomarker values can be detected and classified individually or they can be detected and classified collectively, as for example in a multiplex assay format.

Classification of Biomarkers and Calculation of TB Prognosis Scores

A biomarker "signature" for a given evaluation test contains a set of markers, each marker having different levels in the populations of interest. Different levels, in this context, may refer to different means of the marker levels for the individuals in two or more groups, or different variances in the two or more groups, or a combination of both. For the simplest form of an evaluation test, these markers can be used to assign an unknown sample from an individual into one of two groups, either diseased or not diseased. The assignment of a sample into one of two or more groups is known as classification, and the procedure used to accomplish this assignment is known as a classifier or a classification method. Classification methods may also be referred to as scoring methods. There are many classification methods that can be used to construct an evaluation classifier from a set of biomarker values. In general, classification methods are most easily performed using supervised learning techniques where a data set is collected using samples obtained from individuals within two (or more, for multiple classification states) distinct groups one wishes to distinguish. Since the class (group or population) to which each sample belongs is known in advance for each sample, the classification method can be trained to give the desired classification response. It is also possible to use unsupervised learning techniques to produce a prognostic classifier.

Common approaches for developing evaluation classifiers include decision trees; bagging+boosting+forests; rule inference based learning; Parzen Windows; linear models; logistic; neural network methods; unsupervised clustering; K-means; hierarchical ascending/descending; semi-supervised learning; prototype methods; nearest neighbor; kernel density estimation; support vector machines; hidden Markov models; Boltzmann Learning; and classifiers may be combined either simply or in ways which minimize particular objective functions. For a review, see, e.g., Pattern Classification, R. O. Duda, et al., editors, John Wiley & Sons, 2nd edition, 2001; see also, The Elements of Statistical Learning—Data Mining, Inference, and Prediction, T. Hastie, et al., editors, Springer Science+Business Media, LLC, 2nd edition, 2009; each of which is incorporated by reference in its entirety.

To produce a classifier using supervised learning techniques, a set of samples called training data are obtained. In the context of prognostic tests, training data includes samples from the distinct groups (classes) to which unknown samples will later be assigned. For example, samples collected from individuals in a control population and individuals in a particular disease population can constitute training data to develop a classifier that can classify unknown samples (or, more particularly, the individuals from whom the samples were obtained) as either having the disease or being free from the disease. The development of the classifier from the training data is known as training the classifier. Specific details on classifier training depend on the nature of the supervised learning technique. For purposes of illustration, an example of training a random forest classifier will be described below (see, e.g., Pattern Classification, R. O. Duda, et al., editors, John Wiley & Sons, 2nd edition, 2001; see also, The Elements of Statistical Learning—Data Mining, Inference, and Prediction, T. Hastie, et al., editors, Springer Science+Business Media, LLC, 2nd edition, 2009).

Since typically there are many more potential biomarker values than samples in a training set, care must be used to avoid over-fitting. Over-fitting occurs when a statistical model describes random error or noise instead of the underlying relationship. Over-fitting can be avoided in a variety of ways, including, for example, by limiting the number of markers used in developing the classifier, by assuming that the marker responses are independent of one another, by limiting the complexity of the underlying statistical model employed, and by ensuring that the underlying statistical model conforms to the data.

An illustrative example of the development of an evaluation test using a set of biomarkers includes the application of a random forest classifier (Shi and Horvath (2006) Unsupervised Learning with Random Forest Predictors. (March 2006) Journal of Computational and Graphical Statistics 15(1):118-138). A RF predictor is an ensemble of individual classification tree predictors (Breiman (2001) Machine Learning 45(1):5-32). For each observation, each individual tree votes for one class and the forest predicts the class that has the plurality of votes. The user has to specify the number of randomly selected variables to be searched through for the best split at each node. The Gini index (Breiman et al. (1984), Classification and Regression Trees, Chapman and Hall, New York.) is used as the splitting criterion. The largest tree possible is grown and is not pruned. The root node of each tree in the forest contains a bootstrap sample from the original data as the training set. The observations that are not in the training set, roughly 1=3 of the original data set, are referred to as out-of-bag (OOB) observations. One can arrive at OOB predictions as follows: for a case in the original data, predict the outcome by plurality vote involving only those trees that did not contain the case in their corresponding bootstrap sample. By contrasting these OOB predictions with the training set outcomes, one can arrive at an estimate of the prediction error rate, which is referred to as the OOB error rate.

Each biomarker is described by a class-dependent probability density function (pdf) for the measured RFU values or log RFU (relative fluorescence units) values in each class. The joint pdfs for the set of markers in one class is assumed to be the product of the individual class-dependent pdfs for each biomarker. Any underlying model for the class-dependent pdfs may be used, but the model should generally conform to the data observed in the training set.

The performance of the random forest classifier is dependent upon the number and quality of the biomarkers used to construct and train the classifier. A single biomarker will perform in accordance with its KS-distance (Kolmogorov-Smirnov) and its PCA value as exemplified herein. If a classifier performance metric is defined as the sum of the sensitivity (fraction of true positives, $f_{TP}$) and specificity (one minus the fraction of false positives, $1-f_{FP}$), a perfect classifier will have a score of two and a random classifier, on average, will have a score of one. Using the definition of the KS-distance, that value x* which maximizes the difference in the cdf functions can be found by solving $$\frac{\partial KS}{\partial x} = \frac{\partial (cdf_c(x) - cdf_d(x))}{\partial x} = 0$$

for x, which leads to p(x*|c)=p(x*|d), i.e., the KS distance occurs where the class-dependent pdfs cross. Substituting this value of x* into the expression for the KS-distance yields the following definition for KS $$KS = cdf_c(x^*) - cdf_d(x^*) = \int_{-\infty}^{x^*} p(x|c)dx - \int_{-\infty}^{x^*} p(x|d)dx =$$
$$1 - \int_{x^*}^{\infty} p(x|c)dx - \int_{-\infty}^{x^*} p(x|d)dx = 1 - f_{FP} - f_{FN},$$

the KS distance is one minus the total fraction of errors using a test with a cut-off at x*, essentially a single analyte Bayesian classifier. Since we define a score of sensitivity+specificity=$2-f_{FP}-f_{FN}$, combining the above definition of the KS-distance we see that sensitivity+specificity=1+KS. We select biomarkers with a statistic that is inherently suited for building classifiers.

The addition of subsequent markers with good KS distances (>0.3, for example) will, in general, improve the classification performance if the subsequently added markers are independent of the first marker. Using the sensitivity plus specificity as a classifier score, it is straightforward to generate many high scoring classifiers.

Another way to identify relevant biomarkers is through Principal Components Analysis (PCA). PCA is a method that reduces data dimensionality by performing a covariance analysis between factors. As such, it is suitable for data sets in multiple dimensions, such as a large experiment in protein or gene expression. PCA uses an orthogonal transformation to convert a set of observations of possibly correlated variables into a set of values of uncorrelated variables called principal components. It is used as a tool in exploratory data analysis and for making predictive models. The central idea of principal component analysis (PCA) is to reduce the dimensionality of a data set consisting of a large number of interrelated variables, while retaining as much as possible of the variation present in the data set. This is achieved by transforming to a new set of variables, the principal components (PCs), which are uncorrelated, and which are ordered so that the first few retain most of the variation present in all of the original variables (Joliffe I T. (2002) Principal Component Analysis, $2^{nd}$ Edition. Springer).

Another way to depict classifier performance is through a receiver operating characteristic (ROC), or simply ROC curve. The ROC is a graphical plot of the sensitivity, or true positive rate, vs. false positive rate (1-specificity or 1-true negative rate), for a binary classifier system as its discrimination threshold is varied. The ROC can also be represented equivalently by plotting the fraction of true positives out of the positives (TPR=true positive rate) vs. the fraction of false positives out of the negatives (FPR=false positive rate). This is also known as a Relative Operating Characteristic curve, because it is a comparison of two operating characteristics (TPR & FPR) as the criterion changes. The area under the ROC curve (AUC) is commonly used as a summary measure of diagnostic accuracy. It can take values from 0.0 to 1.0. The AUC has an important statistical property: the AUC of a classifier is equivalent to the probability that the classifier will rank a randomly chosen positive instance higher than a randomly chosen negative instance (Fawcett T (2006) Pattern Recognition Letters 27:861-874). This is equivalent to the Wilcoxon test of ranks (Hanley and McNeil (1982) Radiology 143:29-36).

The algorithm approach used here is exemplified herein. Briefly, all single analyte classifiers are generated from a table of potential biomarkers and added to a list. Next, all possible additions of a second analyte to each of the stored single analyte classifiers is then performed, saving a predetermined number of the best scoring pairs, say, for example, a thousand, on a new list. All possible three-marker classifiers are explored using this new list of the best two-marker classifiers, again saving the best thousand of these. This process continues until the score either plateaus or begins to deteriorate as additional markers are added. Those high scoring classifiers that remain after convergence can be evaluated for the desired performance for an intended use. For example, in one prognostic application, classifiers with a high sensitivity and modest specificity may be more desirable than modest sensitivity and high specificity. In another prognostic application, classifiers with a high specificity and a modest sensitivity may be more desirable. The desired level of performance is generally selected based upon a trade-off that must be made between the number of false positives and false negatives that can each be tolerated for the particular prognostic application. Such trade-offs generally depend on the medical consequences of an error, either false positive or false negative.

Various other techniques are known in the art and may be employed to generate many potential classifiers from a list of biomarkers using a random forest classifier. In one embodiment, what is referred to as a genetic algorithm can be used to combine different markers using the fitness score as defined above. Genetic algorithms are particularly well suited to exploring a large diverse population of potential classifiers. In another embodiment, so-called ant colony optimization can be used to generate sets of classifiers. Other strategies that are known in the art can also be employed, including, for example, other evolutionary strategies as well as simulated annealing and other stochastic search methods. Metaheuristic methods, such as, for example, harmony search may also be employed.

The markers listed in Tables 1, 2, 4, 5, and 8 to 12 can be combined in many ways to produce classifiers for evaluating and diagnosing TB. In some embodiments, panels of biomarkers are comprised of different numbers of analytes depending on a specific diagnostic performance criterion that is selected. For example, certain combinations of biomarkers will produce tests that are more sensitive (or more specific) than other combinations.

Once a panel is defined to include a particular set of biomarkers from Tables 2 and 8 to 12 and a classifier is constructed from a set of training data, the definition of the diagnostic test is complete. The biological sample is appropriately diluted and then run in one or more assays to produce the relevant quantitative biomarker levels used for classification. The measured biomarker levels are used as input for the classification method that outputs a classification and an optional score for the sample that reflects the confidence of the class assignment.

Tables 8 to 12 identify 122 biomarkers that are useful for evaluating TB treatment effect. We put forth any combination of these markers (with the TB specific markers) as putative diagnostic signatures of TB disease. This is a surprisingly larger number than expected when compared to what is typically found during biomarker discovery efforts and may be attributable to the scale of the described study, which encompassed over 1030 proteins measured in hundreds of individual samples, in some cases at concentrations in the low femtomolar range. Presumably, the large number of discovered biomarkers reflects the diverse biochemical pathways implicated in both TB biology and the body's response to the presence of TB and its subsequent treatment or response of the body to the drugs; each pathway and process involves many proteins. The results show that no single protein of a small group of proteins is uniquely informative about such complex processes; rather, that multiple proteins are involved in relevant processes, such as inflammation, coagulation cascade, tissue remodeling, antimicrobial protein functions, apoptosis or extracellular matrix turn over and repair or fibrosis scarring and healing for example.

Given the number of biomarkers identified during the described study, one would expect to be able to derive ample numbers of high-performing classifiers that can be used in various diagnostic methods. It was found that many subsets of the biomarkers presented in Tables 2 and 8 to 12 can be combined with each other or the TB specific markers to generate useful classifiers.

The results of classifier evaluation tests suggest certain possible conclusions: First, the identification of a large number of biomarkers enables their aggregation into a vast number of classifiers that offer similarly high performance. Second, classifiers can be constructed such that particular biomarkers may be substituted for other biomarkers in a manner that reflects the redundancies that undoubtedly pervade the complexities of the underlying disease processes. That is to say, the information about the disease contributed by any individual biomarker identified in Tables 2 and 8 to 12 overlaps with the information contributed by other biomarkers, such that it may be that no particular biomarker or small group of biomarkers in Tables 2 and 8 to 12 must be included in any classifier.

Exemplary embodiments use random forest classifiers constructed from the data in Tables 2 and 8 to 12 to classify an unknown sample. In one embodiment, the biological sample is optionally diluted and run in a multiplexed aptamer assay. The data from the assay are normalized and calibrated, and the resulting biomarker levels are used as input to a random forest classification scheme.

The general method for performing the aptamer based proteomic assay is set forth in Example 1. Example 2 describes the targeted proteomic assay employed to identify and quantify protein markers that were associated with active TB and that changed in response to four-drug treatment. With reference to Example 2, it can be seen that the healing process that accompanies effective anti-TB therapy appears to be highly associated with a fibrotic healing process and is in keeping with radiographic changes known to occur with TB therapy. Among the diverse pathways identified, the most predominant were those representing the core biological themes of antimicrobial defenses and tissue remodeling/healing functions.

Biomarkers of Inflammation and Anti-Microbial Defense

Differentially expressed proteins involved in innate and adaptive immunity to which antimicrobial function has been attributed were identified. Some of the proteins identified include, but are not limited to, complement cascade components, CRP, $\alpha$-1 antitrypsin (AAT), hepcidin (LEAP), bactericidal permeability increasing protein (BPI), lipopolysaccharide binding protein (LBP) and phospholipase A2 (NPS-PLA2), all of which decreased over time in the majority of patients. C9 and C3 breakdown products (C3b and C3d) decreased with therapy in the majority of the patients. Components of the MTB bacillus are known to induce the antimicrobial molecule hepcidin (LEAP) which has been reported to have both iron handling and antibacterial properties. The finding of NPS-PLA2 as a top marker distinguishing week 8 samples from baseline samples highlights the importance of this protein, which has both antibacterial and lipolytic functions in the host. NPS-PLA2 is an innate immune antibacterial molecule involved in arachidonic acid and fatty acid generation and may be involved in the lipoid pneumonia seen with pulmonary TB. Cathepsin G, an antimicrobial molecule and serine protease found in hypoxic TB granulomas decreased on therapy in the majority of patients. Mannose receptor C type 2 (MRC-2), another pattern recognition molecule known to be involved in TB and activating the innate immune system was among the top 3 markers that were differentially expressed between baseline and 8 weeks.

Biomarkers of Tissue Remodeling

A number of proteins involved in tissue healing including proteases and anti-proteases, fibrotic process proteins, remodeling of collagen and extracellular matrix (ECM), as well as, members of the coagulation cascade were also identified. Plasminogen, a marker found in all analyses, has been reported to be co-opted by MTB and other respiratory pathogens in order to evade immune responses. Once activated, plasminogen is converted to plasmin, a serine protease that can degrade fibrin and activate complement. Plasmin has also been reported to increase the activity of many proteins including matrix metalloproteinases (MMP) and TGF-$\beta$ which can alter host pathology and allow the tubercle bacillus to disseminate more readily. Thrombospondin-4 (TSP4) prominently appears in both the paired and unpaired analysis. The thrombospondins are a family of extracellular matrix glycoproteins that mediate cell-to-cell and cell-to-matrix interactions. They are reportedly involved in lung adhesion, fibrosis, neovascularization and cardiac tissue re-modeling, but to date it is believed that they have not been associated with active TB. Fibroblast activation protein (SEPR) is also involved in collagen and extracellular matrix degradation. Additional MMPs and their endogenous inhibitors, tissue inhibitors of metalloproteinases (TIMPs) are both classes of enzymes involved in fibrosis and the proper formation of granulomatous inflammation, tissue remodeling and turnover of extracellular matrix material in normal and pathological conditions. The differential expression of these proteins may relate to drug toxicity, underlying cavitary disease, resolution of liquefaction and ultimate healing with fibrosis.

Biomarkers of Angiogenesis and Coagulation

Angiogenesis is a complex biological phenomenon controlled by both positive and negative signals. The finding of three forms of vascular endothelial growth factor (VEGF) or its receptor among the top markers changing over time supports an intriguing role for angiogenesis and vascular remodeling and has recently been shown by others to be associated with TB. Significant changes in levels of proteins members (e.g. antithrombin III) of the coagulation cascades were found, highlighting the importance of such cascades in the course of TB. There is a pro-coagulant state in TB and others have shown that hematologic/coagulation factors can be biomarkers of TB infection. Indeed careful study of lung histopathology of human and experimental MTB infection reveals areas of vasculitis and microthrombi within vessels contributing to lesion formation.

Biomarkers Associated with Disease Severity

When considering markers associated with the severity of disease a few proteins are worthy of specific comment. The levels of thrombospondin-2 (TSP-2), a protein regulating a variety of cell-matrix interactions was found to be higher in those with more cavitary manifestations of disease. Three additional markers stood out in a logistic regression analysis of disease severity: DKK-1, serum amyloid P and adiponectin. DKK-1 an inhibitor of wnt signaling has also been shown to alter fibrosis and expression is up-regulated in a *Chlamydia* infection model. Serum amyloid P is a member (as is CRP) of the pentraxin family of proteins involved in pattern recognition and complement activation and levels have been shown to correlate with disease severity and rapidity of burn wound healing. Adiponectin is associated with metabolic syndrome and insulin resistance and is known to be increased with decreased body fat so the finding of low levels with severe disease would argue against the association being attributed exclusively to low BMI in our patients. Adiponectin may be important in the lung, as receptors for this adipokine have been shown in the lung and low levels of adiponectin are associated with development of other serious pulmonary diseases (e.g. asthma). Some neurological and other markers identified may be related to drug toxicity.

With reference to Example 4, it can be seen that a number of proteins were identified that were differentially present between treatment of "slow-responders" (subjects that had yet to respond by week 8) and responders at baseline or after 8 weeks of TB treatment (Table 8). A "responder" as used herein refers to one who has negative sputum culture results on both solid and liquid culture media at week 8 and a "slow responder" refers to one who has a positive on one or both media types at week 8.

Serum amyloid A (SAA) protein was a strong predictor of treatment response in multiple analyses performed. Not unexpectedly, many proteins involved in innate and adaptive immunity were differentially expressed, including gp-130, TNF pathway molecules, complement components, catalase, IgG, IFN-k, PSME1, PSD7. At baseline, the strongest marker predicting treatment response was PSME1, an IFN-γ-inducible component of the immunoproteasome. The levels of this protein are known to be increased under the conditions of intensified immune response and are important for efficient antigen processing. IL-11 Ra is a receptor for IL-11 and uses the high affinity gp130 transducing domain, which also appeared in both the baseline and week 8 data, and both are acute phase response proteins. APRIL is a TNF family ligand, can be involved in TGF-β signaling, and has been shown to have a role in the response to pathogens. Both TGF-β and TNF are important cytokines in TB. APRIL has also been shown to be involved in promoting T-cell proliferation and survival. MMP-12 and MMP-13 were differentially expressed at baseline. The major substrate for MMP-12 is elastin, a major protein of the lung connective tissue and it has been detected in lung disease. Matrix proteoglycan (BGN) and BGH3 may also be involved in extracellular matrix and tissue remodeling. The finding of elevated ECM1 in responders is intriguing but the strength of the association weakens somewhat when adjusted for age (data not shown). Proteins involved in amyloids/fibrils (BGH3) and potentially HSP70 deserve greater attention and may have to do with the makeup of the TB lesions and can change with therapy. XPNPEP1 is a metalloaminopeptidase involved in the degradation of neuropeptides and the finding of VIP in these analyses is intriguing for the role of neuropeptides in treatment of TB. The finding of coagulation factor V as the strongest marker at 8 weeks could suggest either better protein calorie nutrition in responders or that tissue remodeling, changes in fibrinolysis and resolution of pulmonary TB lesions has heretofore undescribed connections with the coagulation cascade.

We have built several mathematical models for the prediction of the 8 week culture status. One example is a logistic regression model using four features obtained during measurements of serum protein levels at baseline together with subject age. The model performed fairly accurately in sample classification and resulted in an ROC curve with AUC=0.96 (see FIG. 21D). Similar performance was observed for a model containing the top five serum protein markers at baseline based on KS distances (see FIG. 21). Separately, we also selected the top markers at 8 weeks based on large KS distances (0.5), and combined a five-feature signature (coagulation factor V, XPNPEP1, gp130, TIMP-2 and ECM1) in a naïve Bayes classifier to "predict" treatment response, which revealed an ROC curve with an AUC=0.88 (see FIG. 19A).

Correlation of serum protein measurements with time to culture corroborated some of the markers found in previous analyses and several other proteins linked to neutrophil function.

Kits

Any combination of the biomarkers of Tables 1, 2, 4, 5, and 8 to 12 (as well as additional biomedical information) can be detected using a suitable kit, such as for use in performing the methods disclosed herein. Furthermore, any kit can contain one or more detectable labels as described herein, such as a fluorescent moiety, etc.

In one embodiment, a kit includes (a) one or more capture reagents (such as, for example, at least one aptamer or antibody) for detecting one or more biomarkers in a biological sample, wherein the biomarkers include any of the biomarkers set forth in Tables 1, 2, 4, 5, and 8 to 12, and optionally (b) one or more software or computer program products for classifying the individual from whom the biological sample was obtained, for evaluation of TB status. Alternatively, rather than one or more computer program products, one or more instructions for manually performing the above steps by a human can be provided.

The combination of a solid support with a corresponding capture reagent and a signal generating material is referred to herein as a "detection device" or "kit". The kit can also include instructions for using the devices and reagents, handling the sample, and analyzing the data. Further the kit may be used with a computer system or software to analyze and report the result of the analysis of the biological sample.

The kits can also contain one or more reagents (e.g., solubilization buffers, detergents, washes, or buffers) for processing a biological sample. Any of the kits described herein can also include, e.g., buffers, blocking agents, mass spectrometry matrix materials, antibody capture agents, positive control samples, negative control samples, software and information such as protocols, guidance and reference data.

In one aspect, the invention provides kits for the analysis of TB status. The kits include PCR primers for one or more biomarkers selected from Tables 1, 2, 4, 5, and 8 to 12. The kit may further include instructions for use and correlation of the biomarkers with TB. The kit may also include any of the following, either alone or in combination: a DNA array containing the complement of one or more of the biomarkers selected from Tables 1, 2, 4, 5, and 8 to 12, reagents, and enzymes for amplifying or isolating sample DNA. The kits may include reagents for real-time PCR, such as, for example, TaqMan probes and/or primers, and enzymes.

For example, a kit can comprise: (a) reagents comprising at least capture reagents for quantifying one or more biomarkers in a test sample, wherein said biomarkers comprise the biomarkers set forth in Tables 1, 2, 4, 5, and 8 to 12, or any other biomarkers or biomarkers panels described herein; and optionally (b) one or more algorithms or computer programs for performing the steps of comparing the amount of each biomarker quantified in the test sample to one or more predetermined cutoffs and assigning a score for each biomarker quantified based on said comparison, combining the assigned scores for each biomarker quantified to obtain a total score, comparing the total score with a predetermined score, and using said comparison to evaluate TB status in an individual. Alternatively, rather than one or more algorithms or computer programs, one or more instructions for manually performing the above steps by a human can be provided.

Computer Methods and Software

Once a biomarker or biomarker panel is selected, a method for evaluating an individual for TB status can comprise the following: 1) collect or otherwise obtain a biological sample; 2) perform an analytical method to detect and measure the biomarker or biomarkers in the panel in the biological sample; 3) perform any data normalization or standardization required for the method used to collect biomarker values; 4) calculate the marker score; 5) combine the marker scores to obtain a total diagnostic score; and 6) report the individual's diagnostic score. In this approach, the diagnostic score may be a single number determined from the sum of all the marker calculations that is compared to a preset threshold value that is an indication of the presence or absence of disease. Or the diagnostic score may be a series of bars that each represent a biomarker value and the pattern of the responses may be compared to a pre-set pattern for determination of the presence or absence of disease.

Figure 3:
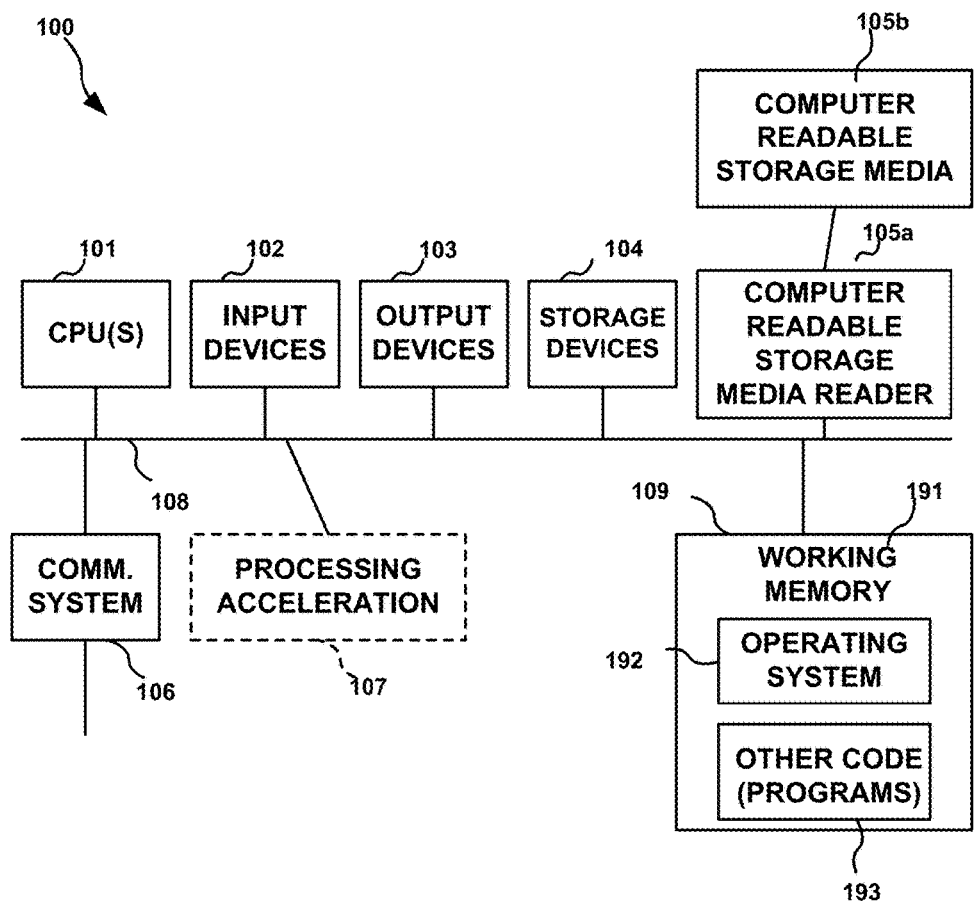

At least some embodiments of the methods described herein can be implemented with the use of a computer. An example of a computer system 100 is shown in FIG. 3. With reference to FIG. 3, system 100 is shown comprised of hardware elements that are electrically coupled via bus 108, including a processor 101, input device 102, output device 103, storage device 104, computer-readable storage media reader 105a, communications system 106 processing acceleration (e.g., DSP or special-purpose processors) 107 and memory 109. Computer-readable storage media reader 105a is further coupled to computer-readable storage media 105b, the combination comprehensively representing remote, local, fixed and/or removable storage devices plus storage media, memory, etc. for temporarily and/or more permanently containing computer-readable information, which can include storage device 104, memory 109 and/or any other such accessible system 100 resource. System 100 also comprises software elements (shown as being currently located within working memory 191) including an operating system 192 and other code 193, such as programs, data and the like.

With respect to FIG. 3, system 100 has extensive flexibility and configurability. Thus, for example, a single architecture might be utilized to implement one or more servers that can be further configured in accordance with currently desirable protocols, protocol variations, extensions, etc. However, it will be apparent to those skilled in the art that embodiments may well be utilized in accordance with more specific application requirements. For example, one or more system elements might be implemented as sub-elements within a system 100 component (e.g., within communications system 106). Customized hardware might also be utilized and/or particular elements might be implemented in hardware, software or both. Further, while connection to other computing devices such as network input/output devices (not shown) may be employed, it is to be understood that wired, wireless, modem, and/or other connection or connections to other computing devices might also be utilized.

In one aspect, the system can comprise a database containing features of biomarkers characteristic of TB. The biomarker data (or biomarker information) can be utilized as an input to the computer for use as part of a computer implemented method. The biomarker data can include the data as described herein.

In one aspect, the system further comprises one or more devices for providing input data to the one or more processors.

The system further comprises a memory for storing a data set of ranked data elements.

In another aspect, the device for providing input data comprises a detector for detecting the characteristic of the data element, e.g., such as a mass spectrometer or gene chip reader.

The system additionally may comprise a database management system. User requests or queries can be formatted in an appropriate language understood by the database management system that processes the query to extract the relevant information from the database of training sets.

The system may be connectable to a network to which a network server and one or more clients are connected. The network may be a local area network (LAN) or a wide area network (WAN), as is known in the art. Preferably, the server includes the hardware necessary for running computer program products (e.g., software) to access database data for processing user requests.

The system may include an operating system (e.g., UNIX or Linux) for executing instructions from a database management system. In one aspect, the operating system can operate on a global communications network, such as the internet, and utilize a global communications network server to connect to such a network.

The system may include one or more devices that comprise a graphical display interface comprising interface elements such as buttons, pull down menus, scroll bars, fields for entering text, and the like as are routinely found in graphical user interfaces known in the art. Requests entered on a user interface can be transmitted to an application program in the system for formatting to search for relevant information in one or more of the system databases. Requests or queries entered by a user may be constructed in any suitable database language.

The graphical user interface may be generated by a graphical user interface code as part of the operating system and can be used to input data and/or to display inputted data. The result of processed data can be displayed in the interface, printed on a printer in communication with the system, saved in a memory device, and/or transmitted over the network or can be provided in the form of the computer readable medium.

The system can be in communication with an input device for providing data regarding data elements to the system (e.g., expression values). In one aspect, the input device can include a gene expression profiling system including, e.g., a mass spectrometer, gene chip or array reader, and the like.

The methods and apparatus for analyzing TB biomarker information according to various embodiments may be implemented in any suitable manner, for example, using a computer program operating on a computer system. A conventional computer system comprising a processor and a random access memory, such as a remotely-accessible application server, network server, personal computer or workstation may be used. Additional computer system components may include memory devices or information storage systems, such as a mass storage system and a user interface, for example a conventional monitor, keyboard and tracking device. The computer system may be a stand-alone system or part of a network of computers including a server and one or more databases.

The TB biomarker analysis system can provide functions and operations to complete data analysis, such as data gathering, processing, analysis, reporting and/or diagnosis. For example, in one embodiment, the computer system can execute the computer program that may receive, store, search, analyze, and report information relating to the TB biomarkers. The computer program may comprise multiple modules performing various functions or operations, such as a processing module for processing raw data and generating supplemental data and an analysis module for analyzing raw data and supplemental data to generate a TB status and/or diagnosis. Evaluating TB status may comprise generating or collecting any other information, including additional biomedical information, regarding the condition of the individual relative to TB, identifying whether further tests may be desirable, or otherwise evaluating the health status of the individual.

Figure 4:
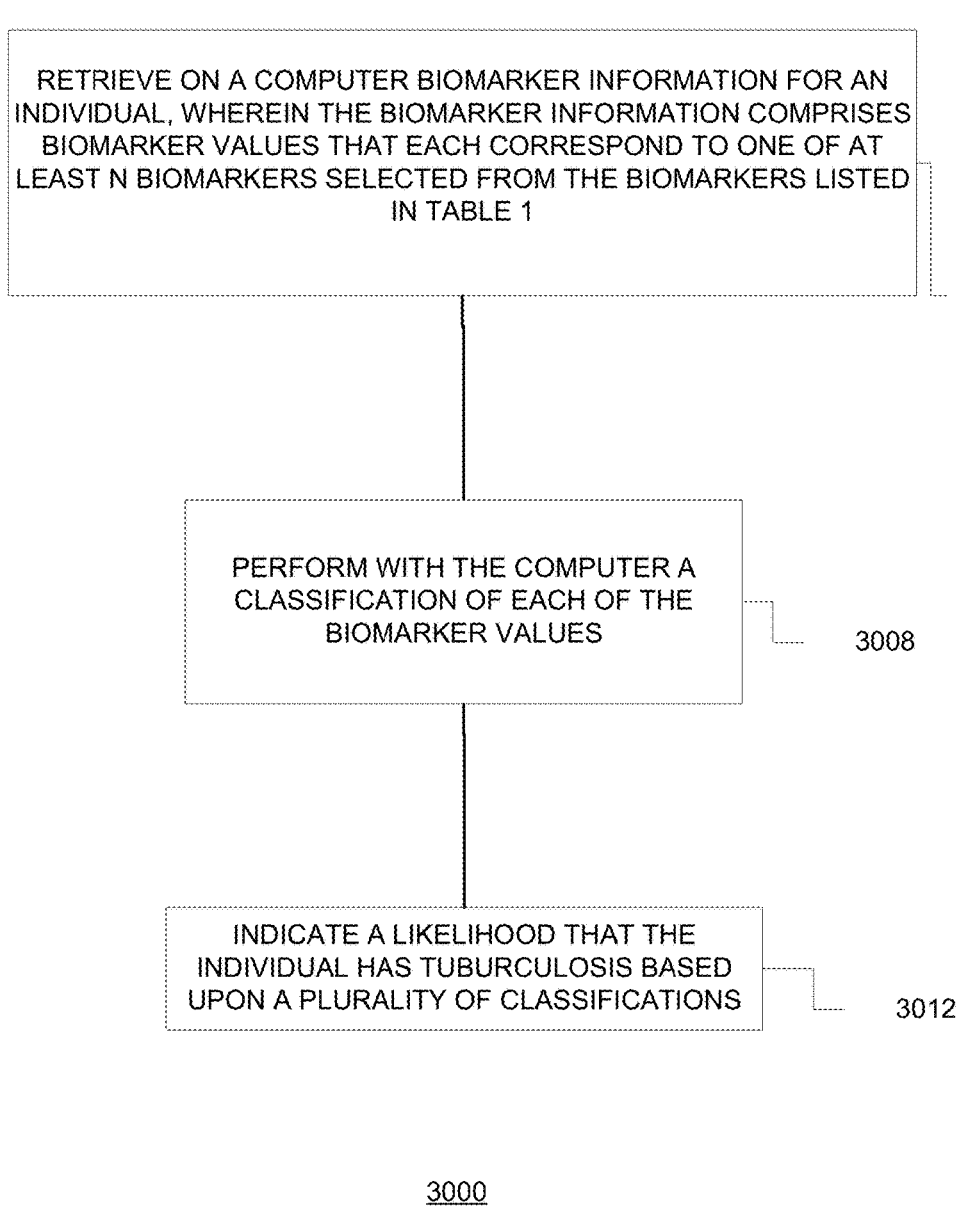
FIG. 4 is a flowchart 3000 for a method of indicating the likelihood that an individual has TB in accordance with one embodiment. In block 3004, biomarker information can be retrieved for an individual. In block 3008, a computer can be utilized to classify each of the biomarker values. In block 3012, an evaluation can be made regarding TB status based upon a plurality of classifications.

Referring now to FIG. 4, an example of a method of utilizing a computer in accordance with principles of a disclosed embodiment can be seen. In FIG. 4, a flowchart 3000 is shown. In block 3004, biomarker information can be retrieved for an individual. The biomarker information can be retrieved from a computer database, for example, after testing of the individual's biological sample is performed. The biomarker information can comprise biomarker values that each correspond to one of at least N biomarkers selected from a group consisting of the biomarkers provided in the biomarkers provided in Tables 1, 2, 4, 5, and 8 to 12. In block 3008, a computer can be utilized to classify each of the biomarker values. In block 3012, an evaluation can be made regarding TB status based upon a plurality of classifications. The indication can be output to a display or other indicating device so that it is viewable by a person. Thus, for example, it can be displayed on a display screen of a computer or other output device.

Referring now to FIG. 5, an alternative method of utilizing a computer in accordance with another embodiment can be illustrated via flowchart 3200. In block 3204, a computer can be utilized to retrieve biomarker information for an individual. The biomarker information comprises a biomarker value corresponding to a biomarker selected from the group of biomarkers provided in Tables 1, 2, 4, 5, and 8 to 12. In block 3208, a classification of the biomarker value can be performed with the computer. In block 3212, an indication can be made as to the TB status of the individual based upon the classification. The indication can be output to a display or other indicating device so that it is viewable by a person. Thus, for example, it can be displayed on a display screen of a computer or other output device.

Some embodiments described herein can be implemented so as to include a computer program product. A computer program product may include a computer readable medium having computer readable program code embodied in the medium for causing an application program to execute on a computer with a database.

As used herein, a "computer program product" refers to an organized set of instructions in the form of natural or programming language statements that are contained on a physical media of any nature (e.g., written, electronic, magnetic, optical or otherwise) and that may be used with a computer or other automated data processing system. Such programming language statements, when executed by a computer or data processing system, cause the computer or data processing system to act in accordance with the particular content of the statements. Computer program products include without limitation: programs in source and object code and/or test or data libraries embedded in a computer readable medium. Furthermore, the computer program product that enables a computer system or data processing equipment device to act in pre-selected ways may be provided in a number of forms, including, but not limited to, original source code, assembly code, object code, machine language, encrypted or compressed versions of the foregoing and any and all equivalents.

In one aspect, a computer program product is provided for evaluating TB status of an individual. The computer program product includes a computer readable medium embodying program code executable by a processor of a computing device or system, the program code comprising: code that retrieves data attributed to a biological sample from an individual, wherein the data comprises biomarker values that each correspond to one of at least N biomarkers in the biological sample selected from the group of biomarkers provided in Tables 1, 2, 4, 5, and 8 to 12; and code that executes a classification method that indicates TB status of the individual as a function of the biomarker values.

In still another aspect, a computer program product is provided for evaluating TB status. The computer program product includes a computer readable medium embodying program code executable by a processor of a computing device or system, the program code comprising: code that retrieves data attributed to a biological sample from an individual, wherein the data comprises a biomarker value corresponding to a biomarker in the biological sample selected from the group of biomarkers provided in Tables 1, 2, 4, 5, and 8 to 12; and code that executes a classification method that indicates a TB disease status of the individual as a function of the biomarker value.

While various embodiments have been described as methods or apparatuses, it should be understood that embodiments can be implemented through code coupled with a computer, e.g., code resident on a computer or accessible by the computer. For example, software and databases could be utilized to implement many of the methods discussed above. Thus, in addition to embodiments accomplished by hardware, it is also noted that these embodiments can be accomplished through the use of an article of manufacture comprised of a computer usable medium having a computer readable program code embodied therein, which causes the enablement of the functions disclosed in this description. Therefore, it is desired that embodiments also be considered protected by this patent in their program code means as well. Furthermore, the embodiments may be embodied as code stored in a computer-readable memory of virtually any kind including, without limitation, RAM, ROM, magnetic media, optical media, or magneto-optical media. Even more generally, the embodiments could be implemented in software, or in hardware, or any combination thereof including, but not limited to, software running on a general purpose processor, microcode, PLAs, or ASICs.

It is also envisioned that embodiments could be accomplished as computer signals embodied in a carrier wave, as well as signals (e.g., electrical and optical) propagated through a transmission medium. Thus, the various types of information discussed above could be formatted in a structure, such as a data structure, and transmitted as an electrical signal through a transmission medium or stored on a computer readable medium.

With reference to Example 2, it can be seen that a number of proteins were identified that were differentially present between treatment slow-responders and responders at baseline or after 8 weeks of TB treatment (Tables 1, 2, 4, 5, and 8 to 12). Certain themes revolving around inflammation, immunity, coagulation, tissue remodeling, liquefaction, fibrinolysis and tissue repair emerge. Not unexpectedly, many proteins involved in innate and adaptive immunity to which antimicrobial function has been attributed are differentially expressed (including but not limited to gp-130, TNF pathway molecules, complement components, catalase, IgG, IFN-k, PSME, PSD7 etc.). At baseline, the strongest marker predicting treatment response is PSME, an IFN-γ-inducible component of the immunoproteosome. The levels of this protein are known to be increased under the conditions of intensified immune response and are important for efficient antigen processing (Kohda et al. (1998) Journal of immunology 160:4923-4935).

It is also noted that many of the structures, materials, and acts recited herein can be recited as means for performing a function or step for performing a function. Therefore, it should be understood that such language is entitled to cover all such structures, materials, or acts disclosed within this specification and their equivalents, including the matter incorporated by reference.

EXAMPLES

The following examples are provided for illustrative purposes only and are not intended to limit the scope of the application as defined by the appended claims. All examples described herein were carried out using standard techniques, which are well known and routine to those of skill in the art. Routine molecular biology techniques described in the following examples can be carried out as described in standard laboratory manuals, such as Sambrook et al., Molecular Cloning: A Laboratory Manual, 3rd. ed., Cold Spring Harbor Laboratory Press, Cold Spring Harbor, N.Y., (2001).

Example 1. Arrays and Methods for Generating Results

The SomaLogic aptamer based proteomics discovery platform used in the studies presented herein quantitatively measures approximately 1030 proteins simultaneously using serum, plasma, CSF tissue lysate or blood from small sample volume that reflects the high sensitivity of the assay (hybridization to an array and fluorescence scanning) (Gold et al. (2010) PloS One 5:e15004). Over all 1030 proteins the median lower limit of quantitation is 0.3 pM, with a dynamic range of >5 logs, and a median coefficient of variation (% CV) of 5% (Ostroff et al. (2010) Journal of proteomics 73:649-666).

Figure 2:
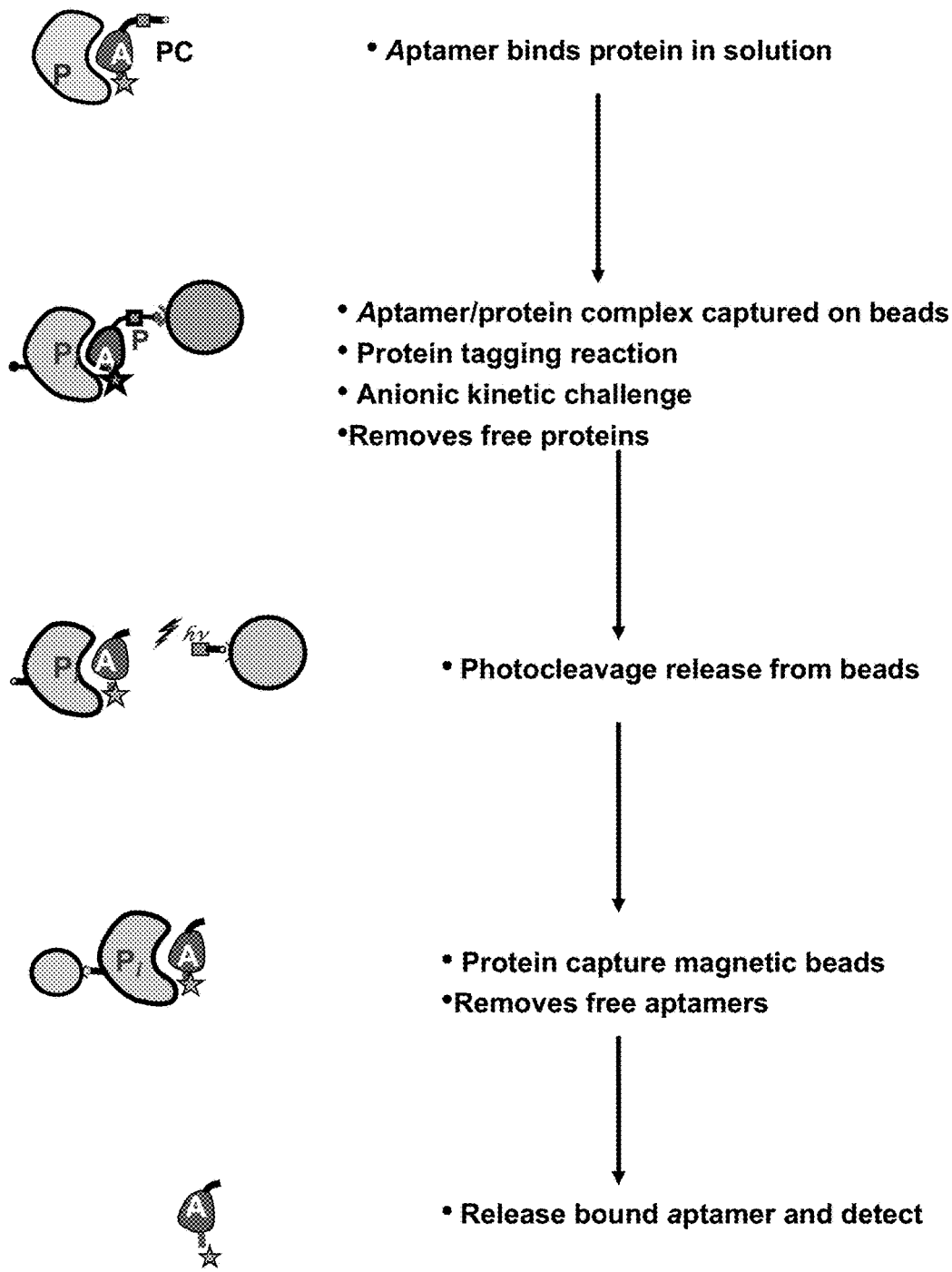
FIG. 2 illustrates an exemplary aptamer assay that can be used to detect one or more TB biomarkers in a biological sample.

The SomaLogic proteomics discovery platform is a multiplex proteomics assay, which measures proteins by transforming the quantity of a specific protein into an equivalent, or proportional, quantity of its cognate aptamer, which is captured in the assay and quantified by hybridization to a custom Agilent microarray (any DNA chip could be used). A full description of the processes and performance of slow off-rate aptamer reagents and the SomaLogic multiplex proteomics assay is described in Gold et al. (2010) PLoS One 5:e15004 (see FIG. 2).

Example 2. Study Design and Data Analysis

Study Population

Participants were enrolled from United States Centers for Disease Control Tuberculosis (TBTC) Study 29, a prospective, multicenter, open-label Phase 2B clinical trial (clinicaltrials.gov NCT00694629) comparing efficacy and safety of standard TB therapy comprised of rifampin, isoniazid, pyrazinamide and ethambutol with rifapentine replacing rifampin (Dorman et al. (2012) J Infect Dis 206:1030-40). The 39 participants included in this pilot project were all from the TBTC site based in Kampala, Uganda, were sputum smear positive and HIV-uninfected. Patient samples to be included in this study were selected to be free of significant co-morbidities reported at enrollment (December 2008 to July 2009), and had reasonably normal renal, hepatic and hematologic function. Ages of the 39 study participants ranged from 19 to 53 years, 28 were males, the average body mass index (BMI) was 19.3 kg/m$^2$, and 22 (56%) had cavitary disease, three of which had bilateral cavities.

| Participant Characteristics | Value (range) |
| --- | --- |
| # patients | 39 |
| Rifampin treated (%) | 14 (36) |
| Age years, median | 28.5 (19-53) |
| Male (%) | 28 (72) |
| BMI median, kg/m$^2$ | 19 (15.2-26.7) |
| Cavitary lesions (%) | 56 |
| Smoker (%) | 20 |
| Alcohol use (%) | 2 |

Participants completed between 6 and 24 months of anti-TB treatment. Follow-up through the end of treatment did not reveal any treatment failures. One participant had INH and RIF resistant tuberculosis; one participant had mono-drug resistance to INH and one had dual resistance (to streptomycin and rifampin), all were detected after the participants completed intensive phase treatment. Four participants received between 3-5 days of 4 drug, standard chemotherapy prior to enrollment.

Serum was collected, processed and stored at baseline (time of enrollment), and after 8 weeks (40 doses) of intensive phase therapy. Efficacy of the regimens was assessed through determination of sputum culture status on both Lowenstein-Jensen (LJ) solid media and BACTEC Mycobacterial Growth Indicator Tube (MGIT, Becton Dickinson and Co., Franklin Lakes, N.J.) liquid media with the MGIT 960 system. For this analysis, patients who were culture negative at completion of 8 weeks of treatment on both media types were classified as "responders", whereas those patients who remained culture positive on either (or both) of the culture media, were deemed "slow responders". IRB approval for TBTC Study 29 was obtained from all participating institutions and from the Centers for Disease Control and Prevention (CDC). Additionally, this pilot project was also approved by the Committee on Human Research of the University of California, San Francisco (H45279-34102-02A). Of the 39 participants, 25 patients had been randomly assigned to the rifapentine arm and 14 to the rifampin arm. Four patients received between 3-5 days of therapy prior to enrollment. By design half of the subjects selected for this analysis had responded to the treatment after eight weeks (8 week), as defined by culture status on LJ and MGIT liquid media. All 39 pairs of baseline and end of intensive phase treatment (8-week) serum samples, respectively, were included in the proteomic assay to measure 1030 proteins. Clinical, radiographic and microbiologic data were not received until after all proteomic measurements were completed and results had been submitted to the CDC. Additional information including total duration of treatment and end of treatment cure status was retrieved from patient charts by GM in Kampala, Uganda.

Proteomic Methods

Aptamers were selected in vitro by the SELEX process, which consists of multiple rounds of selection, partitioning, and amplification (Brody and Gold (2000) Journal of biotechnology 74:5-13; Gold, L. (1995) The Journal of biological chemistry 270:13581-13584). As detailed above, the success of SELEX and the affinity of the aptamers obtained has been greatly improved through the use of modified nucleotides to expand the chemistry of DNA for in vitro selection (Vaught et al. (2010) Journal of the American Chemical Society 132:4141-4151). To date, aptamers with excellent affinities (sub-nanomolar $K_d$'s) to >1,000 human serum proteins have been generated and are used in the highly multiplexed aptamer based assay described herein. Serum was tested at three different concentrations (5%, 0.3%, 0.01%) to obtain accurate measurements within the dynamic range of the assay for low-, medium-, and high-abundant proteins, respectively. The integrity of serum samples provided for testing was monitored for known sample handling artifacts (Ostroff et al. (2010) Journal of proteomics 73:649-666). The aptamer based proteomics assay is described in detail in Gold et al. ((2010) PloS one 5:e15004). In brief, the assay consists of equilibrium binding of fluorophore-tagged aptamers and proteins in plasma or serum in solution and automated partitioning steps to capture only the aptamers that are in complexes with their cognate proteins. In essence, the assay transforms the measurement of proteins into the measurement of the corresponding aptamers (DNA), via hybridization to an antisense probe array using a hybridization gasket slide with eight microarrays per slide (Agilent Technologies). The liquid handling steps of the assay (protein binding) were performed by a Biomek robot, and the fluorescent signal generated in the hybridization step is captured using a fluorescence slide scanner (Agilent Technologies). Protein concentrations are reported in relative fluorescence units (RFU).

Statistical Analysis

Matlab™ and the R environment for statistical computing were used for statistical analysis. Fisher's exact test was used to compare the proportions of radiographic findings in responders and non-responders. Linear regression analyses were used to assess the association between protein levels measured in log RFU and culture conversion times. The non-parametric Kolmogorov-Smirnov (KS) test was applied for unpaired comparisons of the protein distributions in rapid and slow-responders. The KS statistic is an unsigned quantity, though a "signed" value is reported to convey the directionality in the differential expression, that is, positive or negative KS distances for increased or decreased protein levels, respectively, in a given comparison of interest.

The Wilcoxon rank sum test was used to identify proteins with paired (within-subject) differential response between baseline and week 8 in the responders and slower responders respectively. Multiple comparison corrections were performed using the false discovery rate (FDR) methodology (Storey (2002) J Royal Stat Soc, Series B 64:479-498). For each statistic both p-values and the associated FDR corrected "q-values" computed with the R package q-value (Dabney et al. qvalue: Q-value estimation for false discovery rate control. R package version 1.26.0 2011 reported. The q-value is analogous to a p-value—it measures the statistical significance of a particular observation, but with respect to the expected number of false positives rather than the probability of a false positive. The database for annotation, visualization and integrated discovery (DAVID) analysis was used for functional clustering and annotation (DAVID Bioinformatics Resources 6.7; National Institute of Allergy and Infectious Diseases (NIAID), NIH (2003-2016); Huang et al. (2009) Nucleic acids research 37:1-13; Huang et al. (2009) Nature protocols 4:44-57; Jiao et al. (2012) Bioinformatics 28:1805-1806).

A regularized logistic regression model was used to select variables that distinguish responders from slow-responders. Stability selection using the randomized lasso (Meinshausen and Buhlmann (2006) The Annals of Statistics 34:1436-1462) was used to identify proteins with high selection probabilities over a wide range of regularization parameters. Selection probabilities were computed from 500 random partitions of the observations using the randomized lasso. One hundred random permutations of the "responder" and "slow-responder" labels were used to estimate the lower bound on the false discovery rate for stability selection. A final logistic regression model was re-fit (without regularization) to the markers with highest selection probability, and the resulting sensitivity and specificity when classifying subjects by treatment response was estimated using stratified cross-validation.

Sample Handling

SomaLogic Inc., (Boulder, Colo.) performed all proteomic assessments and was blinded to the clinical characteristics of participating patients from whom sera was obtained for this study. Affinity-based proteomic technology successfully measured 1,030 proteins from serum per subject, per time point. Samples were analyzed in a single assay run and data validation was performed using internal assay controls without a priori knowledge of time point, clinical or microbiological details. A small systematic difference (4%) in the overall protein concentrations between the baseline and 8 week sample sets was removed during normalization. Three samples had elevated hemoglobin levels and correspondingly low haptoglobin levels when compared both to other subjects and internal assay calibrators suggesting some degree of hemolysis. No other evidence of sample processing errors (Ostroff et al. (2010) Journal of Proteomics 73: 649-666) was observed so all samples were considered fit for inclusion in the subsequent data analysis.

Nonspecific Markers of Active TB

Figure 6A:
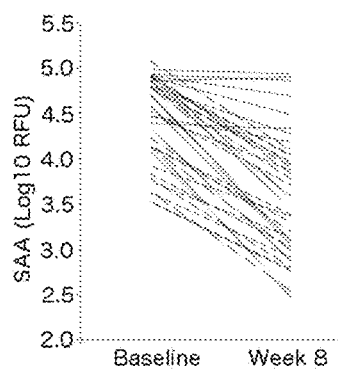
FIGS. 6A-6C illustrate changes in expression of non-specific markers for active TB, including acute phase reactants SAA (FIG. 6A) and CRP (FIG. 6B), and albumin (FIG. 6C), between baseline and week 8 of therapy. Each line represents an individual TB patient.
Figure 6B:
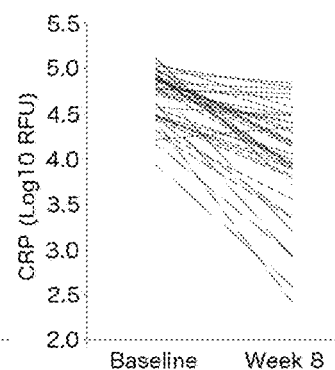
Figure 6C:
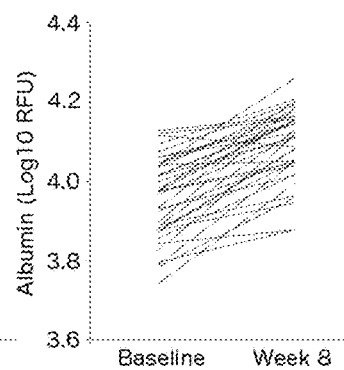

Serum protein concentrations in TB patients at baseline were compared to those measured in the same patients after 8 weeks of therapy. The acute phase reactants C-reactive protein (CRP) and serum amyloid A protein (SAA) decreased from baseline to week 8 in all but one subject (FIG. 6). Serum albumin increased between baseline and week 8 in all but one subject. Other known important acute phase reactants including haptoglobin, alpha-1 antitrypsin (AAT) and serum amyloid A protein declined from baseline to week 8 consistent with a reduction in the disease burden.

Correlations with Severity of Disease

Figure 7A:
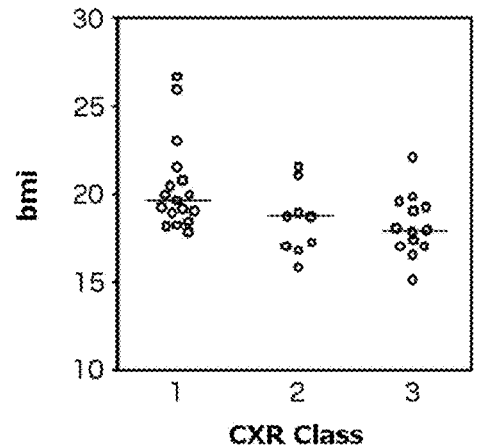
FIGS. 7A-7D illustrate association of clinical parameters (BMI, time to detection) and serum protein levels (plasminogen, thrombospondin-2) with radiographic classification of cavitation. Each circle represents an individual TB patient at baseline. CXR class 1=no cavitation; class 2=cavitation <4 cm in size; class 3=cavitation >4 cm in size.
Figure 7B:
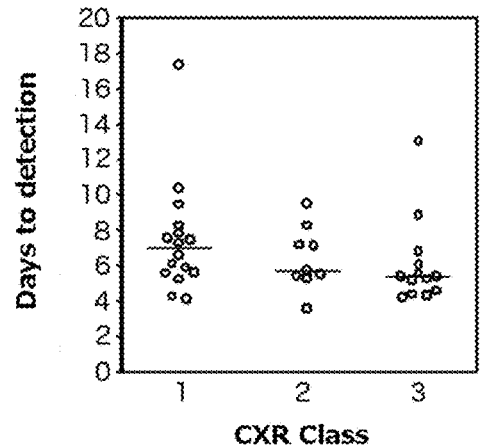
Figure 7C:
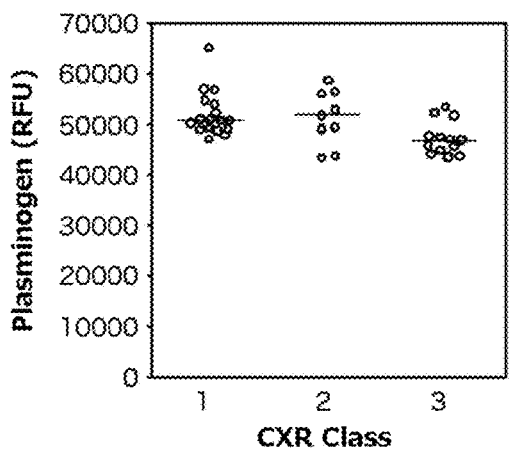
Figure 7D:
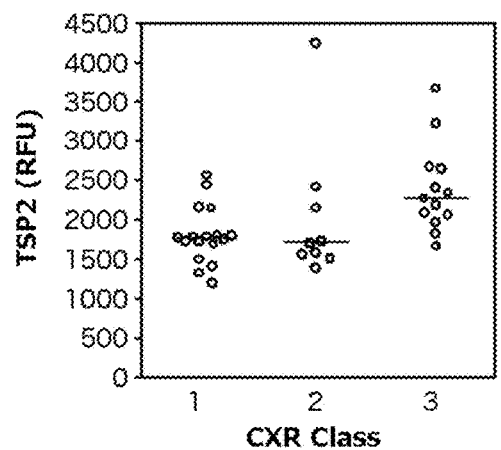

Microbiological and radiographic parameters are used to assess the severity of TB disease. At baseline, total cavitary volume and time-to-detection in MGIT culture are markers of severity of disease and bacillary burden in the sputum, respectively. Among the data available for the patients involved in this study, CXR class (as defined by presence cavitation and size on baseline CXR, class 1=no cavitation; class 2=cavitation present, <4 cm in size; class 3=cavitation present, >4 cm in size) showed the strongest association with other parameters such as body mass index (BMI, FIG. 7A) and time-to-detection in MGIT culture (TTD, FIG. 7B), and as expected, both were lower in the 13 patients with large and/or bilateral cavities (CXR class 3) compared to the 17 patients without cavitary disease (CXR class 1), but there was substantial overlap between groups. Plasminogen (FIG. 7C), which was lower in CXR class 3 compared to class 1 and thrombospondin-2 (TSP-2), which was higher in CXR class 3 compared to class 1 (FIG. 7D) best discriminate CXR class 1 from class 3 patients, though these effects had an 18% false discovery rate.

The top markers at baseline distinguishing the thirteen patients with more severe disease (score >0.60) and the thirteen patients with less severe disease (score <0.40) were CRP, SAA, and NPS-PLA2 with roughly two-fold increased levels of the median.

Figure 8A:
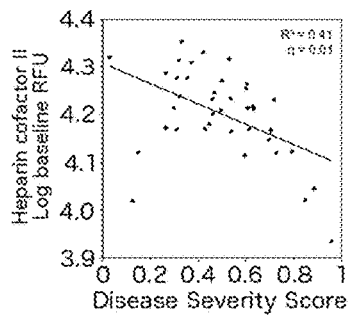
FIGS. 8A-8I depict correlation of serum protein markers with TB disease severity. Top markers showed the largest differential expression in mild disease (n=13) compared to severe disease (n=13), based on medians at baseline. Baseline (log) RFU was used as the response in a linear model and a 5% false discovery rate.
Figure 8B:
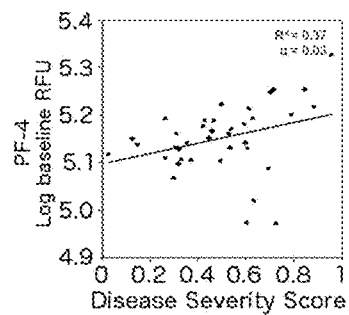
Figure 8C:
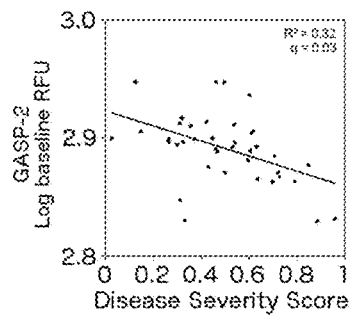
Figure 8D:
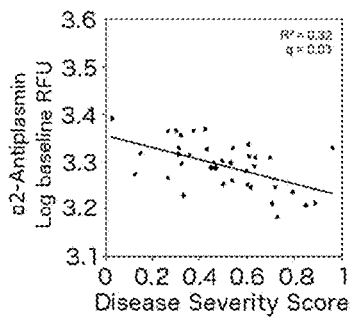
Figure 8E:
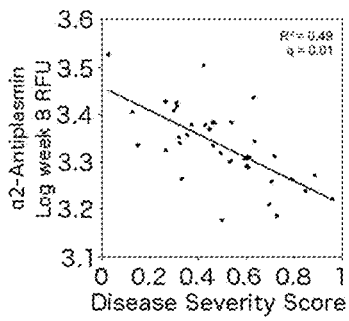
Figure 8F:
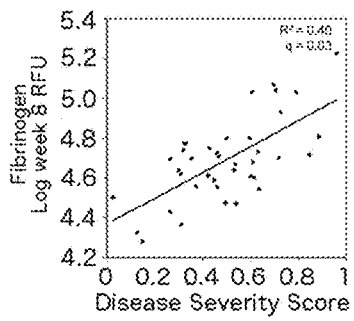
Figure 8G:
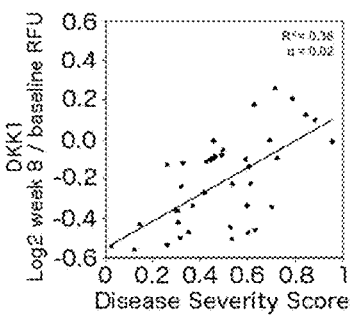
Figure 8H:
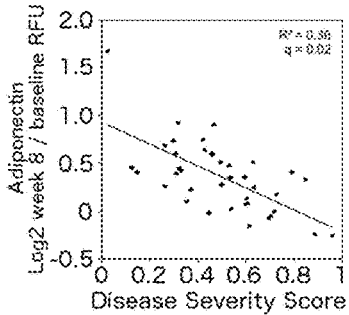
Figure 8I:
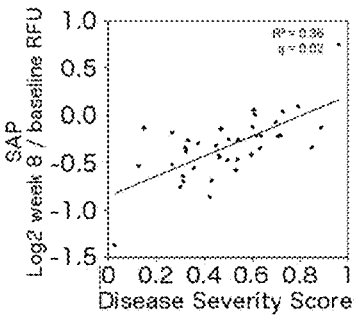

Regression analysis was used to identify proteins that changed with increasing disease severity measured. Using baseline (log) RFU as the response in a linear model and a 5% false discovery rate, Heparin cofactor 2, platelet factor-4 (PF-4), G-protein coupled receptor associated sorting protein-2 (GASP-2), and α2-antiplasmin had baseline concentrations that were correlated with our disease severity score (FIGS. 8A-D). Low levels of heparin cofactor 2 and GASP2 were both associated with more severe disease. Interestingly, α2-antiplasmin levels at 8 weeks also decreased with increasing severity scores (FIG. 8E). In contrast, fibrinogen levels measured at 8 weeks were higher in patients with severe disease (FIG. 8F). Regression analysis using the (log 2) ratio of week 8 to baseline concentration and a 5% false discovery rate uncovered additional proteins whose rate of change was associated with disease severity. The top markers were DKK-1, adiponectin and serum amyloid P component (SAP) (FIGS. 3G-I). DKK-1 levels decreased from baseline to 8 weeks in patients with mild disease, but remained high or even increased in patients with more severe disease. Adiponectin increased in the majority of patients with mild disease but remained unchanged in those with the highest disease severity score (data not shown).

Paired Analysis of Serum Proteins at Baseline Versus Week 8 of TB Therapy

At a 0.01% false discovery rate (q<0.0001), 239 of the 1,030 proteins measured were identified as differentially expressed between baseline and 8 weeks of treatment using the Wilcoxon Signed Rank test. Sixteen proteins shifted in the same direction from baseline to week 8 in all 39 patients, and many other proteins showed a consistent shift from baseline to week 8 in at least three quarters (30 of 39) of the patients. The intra-subject shifts indicate the number of patients showing up or down-regulation. The top intra-subject markers ($q<10^{-6}$) are shown in Table 1. The complete list of 239 proteins with a 0.01% false discovery rate ($q<10^{-4}$) is shown in Table 2. Also shown are the raw p-value and resulting FDR corrected "q-value" reflecting the multiple testing correction.

Figure 9:
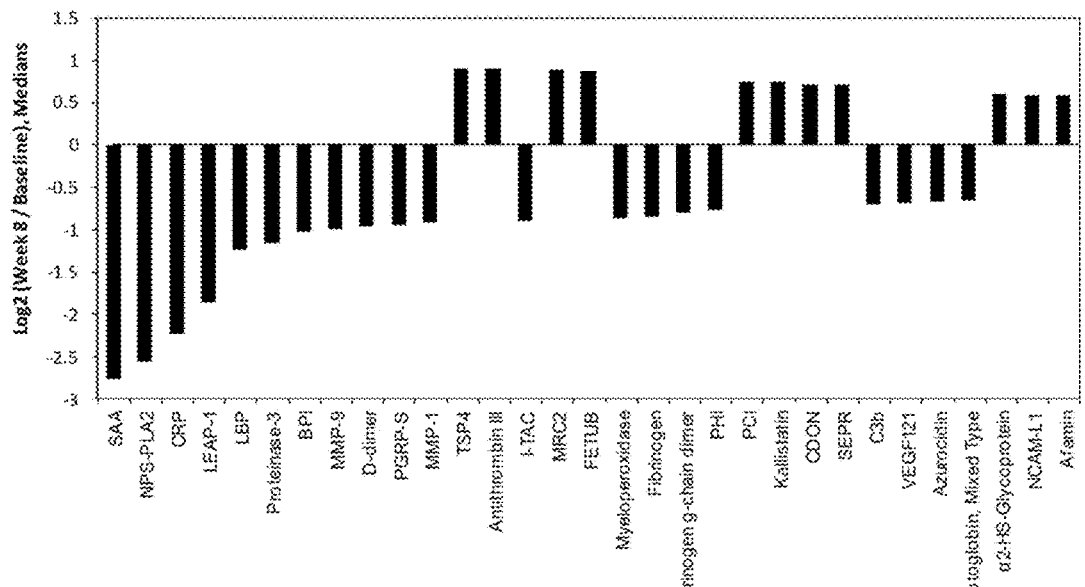
FIG. 9 illustrates paired analysis of markers with largest change between baseline and week 8 of TB therapy in n=39 patients, ranked by the median intra-subject fold-change.

Since the signed rank test is based on the ranks of the measurements, it is difficult to appreciate the magnitude of the changes for some of these proteins. In FIG. 9, the top ranked proteins using the median fold-change between baseline and week 8 are shown. SAA (Serum Amyloid A Protein), NPS-PLA2 (Phospholipase A2), and CRP (C-reactive Protein) showed median within-subject decreases of 6.8-fold, 5.9-fold, and 4.7-fold, respectively, from baseline to week 8. Sixteen additional proteins dropped at least 1.5-fold (median fold change), and a few markers increased between baseline and week 8, including TSP-4, antithrombin III, mannose receptor 2 (MRC-2), fetuin-like protein (FETUB) and plasma serine protease inhibitor (PCI).

The paired data was then analyzed using the database for annotation, visualization and integrated discovery (DAVID). The 239 proteins shown in Table 2 were input into DAVID, which contains structure function information for whole proteins and regions within proteins. The DAVID analysis clustered the 239 proteins based on functional similarity. Those clusters with an enrichment score of >1.3 with a Bonferroni corrected p-value of ≤0.05 were considered significant. The clusters (which are annotated with gene ontology codes) indicated that proteins in pathways involved in response to wounding, inflammatory response, defense response and coagulation were prevalent among the 239 proteins identified. A full list of annotated clusters is provided below in Table 3.

Unpaired Analysis

Figure 10:
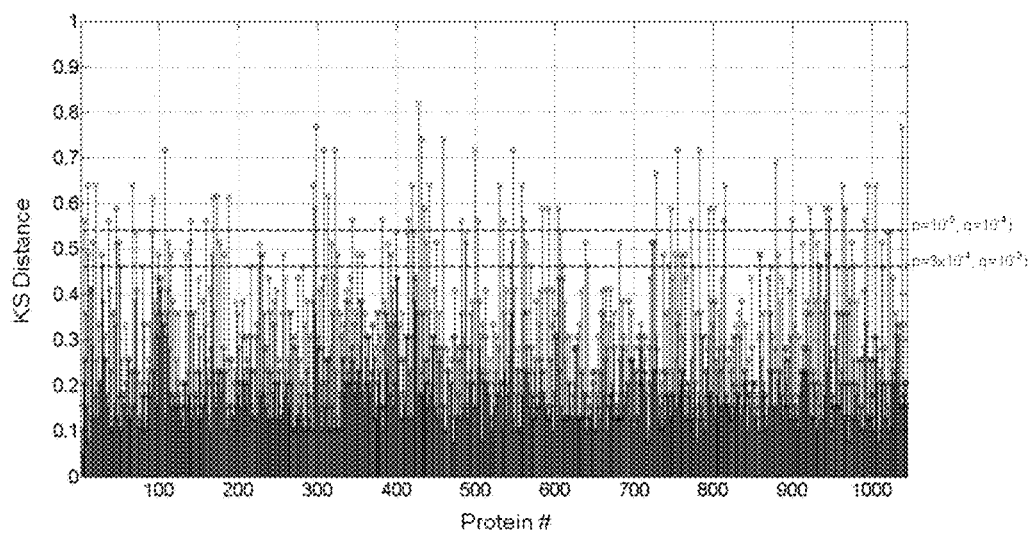
FIG. 10 illustrates feature separation by KS distance for 1,030 measured proteins, with corresponding significance levels shown as q-values.
Figure 11A:
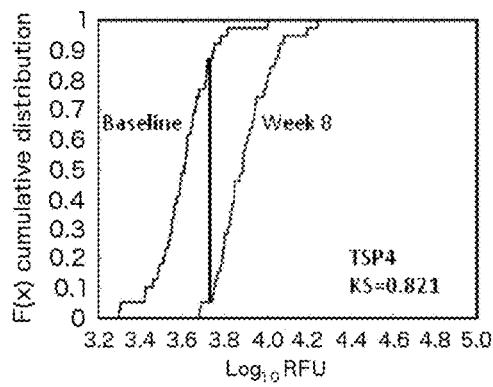
FIGS. 11A-11H illustrate empirical cumulative distribution functions showing $Log_{10}$ RFU for the eight proteins with largest KS distances between baseline and week 8.
Figure 11B:
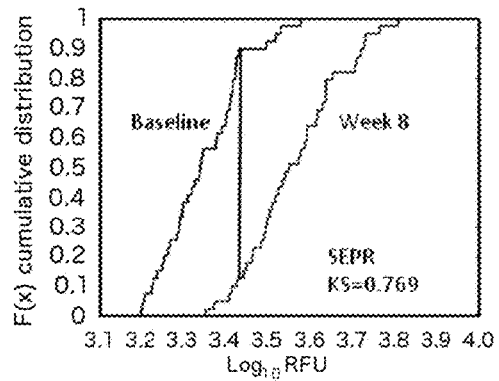
Figure 11C:
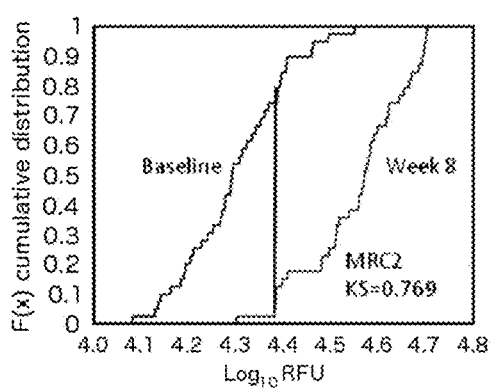
Figure 11D:
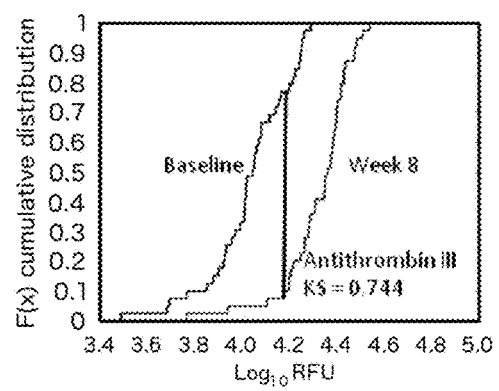
Figure 11E:
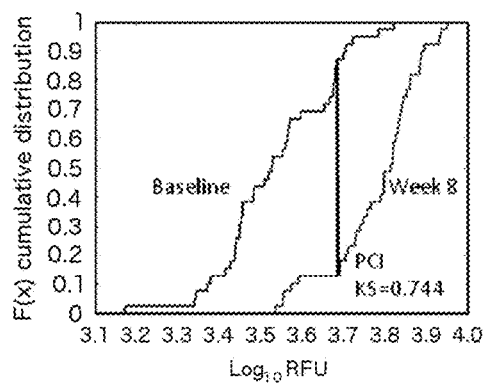
Figure 11F:
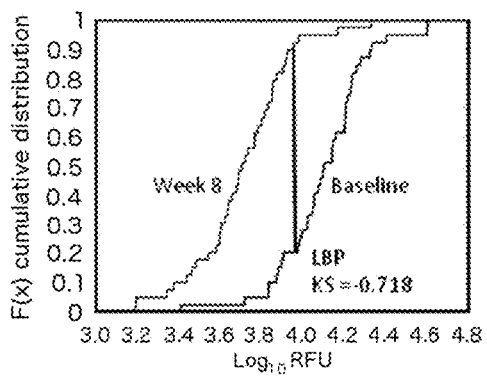
Figure 11G:
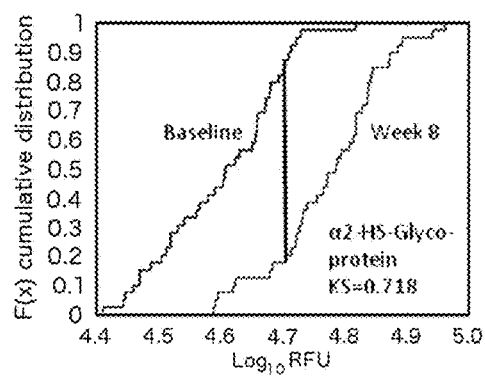
Figure 11H:
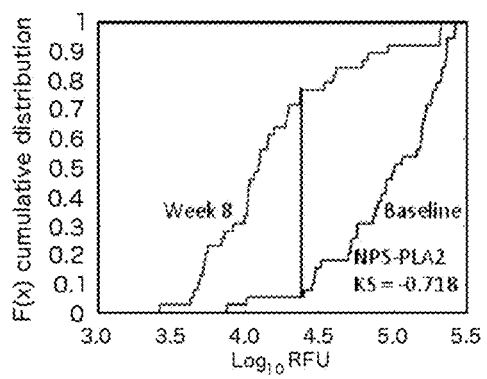
Figure 12A:
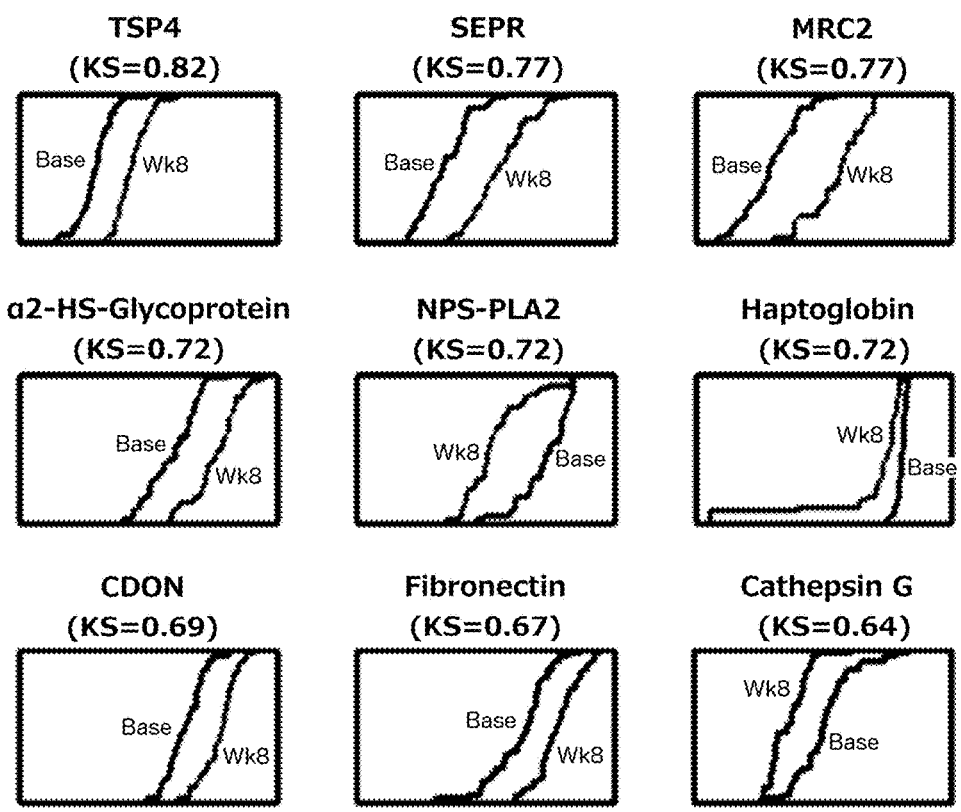
FIGS. 12A-G illustrates empirical cumulative distribution functions for the top 59 proteins from an unpaired analysis of baseline and week 8 measurements in samples from n=39 TB patients.
Figure 12B:
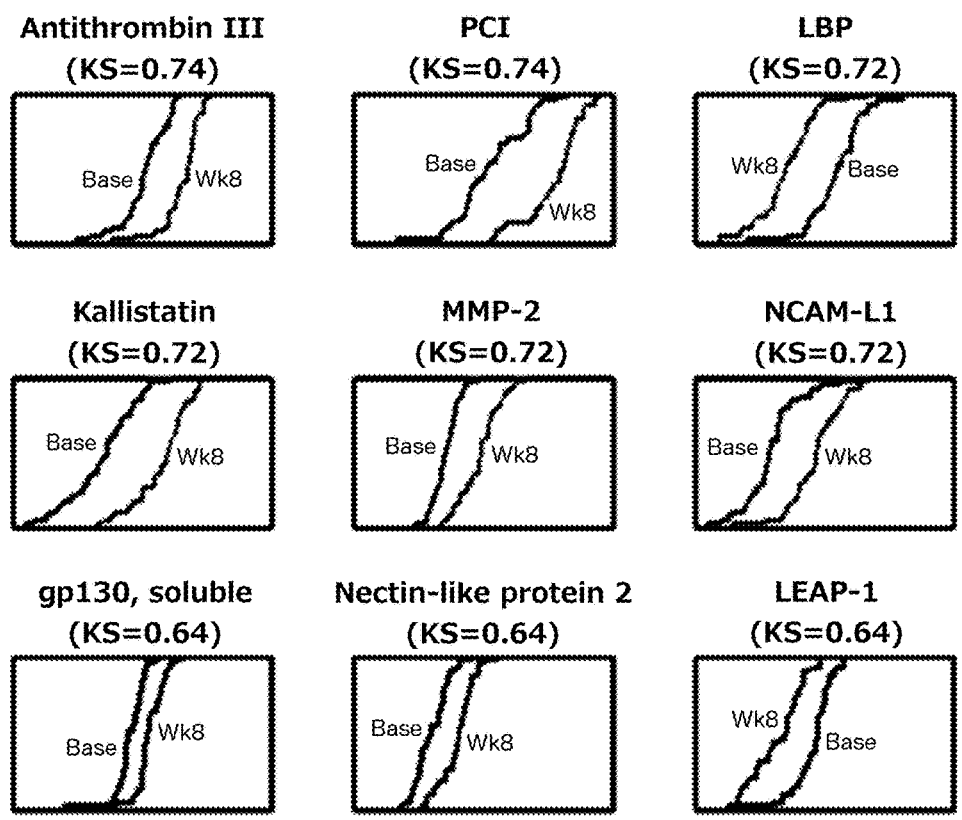
Figure 12C:
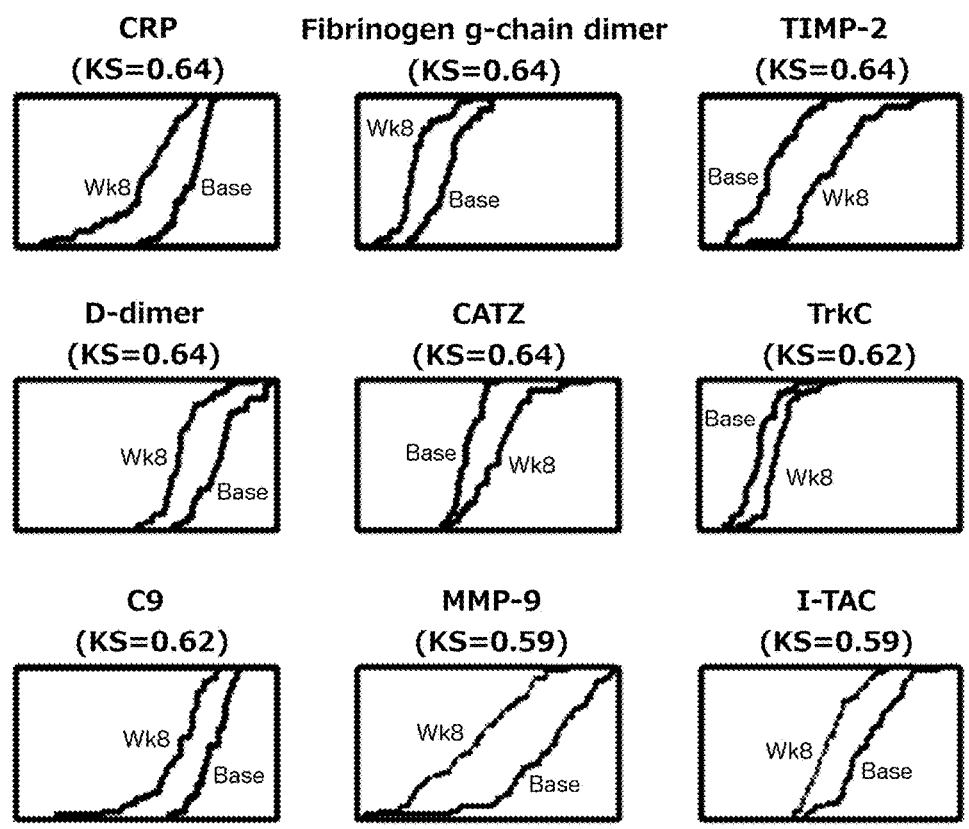
Figure 12D:
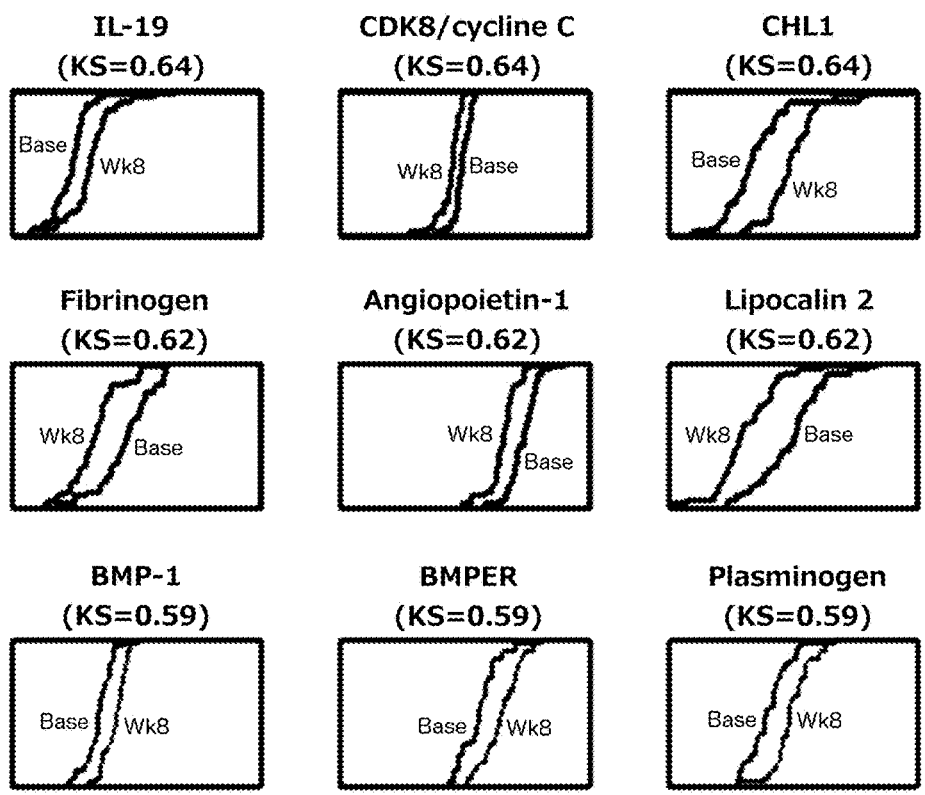
Figure 12E:
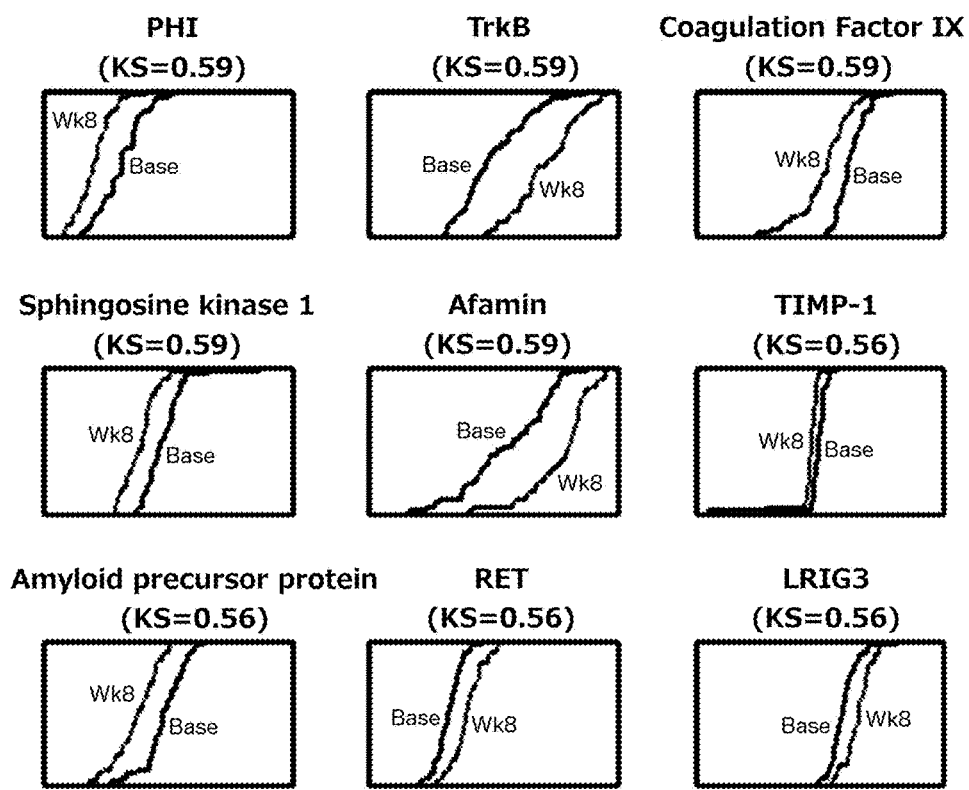
Figure 12F:
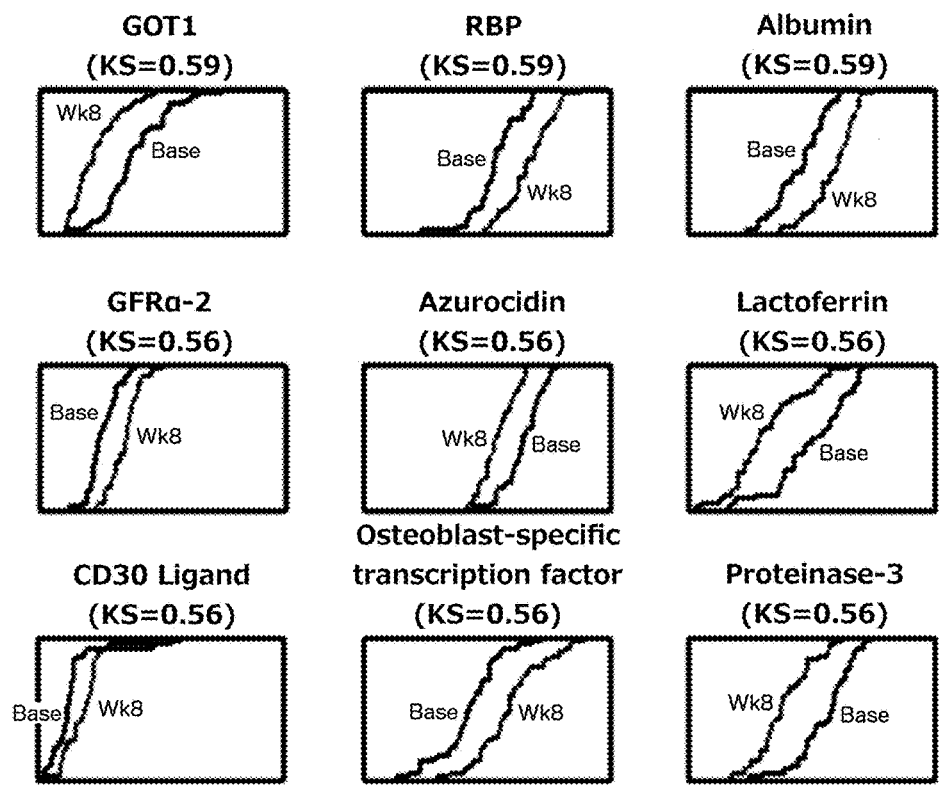
Figure 12G:
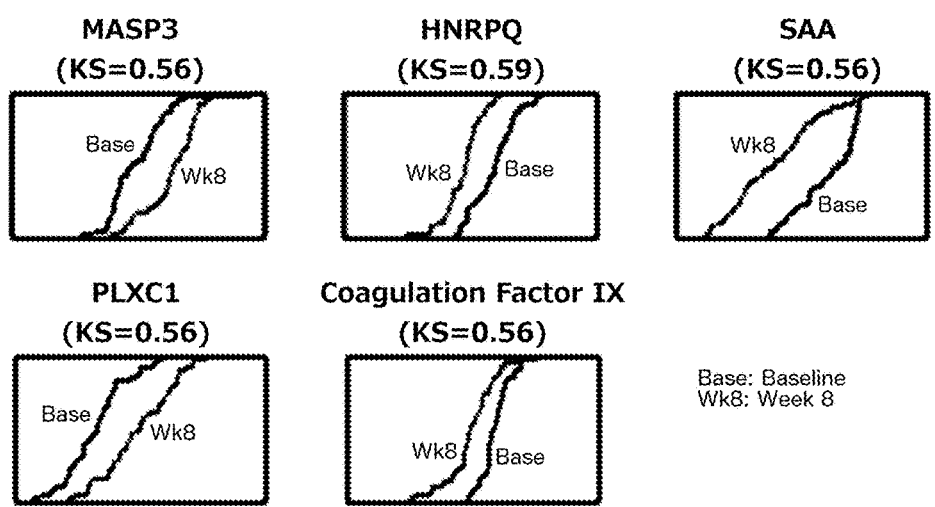
Figure 13:
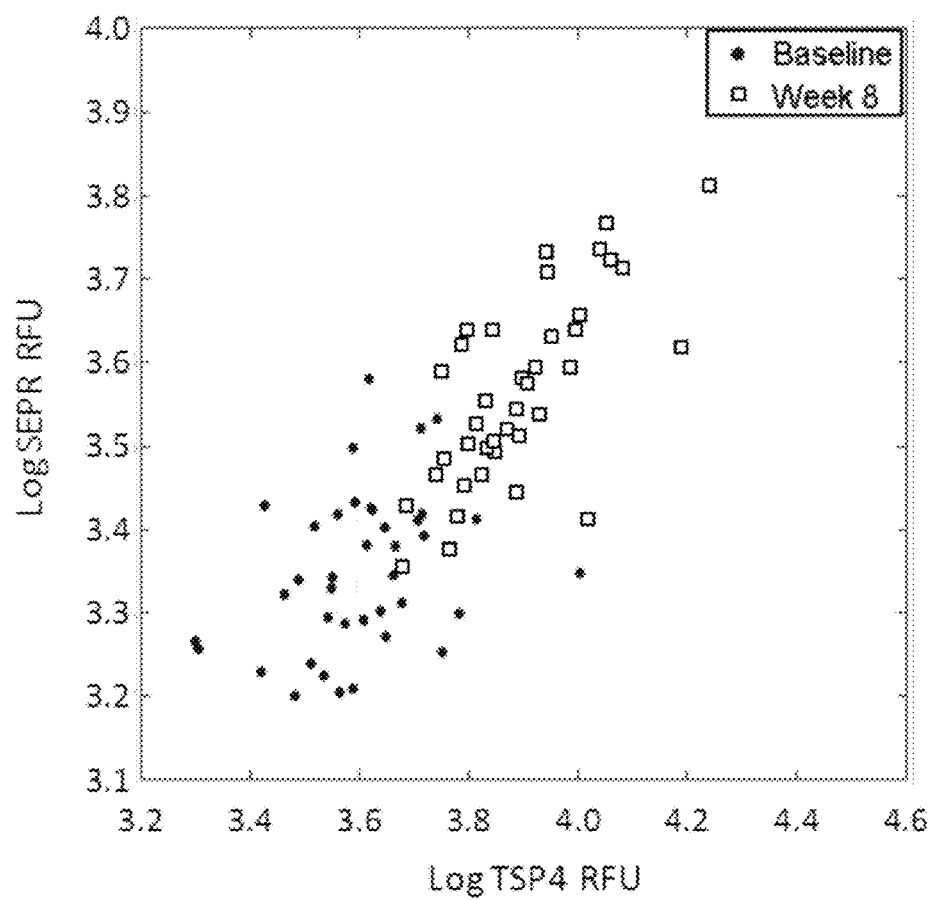
FIG. 13 illustrates a scatter plot of the separation of baseline and week 8 samples using the two markers with the largest KS distances, TSP4 and SEPR. Black dots represent samples from TB patients at baseline and open circles represent samples from the same TB patients after week 8 of treatment.

For prognostic applications, the objective is to be able to predict treatment response using only a single sample. With an unpaired analysis to identify proteins with baseline measurement distributions that differed from the week 8 distributions was performed. At a 0.1% false discovery rate (q<0.001) the KS test identified 116 of 1,030 proteins as differentially expressed between baseline and week 8. KS distances for all proteins are set forth in FIG. 10. The top 60 markers (q<10) are listed in Table 4 and all 116 markers ($q<10^{-3}$) are listed in Table 5. A total of 55/116 features were up-regulated and 61/116 were down-regulated over time. The most significant changes were noted for TSP-4, fibroblast activation protein a (SEPR), MRC-2, antithrombin III, PCI, LPS-binding protein (LBP), α2-HS-glycoprotein, and phospholipase A2 (NPS-PLA2). The empirical cumulative distribution functions for the baseline and week-8 protein measurements (along with an indication of the KS distance between the distributions) for the top eight markers are shown in FIG. 11, and the plots for 51 additional proteins are available in FIG. 12. A scatter plot using the top two markers that were differentially expressed between baseline and 8 week samples can be seen in FIG. 13. Using measurements of one or more of these proteins it is possible to classify each sample within this data set as belonging to either the baseline group (TB) or the week 8 group (treated TB) with sensitivity and specificity exceeding 90%.

Example 3. Calculation of Disease Severity Score

After analysis of serum and receipt of the clinical data, a custom disease severity score was calculated based on chest radiograph (CXR) extent and cavitary disease (absent, diameter of all cavities summed less than or greater than 4 cm) (Falk et al. (1969) Classification of pulmonary tuberculosis, p. 68-76. In Falk et al. (ed.), Diagnostic standards and classification of tuberculosis, vol. 12, National Tuberculosis and Respiratory Disease Association, New York, N.Y.); sputum smear grade (Kent and Kubica G P (1985) Public Health Mycobacteriology: A Guide for the Level III Laboratory. Atlanta, Ga.: Centers for Disease Control); days to detection of a positive culture in liquid media after inoculation and body mass index [weight in kg/(height in m)]$^2$. A clinical spectrum of severity was determined to see if further refinement of disease severity could elucidate markers associated with more severe disease. Given the clinical importance of BMI (Zechariah et al. (2002) Transactions of the Royal Society of Tropical Medicine and Hygiene 96:291-294) and bilateral cavitation (Pakasi et al. (2009) European journal of clinical nutrition 63:1130-1135) these factors were weighted by a factor of two.

The following eight parameters were combined into a single disease severity score:

| | |
|---|---|
| CXRCLASS | Chest X-ray cavitation classification; 1-3, higher more severe; absent (1), <4 cm (2), >4 cm (3) |
| CXREXTNT | Chest X-ray extent of disease; A to C, converted to 1-3: (limited (A), moderate (B), extensive (C)) |
| dtd_base | Days to detection at baseline; the lower the worse (quicker detection if microbial burden is high) |
| smearb | 1-4, the higher the worse (bacillus count in stained sputum sample via microscopy) |
| bmi | Body mass index at enrollment; lower more severe (weight loss is a known effect of TB disease) |
| anycav | 0 or 1 (1 = any cavitation reported at enrollment) |
| bilatcav | 0 or 1 (1 = bilateral cavities reported at enrollment) |
| bilatabn | 0 or 1 (1 = bilateral abnormalities - adenopathy, pleural disease, infiltrates or cavities) |

The parameters were normalized and weighed, and combined into a total score, which was then scaled to values from 0-1.

Figure 14:
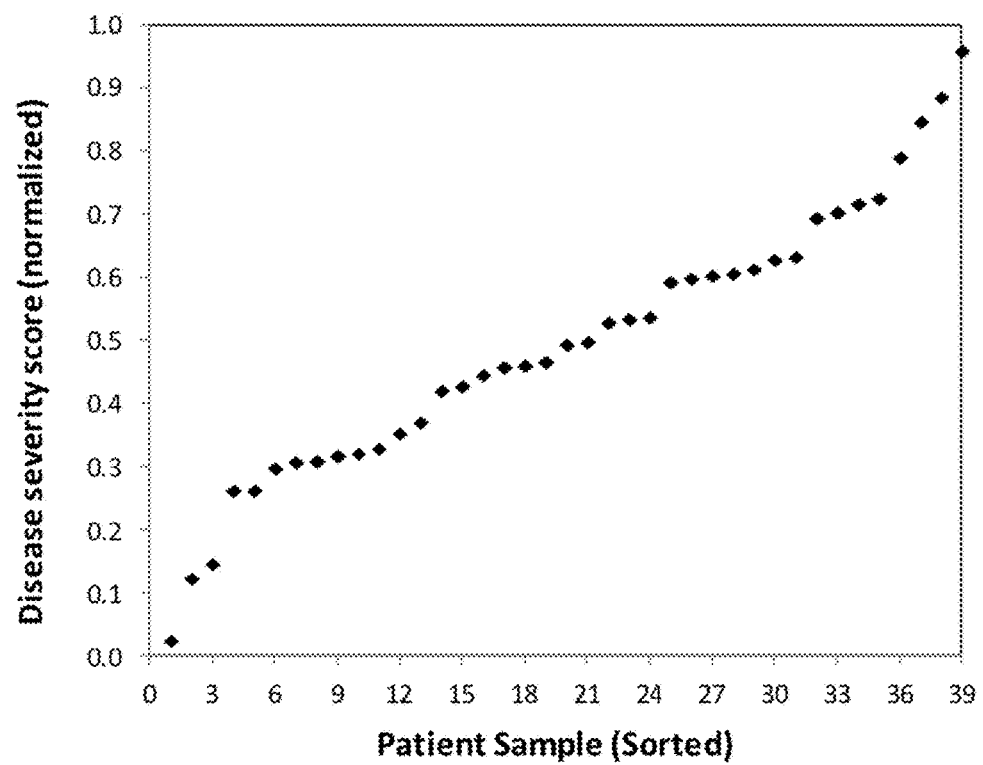
FIG. 14 illustrates normalized disease severity scores of samples from 39 patients with pulmonary TB.

Custom Score=(Total score+10)/16(FIG. 14,Table 6).

Correlations with Severity of Disease

Microbiological and radiographic parameters were used to assess the degree or severity of TB infection. Total cavitary volume and time-to-detection in MGIT culture are markers of severity of disease and bacillary burden in the sputum, respectively. From the data available for the patients involved in the study CXR class showed the strongest association with other parameters such as body mass index (BMI, FIG. 14A) and time-to-detection in MGIT culture (TTD, FIG. 14B). As expected, both were lower in the 13 patients with large and/or bilateral cavities (CXR class 3) compared to the 17 patients without cavitary disease (CXR class 1). Plasminogen (FIG. 14C), which was lower in CXR class 3 compared to class 1, and thromospondin-2 (TSP-2), which was higher in CXR class 3 compared to class 1 (FIG. 14D) best discriminate CXR class 1 from class 3 patients, though these effects had an 18% false discovery rate so on average roughly 1 in 6 such effects are expected to be "false" discoveries.

Toward a more comprehensive association of serum protein levels and disease severity, eight clinical parameters (CXR class, CXR extent, time-to-detection, smear status, presence of any cavity, presence of bilateral cavities or abnormalities, BMI) were combined into a continuous disease severity score as described above. The top markers at baseline distinguishing the thirteen patients with more severe disease (score >0.60) and the thirteen patients with less severe disease (score <0.40) were CRP, SAA, and PLA2 with roughly two-fold increased levels of the median.

Regression analysis was used to identify proteins that increased/decreased with increasing severity as measured by our composite score. Using baseline (log) RFU as the response in a linear model and a 5% false discovery rate, Heparin cofactor 2, platelet factor-4 (PF-4), G-protein coupled receptor associated sorting protein-2 (GASP-2), and α2-antiplasmin had baseline concentrations that were correlated with our disease severity score (FIGS. 15A-D). Low levels of heparin cofactor 2 and GASP2 were both associated with more severe disease. Interestingly, α2-antiplasmin levels at 8 weeks also decreased with increasing severity scores (FIG. 15 E). In contrast, fibrinogen levels measured at 8 weeks were higher in patients with severe disease (FIG. 15 F). Regression analysis using the (log 2) ratio of week 8 to baseline concentration and a 5% false discovery rate uncovered additional proteins whose rate of change was associated with disease severity. The top markers were DKK-1, adiponectin and serum amyloid P component (SAP) (FIGS. 15 G-I). DKK-1 levels decreased from baseline to 8 weeks in patients with mild disease, but remained high or even increased in patients with more severe disease. Adiponectin increased in the majority of patients with mild disease, but remained unchanged in those with the highest disease severity score.

Example 4. Proteins Predictive of Treatment Response

Basic Demographic Parameters and their Correlation with Treatment Response

Figure 15A:
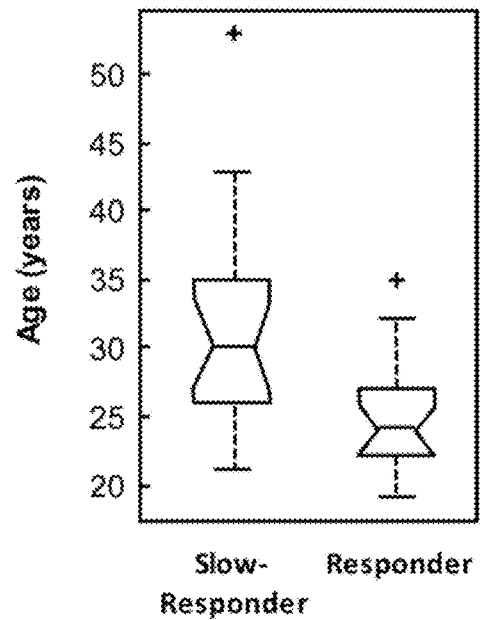
FIGS. 15A-15D depict box plots of patient demographic parameters (age (FIG. 15A), BMI (FIG. 15B), days to detection (FIG. 15C) and CXR extent (FIG. 15D)) in responders and slow-responders, depicting quartiles, medians, and outliers.
Figure 15B:
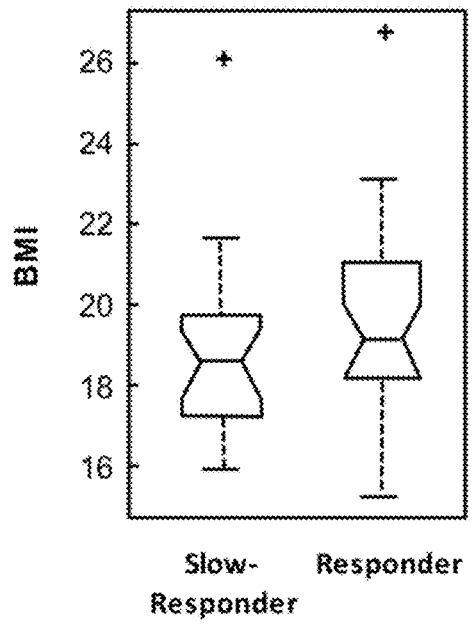
Figure 15C:
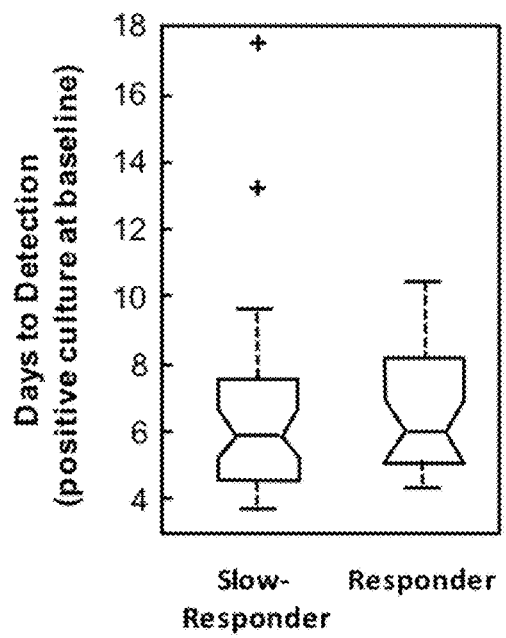
Figure 15D:
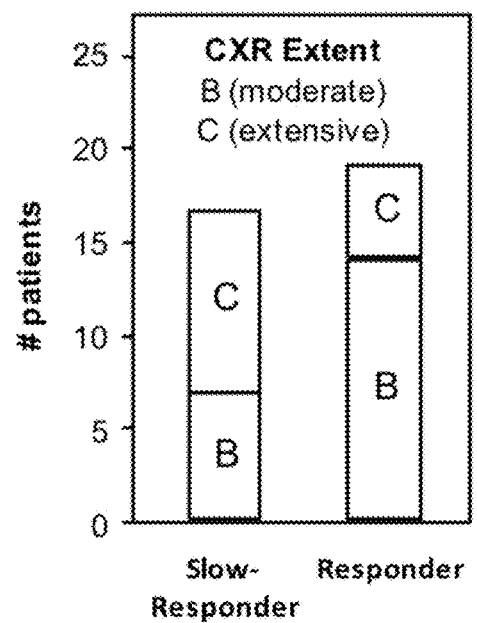

Age was an important predictor of TB treatment response (FIG. 15A). Responders were younger than slow-responders (median age 25.7 yrs vs. 31.8 yrs, p=0.01). Though responders had slightly higher BMI than slow-responders (BMI of 19.7 vs 18.8 (FIG. 15B)), the difference was not significant (p>0.1), nor was the difference in quantitative culture analysis at baseline, determined as number of days to detection in liquid culture (p>0.1) (FIG. 15C). Among radiographic parameters used to assess the degree or severity of TB infection, chest x-ray (CXR) extent differed between responders and slow-responders (p=0.02), with twice as many responders having CXR extent B (moderate) and twice as many slow-responders having CXR extent C (extensive), as shown in FIG. 15D.

Protein Markers at Baseline Based on Treatment Response

Figure 16A:
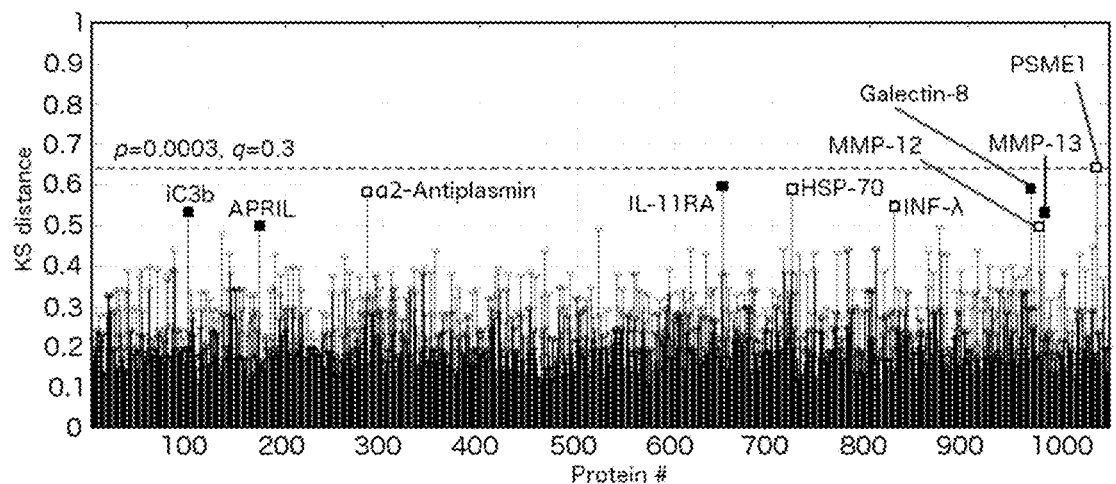
FIG. 16A depicts KS distance plots of 1030 proteins measured in baseline samples from responders versus slow-responders. Squares mark the top ten proteins that are higher in responders (open squares) or slow-responders (solid squares). The dashed line indicates a Bonferroni-corrected 30% significance level.
Figure 16B:
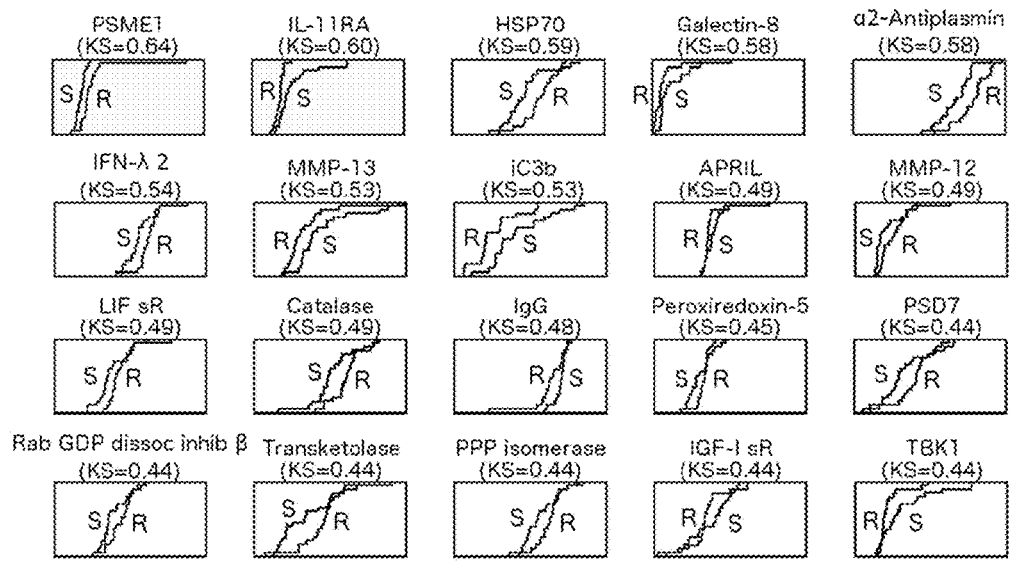
FIG. 16B depicts cumulative distribution function (CDF) plots of the most differentially expressed proteins in responders (R) versus slow-responders (S) at baseline. Axis labels and scales for RFU (x-axis) and for cumulative fraction of all samples within each group (y-axis) were omitted for clarity.

In one embodiment, proteins that distinguish responders from slow-responders at baseline were identified using the Kolmogorov-Smirnov (KS) test. FIG. 16A and Table 8 show the KS distance for the comparison between responders and slow-responders in each of the 1030 proteins. FIG. 16B shows plots of the empirical cumulative distribution functions of the relative fluorescence units (RFU) for the top 20 proteins with the largest KS distances between responders (R) and slow-responders (S). Table 9 (top section) shows the top ten proteins with the largest KS distances for the comparison between responders and slow-responders among all 1030 proteins. The top five proteins have a 29% false discovery rate indicating two of these five may be expected to false discoveries. Responders had higher levels than slow-responders of proteasome activator complex subunit 1 (PSME1), heat shock 70 kDa cognate protein 8 (HSP 70), α2-antiplasmin, interferon lambda 2 (IFN-k), and matrix metalloproteinase 12 (MMP-12). In turn, slow responders had higher levels of interleukin 11 receptor antagonist (IL-11 Rα), Galectin-8, matrix metalloproteinase 13 (MMP-13), iC3b, and a proliferation inducing ligand of the TNF ligand family (APRIL) as compared to rapid responders.

Protein Markers at 8 Weeks Based on Treatment Response

Figure 17A:
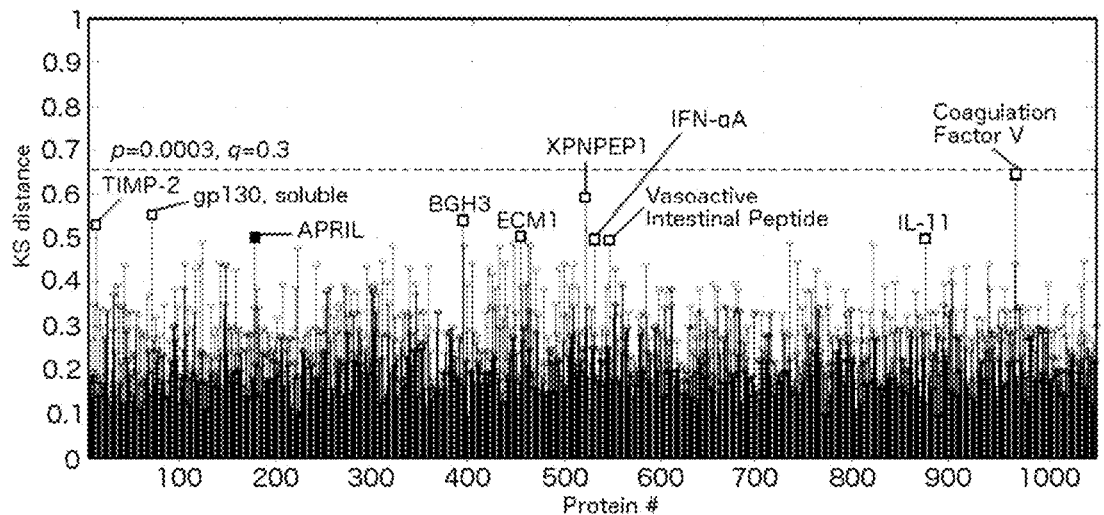
FIGS. 17A and 17B depict protein markers at 8 weeks based on treatment response.
Figure 17B:
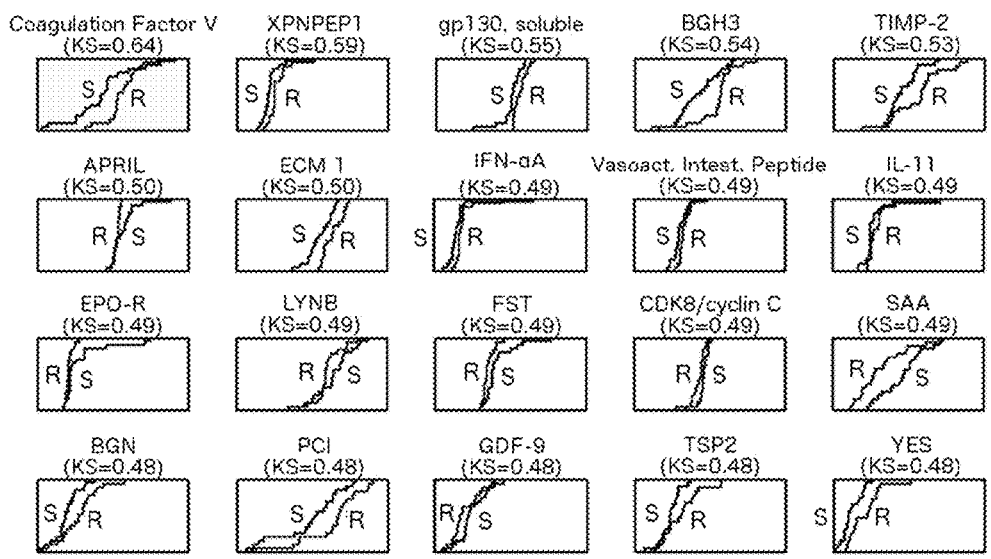

The KS distances between responders and slow-responders were determined for all proteins measured in the 8-week samples (FIG. 17A), and cumulative distribution function plots (FIG. 17B) are shown for the top 20 proteins with the largest KS distances between responders (R) and slow-responders (S). Table 9 (midsection) shows the proteins that exhibited the largest differential expression between responders and slow-responders at week 8 based on the KS distances. Coagulation Factor V showed the most significant difference and was elevated in responders compared to slow-responders. Xaa-Pro aminopeptidase 1 (XPNPEP1), soluble gp130, transforming growth factor-beta-induced protein ig-h3 (BGH3), metalloproteinase inhibitor 2 (TIMP-2), extracellular matrix protein 1 (ECM-1), vasoactive intestinal peptide (VIP), interferon alpha-2 (IFN-αA), IL-11 were also elevated in responders compared to slow-responders. Of the other proteins listed in this section of Table 2, only tumor necrosis factor ligand superfamily member 13 (APRIL) was lower in responders than slow-responders.

Figure 18:
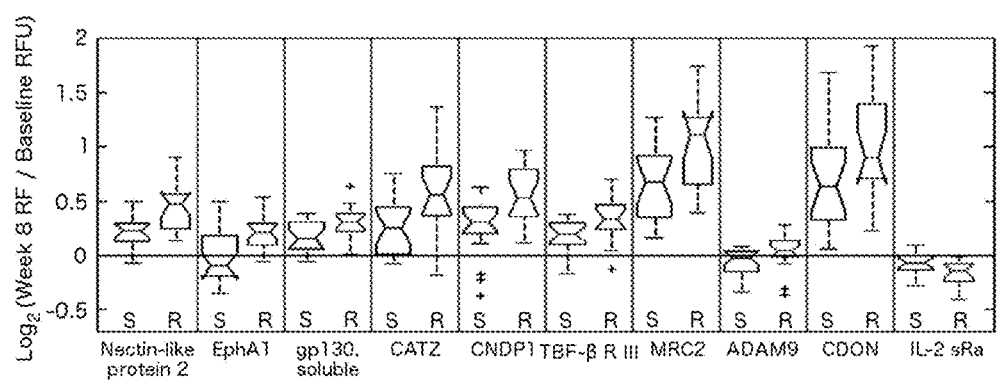
FIG. 18 depicts box plots for the log 2 ratio of week 8 to baseline signal in responders (R) and slow-responders (S).

A "paired" analysis of responders and slow-responders was conducted using the log-ratio of within-subject baseline to 8-week response as a "fold change" metric (FIG. 18). This analysis targets proteins that exhibit differential change between the two time points in the responders (R) compared to slow-responders (S). The ranking of proteins by the KS distance associated with distributions of log-ratios in the two groups is illustrated in Table 9 (bottom section). The top two features were EphAl (Ephrin type-A receptor 1) and gp130; both previously identified in the unpaired analysis. Also appearing are TIMP-1, MMP-8 (metalloproteinase-8, also known as neutrophil collagenase), AMPM2 (methionine aminopeptidase 2), and MMP-12 (macrophage metalloelastase).

Proteins were subsequently ranked using the Wilcoxon rank sum test to identify those with different median fold changes in the responders and slow-responders. The ten proteins with the most differential change are listed in Table 10. For the first nine of these proteins, the fold-change in signal from baseline to week 8 was larger in responders than in slow responders. These features were nectin-like protein 1, EphAl (Ephrin type-A receptor 1), gp130, CATZ, CNDP1, TGF-b RIII, MRC2, ADAMS, and CDON. IL-2 sRα was the only protein that decreased in both groups, but decreased to a greater extent in responders compared to slow-responders.

Table 11 sets forth some additional markers that changed to a greater extent between week-8 responders and slow-responders than between week 8 slow-responders and all baseline samples. The levels of these proteins track closely together in baseline and week-8 slow-responders, but are clearly different in week-8 responders.

Predicting Treatment Response with a Combination of Markers

Figure 19A:
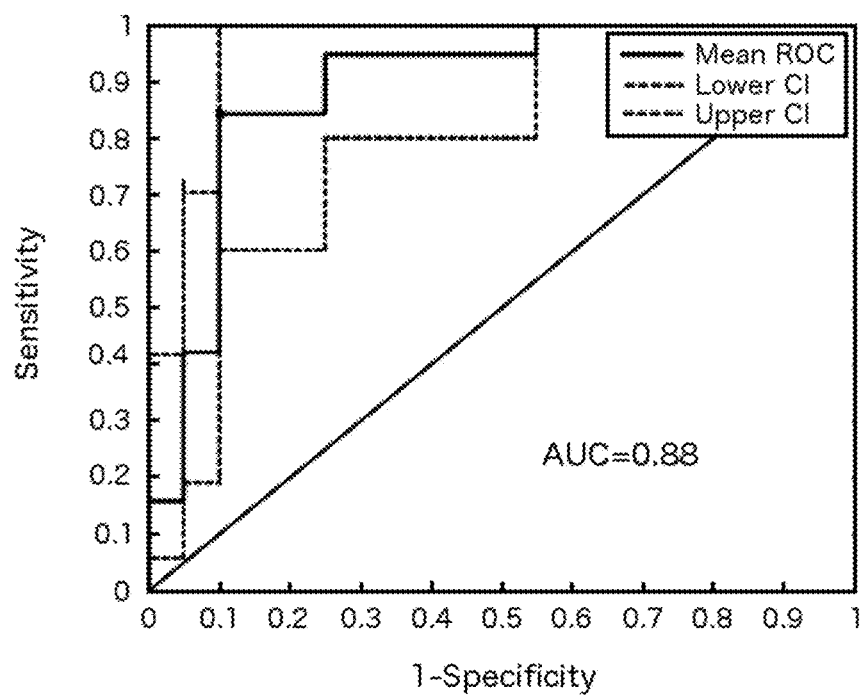
FIGS. 19A and 19B show a Naïve Bayes model using five markers (coagulation factor V, XPNPEP1, soluble gp130, TIMP-2 and ECM1) as a classifier to "predict" treatment response at week 8.
Figure 19B:
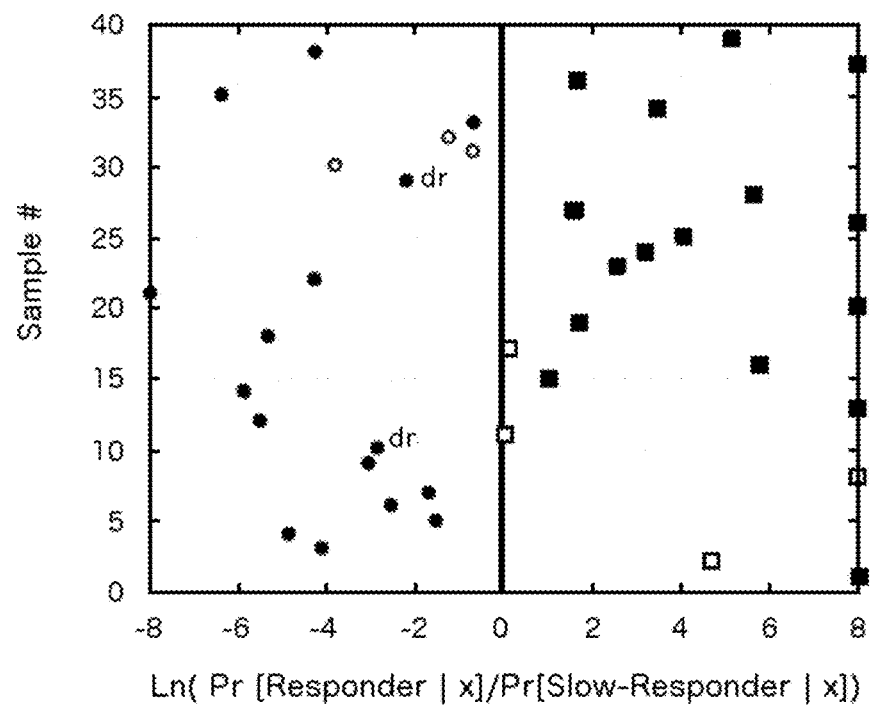

Several strategies to identify signatures of treatment response, specifically to use serum protein measurements for the prediction of the culture status at 8 weeks were explored. In a first approach, at 8 weeks the top markers distinguishing responders vs. slow-responders were selected based on large KS distances (0.5) after excluding markers with low signal strength (<500 RFU). A five-feature signature including coagulation factor V, XPNPEP1, gp130, TIMP-2 and ECM1 were combined in a naïve Bayes classifier to "predict" treatment response using 8-week data. The procedure is outlined schematically in FIGS. 1A and B. In one embodiment, the biological sample is optionally diluted and run in a multiplexed aptamer assay. This five feature classifier revealed an ROC curve with an AUC value of 0.89 and confidence interval of 0.75-0.98 (FIG. 19A). The corresponding classification of the training samples is depicted in FIG. 19B. The model was fit to log RFU values using robust parameter estimation. No covariate adjustment was performed, though subject age and BMI are both strong predictors of treatment response. This pilot study was too small to withhold an independent test set to assess the classifier performance so 5-fold stratified cross-validation was used to generate performance estimates. Sensitivity and specificity were 0.85+/−0.1 and 0.95+/−0.05 with an AUC of 0.88+/−0.07.

Figure 20A:
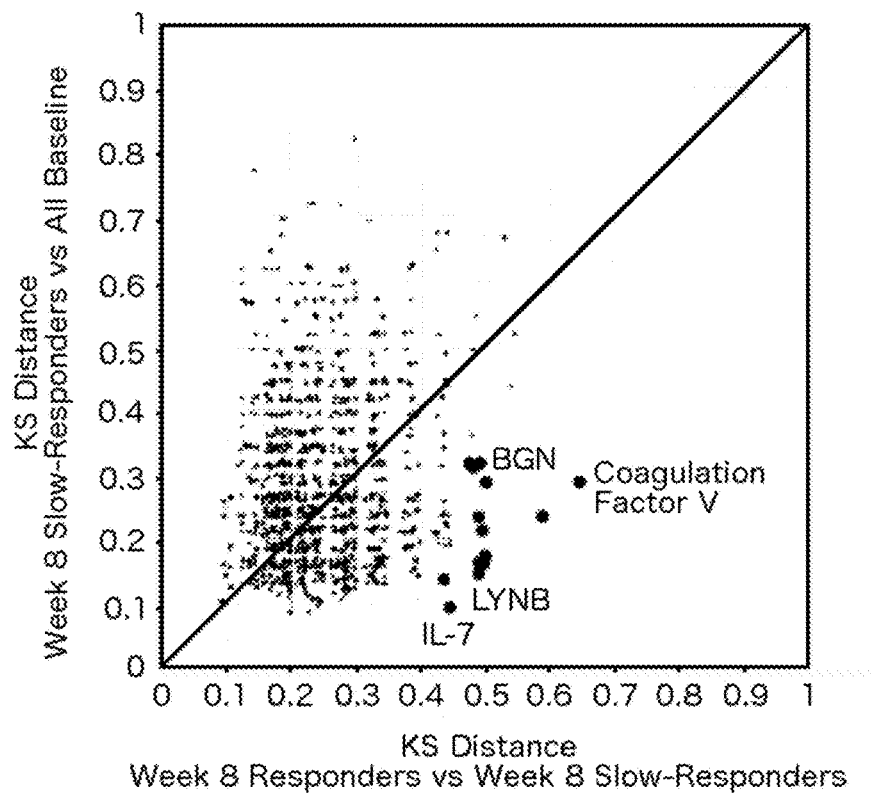
FIGS. 20A and 20B shows a matrix plot of the KS-distances of slow-responders (week 8) to baseline (all) versus responders (week 8) to slow-responders (week 8). Potential treatment response markers fall into the lower right area (large dots).
Figure 20B:
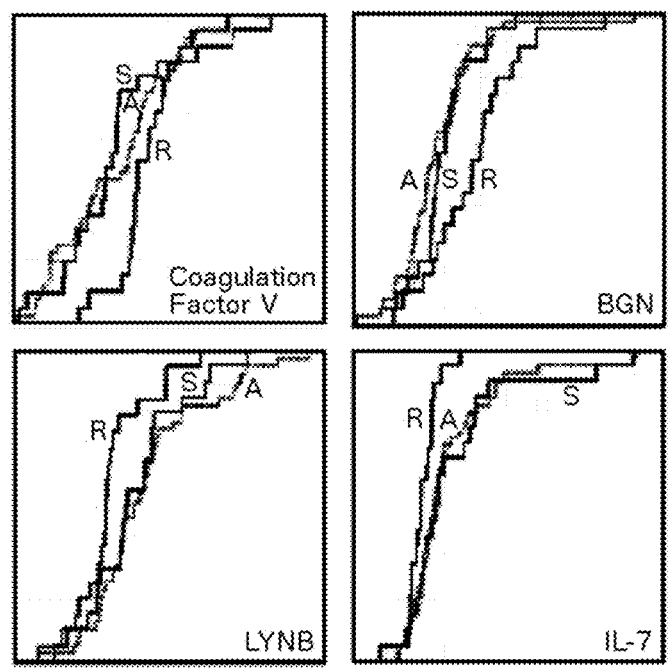

In a second approach, markers that changed to a greater extent between week-8 responders and slow-responders than between week 8 slow-responders and all baseline samples were identified. FIG. 20A shows a scatter plot of the KS distances for the comparison of baseline samples to week 8 slow-responders versus the KS distances for the comparison of week-8 responders and slow-responders. Markers associated with treatment response congregate in the lower right area since there is greater differential expression (larger KS distance) at week 8 than between week 8 slow-responders and baseline. Many of the proteins identified above appear in the lower right corner, in addition, BGN (matrix proteoglycan), YES and LYNB (tyrosine kinases) and IL-7 are located in that area. FIG. 20B shows the empirical cumulative distribution functions (CDFs) for four representative markers (BGN, IL-7, coagulation Factor V, and LYNB) illustrating that the levels of these proteins track closely together in baseline and week-8 slow-responders, but are clearly different in week-8 responders.

Figure 21A:
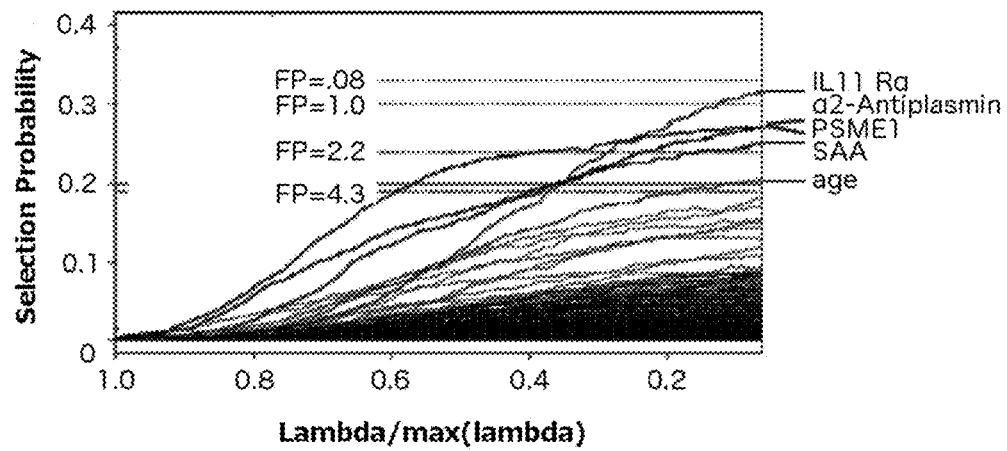
FIGS. 21A-21D illustrate models and algorithms to "predict" treatment response at week 8.
Figure 21B:
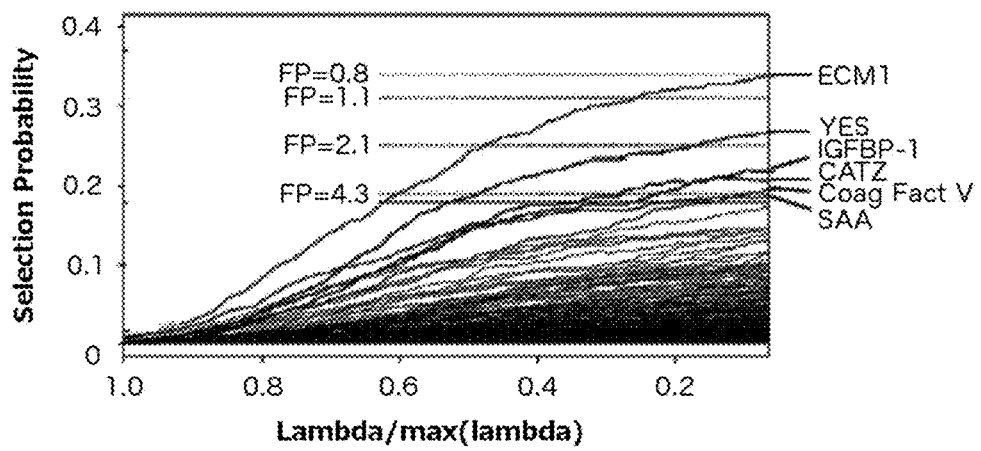
Figure 21C:
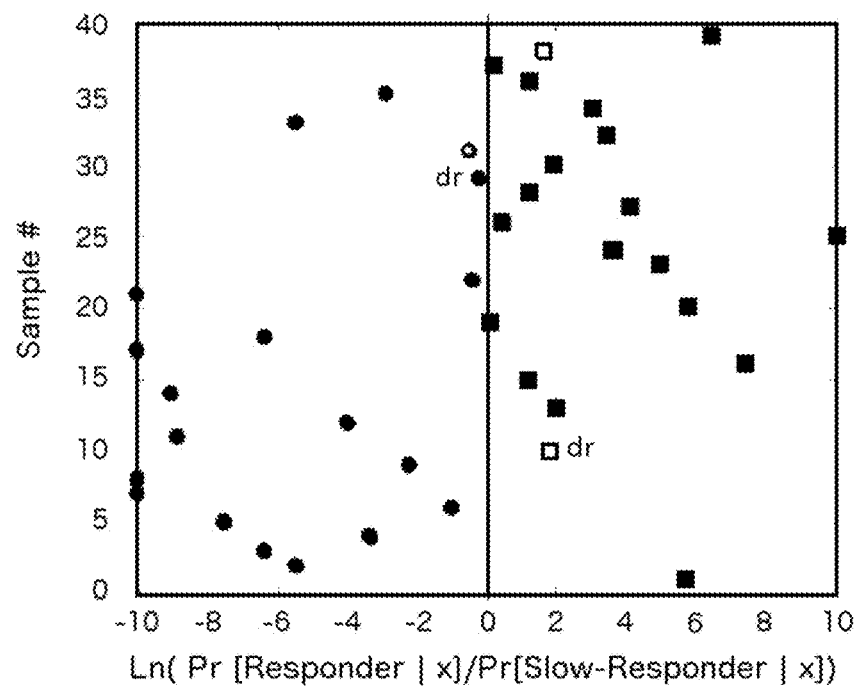
Figure 21D:
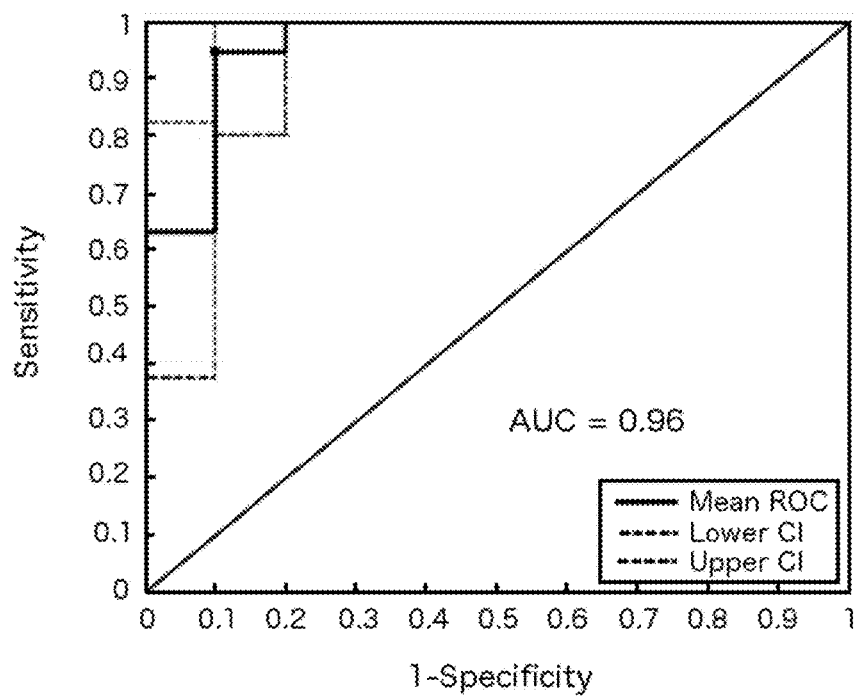

In yet another embodiment, stability selection was used to identify a subset of covariates from the set of 1030 protein measurements combined with age, gender, BMI, smear status, CXR Class, CXR extent and time to detection. The most stable predictive markers at baseline were IL-11 Rα, α2-Antiplasmin, PSME1, SAA, and subject age (FIG. 21A). Three of the proteins are among those with large KS distances between responders and slow-responders as mentioned above, and the associated q-values suggested on average at least one of these was falsely discovered. This assessment is consistent with the average number of false discoveries expected by stability selection at different selection probabilities (FIG. 21A). At eight weeks, the most predictive stable markers for treatment response were ECM1, YES, IGFBP1, CATZ, Coagulation Factor V, and SAA (FIG. 21B).

As an example of a 5-marker signature to "predict" treatment response, baseline measurements of IL-11 Rα, α2-Antiplasmin, PSME1, and SAA were combined with subject age in a logistic regression model. The corresponding sample classification (FIG. 21C) and resulting ROC curve (FIG. 21D) show the performance of this model on the training data. Since there were too few samples in this study to withhold an independent "test set", a 5-fold stratified cross-validation was used to estimate model performance. Under cross-validation, the estimated AUC was 0.9±0.05 with sensitivity 0.9±0.06 and specificity 0.95±0.05. Similar performance was observed from a naive Bayes model constructed using baseline measurements of the first 5 proteins in Table 9 with the best KS distances (PSME1, IL-11 Rα, HSP70, Galectin-8, and α2-Antiplasmin).

Markers Associated with Time-to-Culture-Conversion

Figure 22A:
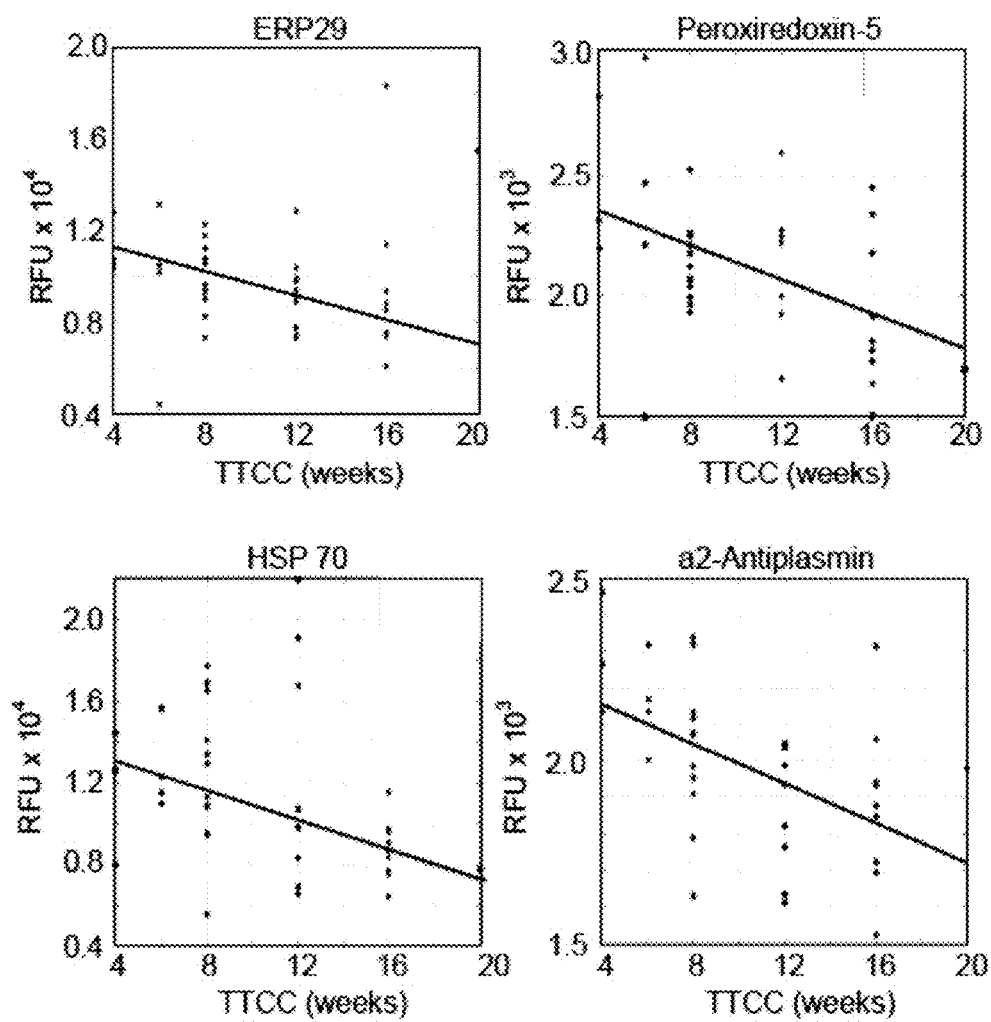
FIGS. 22A-22D depict association of serum protein levels with TTCC.
Figure 22B:
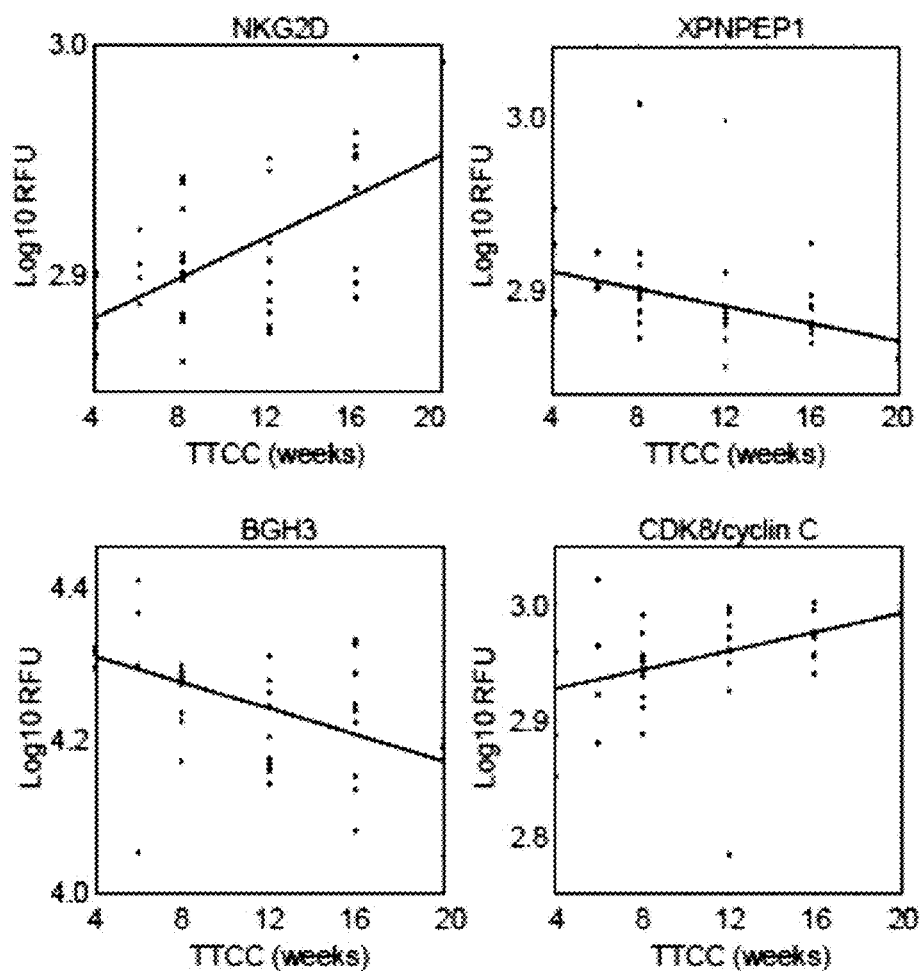
Figure 22C:
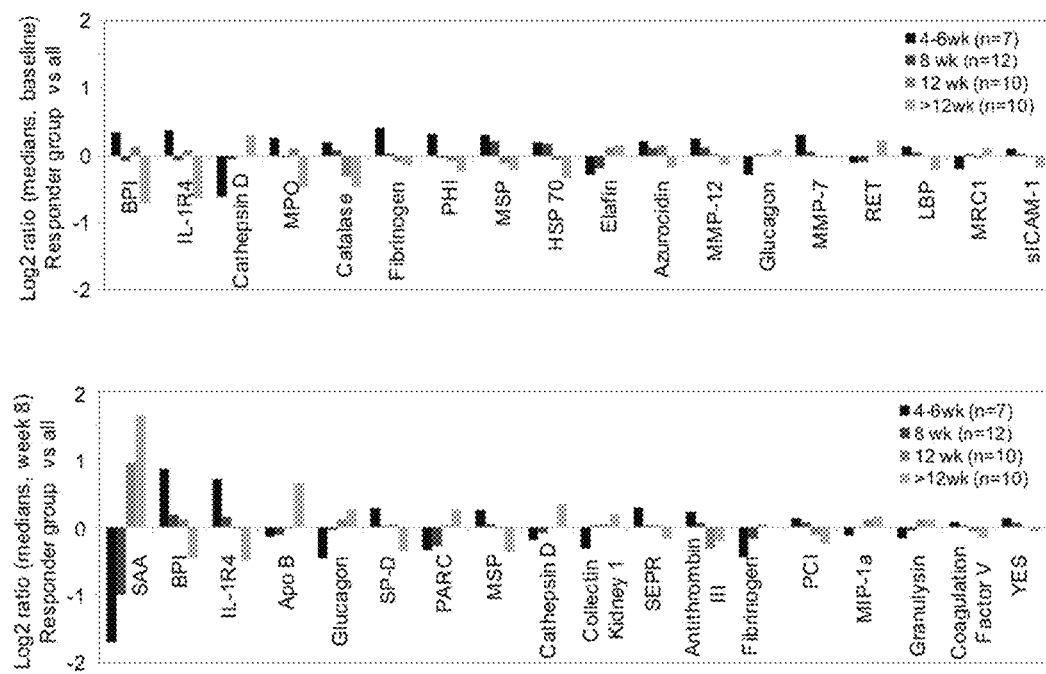
Figure 22D:
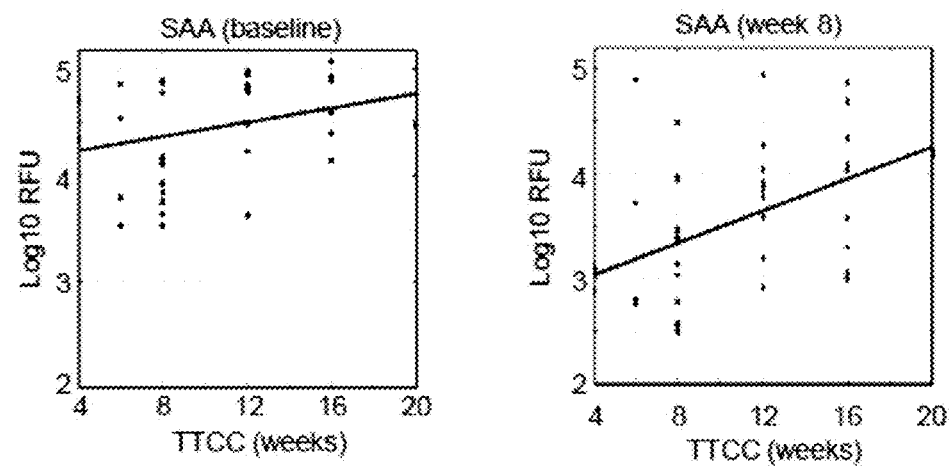

Toward the identification of surrogate markers for treatment response, meta data and serum protein data were analyzed with regard to time-to-culture-conversion (TTCC), defined as the first of at least two consecutive time-points where negative cultures (solid and liquid) were obtained. Among the 39 patients there were six responder groups, with TTCC of 4 wk (n=3), 6 wk (n=4), 8 wk (n=12), 12 wk (n=10), 16 wk (n=9), and 20 wk (n=1). TTCC did not correlate with clinical data obtained at baseline, such as smear/culture results, chest X-ray classifications, presence of cavities, or BMI (data not shown). Univariate regression analysis of baseline and week-8 protein measurements (log RFU) on TTCC was performed and sorted by statistical significance (Table 12). At baseline, lower levels of ERP29, peroxiredoxin-5, HSP-70, and α2-antiplasmin were associated with longer TTCC (FIG. 22A). At 8 weeks, NKG2D (KLRK1) and CDK8 showed increased levels in samples from patients with longer TTCC, while XPNPEP1, and BGH3 (TGFBI) levels were lower (FIG. 22B). Comparison of the medians of all 8-week measurements within the different responder groups showed a large number of proteins associated with neutrophil function (FIG. 22C). BPI (bactericidal permeability-increasing factor) and IL-1 R4 were higher in fast-responders compared to slow-responders, and cathepsin D was lower in fast-responders compared to slow-responders. The largest differences between the responder groups were for SAA measured at 8 weeks, and a more detailed regression analysis using baseline data and week-8 data showed that signals dropped from baseline to week 8 by almost 10-fold, but a much sharper decrease was observed in samples from the fast-responders (FIG. 22D)

TABLE 1

Differential protein expression between baseline and week 8 in paired samples from n = 39 patients treated for pulmonary TB

| Rank | Target | Swiss Prot[a] | Intrasubject Shift[b] (baseline to week 8) Up (n) | Down (n) | p-value | q-value |
|---|---|---|---|---|---|---|
| 1) | TIMP-2 | P16035 | 39 | | 5.3e−08 | 5.48e−07 |
| 2) | GFRα-2 | O00451 | 39 | | 5.3e−08 | 5.48e−07 |
| 3) | MRC2 | Q9UBG0 | 39 | | 5.3e−08 | 5.48e−07 |
| 4) | Haptoglobin, Mixed Type | P00738 | | 39 | 5.3e−08 | 5.48e−07 |
| 5) | LBP | P18428 | | 39 | 5.3e−08 | 5.48e−07 |
| 6) | amyloid precursor protein | P05067 | | 39 | 5.3e−08 | 5.48e−07 |
| 7) | BGH3 | Q15582 | 39 | | 5.3e−08 | 5.48e−07 |
| 8) | TSP4 | P35443 | 39 | | 5.3e−08 | 5.48e−07 |
| 9) | FETUB | Q9UGM5 | 39 | | 5.3e−08 | 5.48e−07 |
| 10) | PCI | P05154 | 39 | | 5.3e−08 | 5.48e−07 |
| 11) | Kallistatin | P29622 | 39 | | 5.3e−08 | 5.48e−07 |
| 12) | α2-HS-Glycoprotein | P02765 | 39 | | 5.3e−08 | 5.48e−07 |
| 13) | CHL1 | O00533 | 39 | | 5.3e−08 | 5.48e−07 |
| 14) | CDON | Q4KMG0 | 39 | | 5.3e−08 | 5.48e−07 |
| 15) | D-dimer | P02671, P02675, P02679 | | 39 | 5.3e−08 | 5.48e−07 |
| 16) | MMP-1 | P03956 | | 39 | 5.3e−08 | 5.48e−07 |
| 17) | contactin-1 | Q12860 | 38 | | 5.7e−08 | 5.48e−07 |
| 18) | CD109 | Q6YHK3 | 38 | | 5.7e−08 | 5.48e−07 |
| 19) | IGFBP-7 | Q16270 | 38 | | 5.7e−08 | 5.48e−07 |
| 20) | Sphingosine kinase 1 | Q9NYA1 | | 38 | 5.7e−08 | 5.48e−07 |
| 21) | CRP | P02741 | | 38 | 5.7e−08 | 5.48e−07 |
| 22) | SEPR | Q12884 | 38 | | 5.7e−08 | 5.48e−07 |
| 23) | TIMP-3 | P35625 | | 38 | 6.1e−08 | 5.48e−07 |
| 24) | Lipocalin 2 | P80188 | | 38 | 6.1e−08 | 5.48e−07 |
| 25) | NAP-2 | P02775 | | 38 | 6.1e−08 | 5.48e−07 |
| 26) | Nectin-like protein 2 | Q9BY67 | 38 | | 6.1e−08 | 5.48e−07 |
| 27) | Proteinase-3 | P24158 | | 38 | 6.1e−08 | 5.48e−07 |
| 28) | PDGF-BB | P01127 | | 38 | 6.1e−08 | 5.48e−07 |
| 29) | MMP-2 | P08253 | 38 | | 6.1e−08 | 5.48e−07 |
| 30) | TIMP-1 | P01033 | 37 | | 6.6e−08 | 5.48e−07 |
| 31) | ROR1 | Q01973 | 37 | | 6.6e−08 | 5.48e−07 |
| 32) | IGFBP-6 | P24592 | 37 | | 6.6e−08 | 5.48e−07 |
| 33) | PAI-1 | P05121 | | 38 | 6.6e−08 | 5.48e−07 |
| 34) | Protein C | P04070 | 37 | | 6.6e−08 | 5.48e−07 |
| 35) | C9 | P02748 | | 38 | 6.6e−08 | 5.48e−07 |
| 36) | GDF-9 | O60383 | | 37 | 6.6e−08 | 5.48e−07 |
| 37) | Carbonic anhydrase 6 | P23280 | 37 | | 6.6e−08 | 5.48e−07 |
| 38) | RBP | P02753 | 37 | | 6.6e−08 | 5.48e−07 |
| 39) | Albumin | P02768 | 38 | | 6.6e−08 | 5.48e−07 |
| 40) | Fibronectin | P02751 | 37 | | 6.6e−08 | 5.48e−07 |
| 41) | Antithrombin III | P01008 | 38 | | 7.2e−08 | 5.48e−07 |
| 42) | α1-Antitrypsin | P01009 | | 37 | 7.2e−08 | 5.48e−07 |
| 43) | HRG | P04196 | 38 | | 7.2e−08 | 5.48e−07 |
| 44) | Angiopoietin-1 | Q15389 | | 38 | 7.8e−08 | 5.48e−07 |
| 45) | ATS13 | Q76LX8 | 37 | | 7.8e−08 | 5.48e−07 |
| 46) | Coagulation Factor VII | P08709 | 37 | | 7.8e−08 | 5.48e−07 |
| 47) | Afamin | P43652 | 38 | | 7.8e−08 | 5.48e−07 |
| 48) | TrkB | Q16620 | 37 | | 7.8e−08 | 5.48e−07 |

TABLE 1-continued

Differential protein expression between baseline and week 8 in paired samples from n = 39 patients treated for pulmonary TB

| Rank | Target | Swiss Prot[a] | Intrasubject Shift[b] (baseline to week 8) | | p-value | q-value |
|---|---|---|---|---|---|---|
| | | | Up (n) | Down (n) | | |
| 49) | GOT1 | P17174 | | 38 | 7.8e–08 | 5.48e–07 |
| 50) | Azurocidin | P20160 | | 38 | 8.4e–08 | 5.80e–07 |
| 51) | NCAM-L1 | P32004 | 38 | | 9.1e–08 | 6.03e–07 |
| 52) | PLXC1 | O60486 | 36 | | 9.1e–08 | 6.03e–07 |
| 53) | I-TAC | O14625 | | 38 | 1.1e–07 | 6.41e–07 |
| 54) | CYTF | O76096 | | 37 | 1.1e–07 | 6.41e–07 |
| 55) | BPI | P17213 | | 36 | 1.1e–07 | 6.41e–07 |
| 56) | HNRPQ | O60506 | | 36 | 1.1e–07 | 6.41e–07 |
| 57) | PHI | P06744 | | 36 | 1.1e–07 | 6.41e–07 |
| 58) | Cathepsin G | P08311 | | 36 | 1.1e–07 | 6.47e–07 |
| 59) | Osteoblast-specific transcription factor 2 | Q13950 | 37 | | 1.1e–07 | 6.47e–07 |
| 60) | SAA | P02735 | | 38 | 1.1e–07 | 6.47e–07 |
| 61) | TXD12 | O95881 | | 36 | 1.1e–07 | 6.47e–07 |
| 62) | gp130, soluble | P40189 | 36 | | 1.2e–07 | 6.87e–07 |
| 63) | ITI heavy chain H4 | Q14624 | | 36 | 1.3e–07 | 7.30e–07 |
| 64) | CDK8/cyclin C | P49336, P24863 | | 36 | 1.4e–07 | 7.63e–07 |
| 65) | VEGF121 | P15692 | | 38 | 1.4e–07 | 7.63e–07 |
| 66) | LRIG3 | Q6UXM1 | 36 | | 1.5e–07 | 7.98e–07 |
| 67) | MAPK14 | Q16539 | | 36 | 1.5e–07 | 7.98e–07 |
| 68) | PGRP-S | O75594 | | 36 | 1.7e–07 | 8.24e–07 |
| 69) | RGM-C | Q6ZVN8 | 36 | | 1.7e–07 | 8.24e–07 |
| 70) | Fibrinogen g-chain dimer | P02679 | | 37 | 1.7e–07 | 8.24e–07 |
| 71) | MMP-9 | P14780 | | 36 | 1.8e–07 | 8.52e–07 |
| 72) | Thyroxine-Binding Globulin | P05543 | 35 | | 1.8e–07 | 8.52e–07 |
| 73) | Cadherin-5 | P33151 | 35 | | 1.8e–07 | 8.52e–07 |
| 74) | NPS-PLA2 | P14555 | | 37 | 1.9e–07 | 9.07e–07 |
| 75) | NAP-2 | P02775 | | 36 | 2.1e–07 | 9.51e–07 |
| 76) | FN1.3 | P02751 | 34 | | 2.1e–07 | 9.51e–07 |
| 77) | Protease nexin I | P07093 | | 38 | 2.3e–07 | 9.99e–07 |
| 78) | Plasminogen | P00747 | 34 | | 2.3e–07 | 9.99e–07 |

[a]Swiss Prot is a large protein sequence database widely used for protein resources
[b]Number of patients showing up or down-regulation

TABLE 2

Differential protein expression between baseline and week 8 in paired samples from n = 39 patients treated for pulmonary TB.

| Rank | Target | Swiss Prot[a] | Intrasubject Shift[b] (baseline to week 8) | | p-value | q-value |
|---|---|---|---|---|---|---|
| | | | Up (n) | Down | | |
| 1) | TIMP-2 | P16035 | 39 | | 5.3e–08 | 5.48e–07 |
| 2) | GFRα-2 | O00451 | 39 | | 5.3e–08 | 5.48e–07 |
| 3) | MRC2 | Q9UBG0 | 39 | | 5.3e–08 | 5.48e–07 |
| 4) | Haptvoglobin, Mixed | P00738 | | 39 | 5.3e–08 | 5.48e–07 |
| 5) | LBP | P18428 | | 39 | 5.3e–08 | 5.48e–07 |
| 6) | amyloid precursor protein | P05067 | | 39 | 5.3e–08 | 5.48e–07 |
| 7) | BGH3 | Q15582 | 39 | | 5.3e–08 | 5.48e–07 |
| 8) | TSP4 | P35443 | 39 | | 5.3e–08 | 5.48e–07 |
| 9) | FETUB | Q9UGM5 | 39 | | 5.3e–08 | 5.48e–07 |
| 10) | PCI | P05154 | 39 | | 5.3e–08 | 5.48e–07 |
| 11) | Kallistatin | P29622 | 39 | | 5.3e–08 | 5.48e–07 |
| 12) | α2-HS-Glycoprotein | P02765 | 39 | | 5.3e–08 | 5.48e–07 |
| 13) | CHL1 | O00533 | 39 | | 5.3e–08 | 5.48e–07 |
| 14) | CDON | Q4KMG0 | 39 | | 5.3e–08 | 5.48e–07 |
| 15) | D-dimer | P02671, | | 39 | 5.3e–08 | 5.48e–07 |
| 16) | MMP-1 | P03956 | | 39 | 5.3e–08 | 5.48e–07 |
| 17) | contactin-1 | Q12860 | 38 | | 5.7e–08 | 5.48e–07 |
| 18) | CD109 | Q6YHK3 | 38 | | 5.7e–08 | 5.48e–07 |
| 19) | IGFBP-7 | Q16270 | 38 | | 5.7e–08 | 5.48e–07 |
| 20) | Sphingosine kinase 1 | Q9NYA1 | | 38 | 5.7e–08 | 5.48e–07 |
| 21) | CRP | P02741 | | 38 | 5.7e–08 | 5.48e–07 |

TABLE 2-continued

Differential protein expression between baseline and week 8 in paired samples from n = 39 patients treated for pulmonary TB.

| Rank | Target | Swiss Prot[a] | Intrasubject Shift[b] (baseline to week 8) Up (n) | Down | p-value | q-value |
|---|---|---|---|---|---|---|
| 22) | SEPR | Q12884 | 38 | | 5.7e−08 | 5.48e−07 |
| 23) | TIMP-3 | P35625 | | 38 | 6.1e−08 | 5.48e−07 |
| 24) | Lipocalin 2 | P80188 | | 38 | 6.1e−08 | 5.48e−07 |
| 25) | NAP-2 | P02775 | | 38 | 6.1e−08 | 5.48e−07 |
| 26) | Nectin-like protein 2 | Q9BY67 | 38 | | 6.1e−08 | 5.48e−07 |
| 27) | Proteinase-3 | P24158 | | 38 | 6.1e−08 | 5.48e−07 |
| 28) | PDGF-BB | P01127 | | 38 | 6.1e−08 | 5.48e−07 |
| 29) | MMP-2 | P08253 | 38 | | 6.1e−08 | 5.48e−07 |
| 30) | TIMP-1 | P01033 | | 37 | 6.6e−08 | 5.48e−07 |
| 31) | ROR1 | Q01973 | 37 | | 6.6e−08 | 5.48e−07 |
| 32) | IGFBP-6 | P24592 | 37 | | 6.6e−08 | 5.48e−07 |
| 33) | PAI-1 | P05121 | | 38 | 6.6e−08 | 5.48e−07 |
| 34) | Protein C | P04070 | 37 | | 6.6e−08 | 5.48e−07 |
| 35) | C9 | P02748 | | 38 | 6.6e−08 | 5.48e−07 |
| 36) | GDF-9 | O60383 | | 37 | 6.6e−08 | 5.48e−07 |
| 37) | Carbonic anhydrase 6 | P23280 | 37 | | 6.6e−08 | 5.48e−07 |
| 38) | RBP | P02753 | 37 | | 6.6e−08 | 5.48e−07 |
| 39) | Albumin | P02768 | 38 | | 6.6e−08 | 5.48e−07 |
| 40) | Fibronectin | P02751 | 37 | | 6.6e−08 | 5.48e−07 |
| 41) | Antithrombin III | P01008 | 38 | | 7.2e−08 | 5.48e−07 |
| 42) | a1-Antitrypsin | P01009 | | 37 | 7.2e−08 | 5.48e−07 |
| 43) | HRG | P04196 | 38 | | 7.2e−08 | 5.48e−07 |
| 44) | Angiopoietin-1 | Q15389 | | 38 | 7.8e−08 | 5.48e−07 |
| 45) | ATS13 | Q76LX8 | 37 | | 7.8e−08 | 5.48e−07 |
| 46) | Coagulation Factor VII | P08709 | 37 | | 7.8e−08 | 5.48e−07 |
| 47) | Afamin | P43652 | 38 | | 7.8e−08 | 5.48e−07 |
| 48) | TrkB | Q16620 | 37 | | 7.8e−08 | 5.48e−07 |
| 49) | GOT1 | P17174 | | 38 | 7.8e−08 | 5.48e−07 |
| 50) | Azurocidin | P20160 | | 38 | 8.4e−08 | 5.80e−07 |
| 51) | NCAM-L1 | P32004 | 38 | | 9.1e−08 | 6.03e−07 |
| 52) | PLXC1 | O60486 | 36 | | 9.1e−08 | 6.03e−07 |
| 53) | I-TAC | O14625 | | 38 | 1.1e−07 | 6.41e−07 |
| 54) | CYTF | O76096 | | 37 | 1.1e−07 | 6.41e−07 |
| 55) | BPI | P17213 | | 36 | 1.1e−07 | 6.41e−07 |
| 56) | HNRPQ | O60506 | | 36 | 1.1e−07 | 6.41e−07 |
| 57) | PHI | P06744 | | 36 | 1.1e−07 | 6.41e−07 |
| 58) | Cathepsin G | P08311 | | 36 | 1.1e−07 | 6.47e−07 |
| 59) | Osteoblast-specific | Q13950 | 37 | | 1.1e−07 | 6.47e−07 |
| 60) | SAA | P02735 | | 38 | 1.1e−07 | 6.47e−07 |
| 61) | TXD12 | O95881 | | 36 | 1.1e−07 | 6.47e−07 |
| 62) | gp130, soluble | P40189 | 36 | | 1.2e−07 | 6.87e−07 |
| 63) | ITI heavy chain H4 | Q14624 | | 36 | 1.3e−07 | 7.30e−07 |
| 64) | CDK8/cyclin C | P49336, | | 36 | 1.4e−07 | 7.63e−07 |
| 65) | VEGF121 | P15692 | | 38 | 1.4e−07 | 7.63e−07 |
| 66) | LRIG3 | Q6UXM1 | 36 | | 1.5e−07 | 7.98e−07 |
| 67) | MAPK14 | Q16539 | | 36 | 1.5e−07 | 7.98e−07 |
| 68) | PGRP-S | O75594 | | 36 | 1.7e−07 | 8.24e−07 |
| 69) | RGM-C | Q6ZVN8 | 36 | | 1.7e−07 | 8.24e−07 |
| 70) | Fibrinogen g-chain dimer | P02679 | | 37 | 1.7e−07 | 8.24e−07 |
| 71) | MMP-9 | P14780 | | 36 | 1.8e−07 | 8.52e−07 |
| 72) | Thyroxine-Binding | P05543 | 35 | | 1.8e−07 | 8.52e−07 |
| 73) | Cadherin-5 | P33151 | 35 | | 1.8e−07 | 8.52e−07 |
| 74) | NPS-PLA2 | P14555 | | 37 | 1.9e−07 | 9.07e−07 |
| 75) | NAP-2 | P02775 | | 36 | 2.1e−07 | 9.51e−07 |
| 76) | FN1.3 | P02751 | 34 | | 2.1e−07 | 9.51e−07 |
| 77) | Protease nexin I | P07093 | | 38 | 2.3e−07 | 9.99e−07 |
| 78) | Plasminogen | P00747 | 34 | | 2.3e−07 | 9.99e−07 |
| 79) | Lactoferrin | P02788 | | 36 | 2.4e−07 | 1.04e−06 |
| 80) | Dkk-4 | Q9UBT3 | 35 | | 2.4e−07 | 1.04e−06 |
| 81) | PDGF-AA | P04085 | | 36 | 2.4e−07 | 1.04e−06 |
| 82) | Gelsolin | P06396 | 33 | | 2.6e−07 | 1.10e−06 |
| 83) | Macrophage mannose | P22897 | | 35 | 2.8e−07 | 1.15e−06 |
| 84) | Alkaline phosphatase, | P05186 | | 35 | 2.8e−07 | 1.15e−06 |
| 85) | FUT5 | Q11128 | | 34 | 2.8e−07 | 1.15e−06 |
| 86) | Apo A-I | P02647 | 35 | | 3.0e−07 | 1.22e−06 |
| 87) | SDF-1a | P48061 | 35 | | 3.3e−07 | 1.27e−06 |
| 88) | MIA | Q16674 | 34 | | 3.3e−07 | 1.27e−06 |
| 89) | GDF-11 | O95390 | 37 | | 3.3e−07 | 1.27e−06 |
| 90) | VEGF | P15692 | | 37 | 3.5e−07 | 1.31e−06 |
| 91) | MPIF-1 | P55773 | | 37 | 3.5e−07 | 1.31e−06 |
| 92) | FN1.4 | P02751 | 34 | | 3.5e−07 | 1.31e−06 |

TABLE 2-continued

Differential protein expression between baseline and week 8 in paired samples from n = 39 patients treated for pulmonary TB.

| Rank | Target | Swiss Prot[a] | Intrasubject Shift[b] (baseline to week 8) | | p-value | q-value |
|---|---|---|---|---|---|---|
| | | | Up (n) | Down | | |
| 93) | Cofilin-1 | P23528 | | 36 | 3.5e-07 | 1.31e-06 |
| 94) | Contactin-4 | Q8IWV2 | 37 | | 3.8e-07 | 1.39e-06 |
| 95) | Calpain I | P07384, | | 37 | 4.1e-07 | 1.47e-06 |
| 96) | RET | P07949 | 34 | | 4.1e-07 | 1.47e-06 |
| 97) | Contactin-5 | O94779 | 35 | | 4.4e-07 | 1.53e-06 |
| 98) | LEAP-1 | P81172 | | 36 | 4.4e-07 | 1.53e-06 |
| 99) | MASP3 | P48740 | 33 | | 4.4e-07 | 1.53e-06 |
| 100) | LSAMP | Q13449 | 35 | | 4.7e-07 | 1.60e-06 |
| 101) | BMPER | Q8N8U9 | 35 | | 4.7e-07 | 1.60e-06 |
| 102) | PAFAH | Q13093 | 36 | | 4.7e-07 | 1.60e-06 |
| 103) | C2 | P06681 | | 35 | 5.1e-07 | 1.67e-06 |
| 104) | HGFA | Q04756 | 38 | | 5.1e-07 | 1.67e-06 |
| 105) | CTAP-III | P02775 | | 35 | 5.1e-07 | 1.67e-06 |
| 106) | Protein S | P07225 | | 34 | 5.4e-07 | 1.78e-06 |
| 107) | IGFBP-3 | P17936 | 33 | | 5.9e-07 | 1.84e-06 |
| 108) | HSP 90a | P07900 | | 34 | 5.9e-07 | 1.84e-06 |
| 109) | TrkC | Q16288 | 36 | | 5.9e-07 | 1.84e-06 |
| 110) | PSA-ACT | P07288, | | 36 | 5.9e-07 | 1.84e-06 |
| 111) | a2-Macroglobulin | P01023 | 33 | | 6.3e-07 | 1.95e-06 |
| 112) | IP-10 | P02778 | | 36 | 6.3e-07 | 1.95e-06 |
| 113) | resistin | Q9HD89 | 33 | | 6.8e-07 | 2.04e-06 |
| 114) | RASA1 | P20936 | | 37 | 6.8e-07 | 2.04e-06 |
| 115) | CATZ | Q9UBR2 | 34 | | 6.8e-07 | 2.04e-06 |
| 116) | ZAP70 | P43403 | | 35 | 7.8e-07 | 2.31e-06 |
| 117) | Factor B | P00751 | | 36 | 7.8e-07 | 2.31e-06 |
| 118) | TGF-b R III | Q03167 | 35 | | 8.4e-07 | 2.44e-06 |
| 119) | CAPG | P40121 | | 35 | 8.4e-07 | 2.44e-06 |
| 120) | Flt3 ligand | P49771 | | 33 | 9.0e-07 | 2.60e-06 |
| 121) | ERBB1 | P00533 | 35 | | 9.7e-07 | 2.74e-06 |
| 122) | Gro-b | P19875 | | 35 | 9.7e-07 | 2.74e-06 |
| 123) | bFGF-R | P11362 | 35 | | 1.0e-06 | 2.92e-06 |
| 124) | BMP-1 | P13497 | 36 | | 1.1e-06 | 3.09e-06 |
| 125) | Angiostatin | P00747 | 33 | | 1.1e-06 | 3.09e-06 |
| 126) | SAP | P02743 | | 34 | 1.3e-06 | 3.50e-06 |
| 127) | Coagulation Factor IX | P00740 | | 36 | 1.3e-06 | 3.50e-06 |
| 128) | IGFBP-5 | P24593 | 36 | | 1.4e-06 | 3.66e-06 |
| 129) | CNDP1 | Q96KN2 | 36 | | 1.4e-06 | 3.66e-06 |
| 130) | Cadherin-2 | P19022 | | 35 | 1.4e-06 | 3.66e-06 |
| 131) | VEGF sR3 | P35916 | | 34 | 1.5e-06 | 3.87e-06 |
| 132) | Siglec-9 | Q9Y336 | | 33 | 1.5e-06 | 3.87e-06 |
| 133) | IDUA | P35475 | 35 | | 1.7e-06 | 4.42e-06 |
| 134) | suPAR | Q03405 | | 33 | 1.8e-06 | 4.66e-06 |
| 135) | Coagulation Factor IX | P00740 | | 36 | 1.8e-06 | 4.66e-06 |
| 136) | CD30 Ligand | P32971 | 32 | | 1.9e-06 | 4.92e-06 |
| 137) | 14-3-3 eta | Q04917 | | 33 | 1.9e-06 | 4.92e-06 |
| 138) | TIG2 | Q99969 | | 34 | 2.2e-06 | 5.61e-06 |
| 139) | HGF | P14210 | | 36 | 2.4e-06 | 5.92e-06 |
| 140) | TNF sR-II | P20333 | | 33 | 2.4e-06 | 5.92e-06 |
| 141) | Factor I | P05156 | | 37 | 2.6e-06 | 6.13e-06 |
| 142) | OLR1 | P78380 | | 33 | 2.6e-06 | 6.13e-06 |
| 143) | Thrombin | P00734 | | 31 | 2.6e-06 | 6.13e-06 |
| 144) | Collectin Kidney 1 | Q9BWP8 | 35 | | 2.6e-06 | 6.13e-06 |
| 145) | Endoglin | P17813 | 35 | | 2.6e-06 | 6.13e-06 |
| 146) | ON | P09486 | | 32 | 2.7e-06 | 6.43e-06 |
| 147) | CATC | P53634 | | 32 | 2.7e-06 | 6.43e-06 |
| 148) | DKK3 | Q9UBP4 | 32 | | 2.7e-06 | 6.43e-06 |
| 149) | Fibrinogen | P02671, | | 34 | 2.9e-06 | 6.83e-06 |
| 150) | MMP-8 | P22894 | | 34 | 3.1e-06 | 7.17e-06 |
| 151) | TPSB2 | P20231 | 33 | | 3.1e-06 | 7.17e-06 |
| 152) | CK-MB | P12277, | 33 | | 3.1e-06 | 7.17e-06 |
| 153) | BASI | P35613 | 33 | | 3.4e-06 | 7.62e-06 |
| 154) | Adiponectin | Q15848 | 33 | | 3.6e-06 | 8.10e-06 |
| 155) | Myeloperoxidase | P05164 | | 34 | 3.9e-06 | 8.44e-06 |
| 156) | Aurora kinase A | O14965 | | 34 | 3.9e-06 | 8.44e-06 |
| 157) | IL-18 Rα | Q13478 | | 32 | 3.9e-06 | 8.44e-06 |
| 158) | 14-3-3 protein gamma | P61981 | | 33 | 3.9e-06 | 8.44e-06 |
| 159) | Ck-b-8-1 | P55773 | | 35 | 4.1e-06 | 8.97e-06 |
| 160) | FCG3B | O75015 | | 33 | 4.4e-06 | 9.54e-06 |
| 161) | MIP-1a | P10147 | | 32 | 4.7e-06 | 9.95e-06 |
| 162) | TFPI | P10646 | | 32 | 4.7e-06 | 9.95e-06 |
| 163) | NCAM-120 | P13591 | 33 | | 4.7e-06 | 9.95e-06 |

TABLE 2-continued

Differential protein expression between baseline and week 8 in paired samples from n = 39 patients treated for pulmonary TB.

| Rank | Target | Swiss Prot[a] | Intrasubject Shift[b] (baseline to week 8) | | p-value | q-value |
|---|---|---|---|---|---|---|
| | | | Up (n) | Down | | |
| 164) | TSG-6 | P98066 | | 33 | 4.7e−06 | 9.95e−06 |
| 165) | HAI-1 | O43278 | 34 | | 5.0e−06 | 1.06e−05 |
| 166) | CNTFR alpha | P26992 | 31 | | 5.4e−06 | 1.10e−05 |
| 167) | Factor D | P00746 | 35 | | 5.4e−06 | 1.10e−05 |
| 168) | IL-17 RC | Q8NAC3 | | 35 | 5.4e−06 | 1.10e−05 |
| 169) | BOC | Q9BWV1 | 34 | | 5.4e−06 | 1.10e−05 |
| 170) | Spondin-1 | Q9HCB6 | 35 | | 5.8e−06 | 1.17e−05 |
| 171) | RGMB | Q6NW40 | 31 | | 6.1e−06 | 1.23e−05 |
| 172) | Lysozyme | P61626 | | 33 | 6.1e−06 | 1.23e−05 |
| 173) | C1QBP | Q07021 | | 31 | 6.1e−06 | 1.23e−05 |
| 174) | Gro-g | P19876 | | 33 | 7.0e−06 | 1.39e−05 |
| 175) | CD5L | O43866 | | 31 | 8.0e−06 | 1.55e−05 |
| 176) | MAPK2 | P49137 | | 31 | 8.0e−06 | 1.55e−05 |
| 177) | C6 | P13671 | | 33 | 8.0e−06 | 1.55e−05 |
| 178) | JAK2 | O60674 | | 33 | 8.0e−06 | 1.55e−05 |
| 179) | Apo E3 | P02649 | 34 | | 8.5e−06 | 1.65e−05 |
| 180) | Apo B | P04114 | 32 | | 9.1e−06 | 1.73e−05 |
| 181) | LYVE1 | Q9Y5Y7 | 32 | | 9.1e−06 | 1.73e−05 |
| 182) | Endocan | Q9NQ30 | | 34 | 9.1e−06 | 1.73e−05 |
| 183) | ASAHL | Q02083 | 34 | | 9.7e−06 | 1.84e−05 |
| 184) | PBEF | P43490 | | 33 | 1.0e−05 | 1.95e−05 |
| 185) | CD23 | P06734 | 35 | | 1.1e−05 | 2.07e−05 |
| 186) | WFKN2 | Q8TEU8 | 32 | | 1.2e−05 | 2.17e−05 |
| 187) | RGMA | Q96B86 | | 32 | 1.2e−05 | 2.17e−05 |
| 188) | ENTP3 | O75355 | | 35 | 1.2e−05 | 2.17e−05 |
| 189) | PF-4 | P02776 | | 31 | 1.3e−05 | 2.29e−05 |
| 190) | HPG- | P15428 | | 31 | 1.3e−05 | 2.29e−05 |
| 191) | ZAP70 | P43403 | | 34 | 1.3e−05 | 2.42e−05 |
| 192) | Cystatin C | P01034 | 31 | | 1.4e−05 | 2.56e−05 |
| 193) | C3d | P01024 | | 33 | 1.4e−05 | 2.56e−05 |
| 194) | AIF1 | P55008 | | 34 | 1.5e−05 | 2.67e−05 |
| 195) | URB | Q76M96 | 33 | | 1.5e−05 | 2.67e−05 |
| 196) | GSK-3 beta | P49841 | | 32 | 1.5e−05 | 2.67e−05 |
| 197) | MATN2 | O00339 | | 33 | 1.5e−05 | 2.67e−05 |
| 198) | Ephrin-A5 | P52803 | 32 | | 1.6e−05 | 2.83e−05 |
| 199) | CYTD | P28325 | 35 | | 1.8e−05 | 3.16e−05 |
| 200) | HDGR2 | Q7Z4V5 | | 32 | 1.8e−05 | 3.16e−05 |
| 201) | PH | P01298 | | 35 | 1.8e−05 | 3.16e−05 |
| 202) | TNF sR-I | P19438 | | 30 | 2.0e−05 | 3.28e−05 |
| 203) | IL-2 sRa | P01589 | | 34 | 2.0e−05 | 3.28e−05 |
| 204) | IFN-g R1 | P15260 | 33 | | 2.0e−05 | 3.28e−05 |
| 205) | DHH | O43323 | | 32 | 2.0e−05 | 3.28e−05 |
| 206) | Coactosin-like protein | Q14019 | | 32 | 2.0e−05 | 3.28e−05 |
| 207) | SCF sR | P10721 | 34 | | 2.1e−05 | 3.46e−05 |
| 208) | HSP 70 | P08107 | | 34 | 2.1e−05 | 3.46e−05 |
| 209) | IL-13 | P35225 | 34 | | 2.2e−05 | 3.65e−05 |
| 210) | DKK1 | O94907 | | 34 | 2.2e−05 | 3.65e−05 |
| 211) | M-CSF R | P07333 | 31 | | 2.4e−05 | 3.84e−05 |
| 212) | Bcl-2 | P10415 | | 31 | 2.4e−05 | 3.84e−05 |
| 213) | TARC | Q92583 | | 32 | 2.5e−05 | 4.07e−05 |
| 214) | Apo E | P02649 | 33 | | 2.7e−05 | 4.23e−05 |
| 215) | CD36 ANTIGEN | P16671 | 33 | | 2.7e−05 | 4.23e−05 |
| 216) | IL-19 | Q9UHD0 | 34 | | 2.7e−05 | 4.23e−05 |
| 217) | Kininogen, HMW, Single | P01042 | 32 | | 2.7e−05 | 4.23e−05 |
| 218) | IL-1a | P01583 | | 33 | 2.7e−05 | 4.23e−05 |
| 219) | Apo E4 | P02649 | 33 | | 2.8e−05 | 4.48e−05 |
| 220) | SDF-1b | P48061 | 32 | | 3.4e−05 | 5.33e−05 |
| 221) | Macrophage scavenger | P21757 | | 33 | 3.4e−05 | 5.33e−05 |
| 222) | Midkine | P21741 | | 31 | 3.6e−05 | 5.59e−05 |
| 223) | IGF-I | P05019 | 30 | | 3.6e−05 | 5.59e−05 |
| 224) | AK1A1 | P14550 | | 33 | 3.6e−05 | 5.59e−05 |
| 225) | EDAR | Q9UNE0 | 31 | | 4.1e−05 | 6.25e−05 |
| 226) | Hemoglobin | P69905, | 33 | | 4.1e−05 | 6.25e−05 |
| 227) | GP1BA | P07359 | | 32 | 4.3e−05 | 6.61e−05 |
| 228) | BARK1 | P25098 | | 31 | 4.6e−05 | 6.99e−05 |
| 229) | Calpastatin | P20810 | 30 | | 5.2e−05 | 7.81e−05 |
| 230) | OBCAM | Q14982 | | 30 | 5.2e−05 | 7.81e−05 |
| 231) | Growth hormone receptor | P10912 | 32 | | 5.5e−05 | 8.25e−05 |
| 232) | pTEN | P60484 | | 33 | 5.8e−05 | 8.68e−05 |
| 233) | IF4G2 | P78344 | | 31 | 5.8e−05 | 8.68e−05 |
| 234) | GASP-2 | Q96D09 | 31 | | 6.2e−05 | 9.06e−05 |

TABLE 2-continued

Differential protein expression between baseline and week 8 in paired samples from n = 39 patients treated for pulmonary TB.

| Rank | Target | Swiss Prot[a] | Intrasubject Shift[b] (baseline to week 8) | | p-value | q-value |
|---|---|---|---|---|---|---|
| | | | Up (n) | Down | | |
| 235) | Cystatin M | Q15828 | 29 | | 6.2e−05 | 9.06e−05 |
| 236) | dopa decarboxylase | P20711 | 34 | | 6.2e−05 | 9.06e−05 |
| 237) | LCMT1 | Q9UIC8 | | 30 | 6.2e−05 | 9.06e−05 |
| 238) | Myoglobin | P02144 | | 30 | 6.6e−05 | 9.53e−05 |
| 239) | NRP1 | O14786 | | 32 | 6.6e−05 | 9.53e−05 |

[a]Swiss Prot is a large protein sequence database widely used for protein resources
[b]Number of patients showing up or down-regulation

TABLE 3

DAVID analysis - Paired sample data set

| Annotation Cluster | p-value (Bonferroni Corrected) |
|---|---|
| Enrichment Score: 83.01749576763416 | |
| signal | 6.01E−94 |
| signal peptide | 4.54E−93 |
| disulfide bond | 7.85E−69 |
| disulfide bond | 4.23E−68 |
| Enrichment Score: 58.445486770722454 | |
| Secreted | 6.48E−71 |
| GO: 0005576~extracellular region | 5.14E−59 |
| GO: 0005615~extracellular space | 1.36E−49 |
| GO: 0044421~extracellular region part | 1.49E−47 |
| Enrichment Score: 28.642746811176313 | |
| GO: 0009611~response to wounding | 1.73E−36 |
| GO: 0006952~defense response | 4.33E−22 |
| GO: 0006954~inflammatory response | 1.61E−19 |
| Enrichment Score: 16.859976579934965 | |
| hsa04610: Complement and coagulation cascades | 1.89E−20 |
| GO: 0042060~wound healing | 2.47E−16 |
| GO: 0007599~hemostasis | 1.63E−15 |
| blood coagulation | 3.19E−16 |
| GO: 0007596~blood coagulation | 8.30E−15 |
| GO: 0050817~coagulation | 8.30E−15 |
| GO: 0050878~regulation of body fluid levels | 7.23E−13 |
| GO: 0030168~platelet activation | 4.89E−05 |
| Enrichment Score: 14.250642339320128 | |
| GO: 0002526~acute inflammatory response | 6.45E−14 |
| acute phase | 3.88E−12 |
| GO: 0006953~acute-phase response | 1.18E−09 |
| Enrichment Score: 13.460056934270545 | |
| GO: 0005539~glycosaminoglycan binding | 5.38E−13 |
| GO: 0030246~carbohydrate binding | 2.98E−12 |
| GO: 0030247~polysaccharide binding | 3.73E−12 |
| GO: 0001871~pattern binding | 3.73E−12 |
| GO: 0008201~heparin binding | 5.83E−11 |
| heparin-binding | 3.48E−09 |
| Enrichment Score: 12.995486525261226 | |
| GO: 0031983~vesicle lumen | 2.66E−23 |
| GO: 0060205~cytoplasmic membrane-bounded vesicle lumen | 4.44E−22 |
| GO: 0031091~platelet alpha granule | 1.64E−19 |
| GO: 0031093~platelet alpha granule lumen | 2.13E−19 |
| GO: 0030141~secretory granule | 7.15E−15 |
| GO: 0044433~cytoplasmic vesicle part | 2.12E−12 |
| GO: 0031988~membrane-bounded vesicle | 1.13E−07 |
| GO: 0016023~cytoplasmic membrane-bounded vesicle | 2.06E−07 |
| GO: 0031982~vesicle | 1.95E−06 |
| GO: 0031410~cytoplasmic vesicle | 8.62E−06 |
| Enrichment Score: 11.192778045345973 | |
| domain: Peptidase S1 | 4.97E−12 |
| GO: 0004252~serine-type endopeptidase activity | 3.73E−12 |
| IPR001314: Peptidase S1A, chymotrypsin | 1.24E−11 |
| GO: 0004175~endopeptidase activity | 1.39E−11 |
| GO: 0008236~serine-type peptidase activity | 7.06E−11 |
| IPR001254: Peptidase S1 and S6, chymotrypsin/Hap | 8.01E−11 |
| GO: 0017171~serine hydrolase activity | 8.84E−11 |
| zymogen | 1.21E−10 |
| serine proteinase | 3.31E−10 |
| Protease | 8.38E−10 |
| GO: 0008233~peptidase activity | 1.37E−09 |
| Serine protease | 1.58E−09 |
| IPR018114: Peptidase S1/S6, chymotrypsin/Hap, active site | 3.20E−09 |
| SM00020: Tryp_SPc | 7.34E−09 |
| GO: 0070011~peptidase activity, acting on L-amino acid peptides | 4.66E−08 |
| active site: Charge relay system | 1.12E−06 |
| GO: 0006508~proteolysis | 0.029938092 |
| hydrolase | 0.016036551 |
| Enrichment Score: 10.955845478585891 | |
| GO: 0004866~endopeptidase inhibitor activity | 1.49E−18 |
| GO: 0030414~peptidase inhibitor activity | 6.20E−18 |
| GO: 0004857~enzyme inhibitor activity | 1.28E−12 |
| protease inhibitor | 2.06E−12 |
| GO: 0004867~serine-type endopeptidase inhibitor activity | 1.99E−09 |
| Serine protease inhibitor | 2.58E−09 |
| site: Reactive bond | 7.46E−08 |
| serine proteinase inhibitor | 1.30E−06 |
| IPR000215: Protease inhibitor I4, serpin | 3.35E−04 |
| PIRSF001630: serpin | 5.94E−04 |
| GO: 0002020~protease binding | 0.002520743 |
| SM00093: SERPIN | 0.001060892 |
| Enrichment Score: 8.121728432887654 | |
| cell adhesion | 1.50E−06 |
| GO: 0007155~cell adhesion | 2.16E−05 |
| GO: 0022610~biological adhesion | 2.23E−05 |
| Enrichment Score: 7.857494699405822 | |
| GO: 0051241~negative regulation of multicellular organismal process | 1.70E−07 |
| GO: 0030195~negative regulation of blood coagulation | 2.57E−06 |
| GO: 0030193~regulation of blood coagulation | 6.27E−06 |

TABLE 3-continued

DAVID analysis - Paired sample data set

| Annotation Cluster | p-value (Bonferroni Corrected) |
|---|---|
| GO: 0050819~negative regulation of coagulation | 7.87E−06 |
| GO: 0050818~regulation of coagulation | 2.18E−05 |
| Enrichment Score: 6.887800010777238 | |
| | |
| hsa04060: Cytokine-cytokine receptor interaction | 3.34E−11 |
| GO: 0005125~cytokine activity | 4.31E−10 |
| cytokine | 1.27E−09 |
| GO: 0006935~chemotaxis | 9.75E−07 |
| GO: 0042330~taxis | 9.75E−07 |
| IPR001811: Small chemokine, interleukin-8-like | 1.03E−06 |
| chemotaxis | 3.51E−06 |
| inflammatory response | 6.83E−06 |
| GO: 0008009~chemokine activity | 7.52E−06 |
| GO: 0042379~chemokine receptor binding | 1.35E−05 |
| IPR018048: Small chemokine, C—X—C, conserved site | 2.22E−05 |
| SM00199: SCY | 6.93E−06 |
| PIRSF002522: CXC chemokine | 2.86E−05 |
| GO: 0007626~locomotory behavior | 5.85E−04 |
| IPR001089: Small chemokine, C—X—C | 1.85E−04 |
| GO: 0007610~behavior | 0.008360072 |
| IPR002473: Small chemokine, C—X—C/ Interleukin 8 | 0.010862324 |
| Enrichment Score: 6.760362997866251 | |
| | |
| domain: Ig-like C2-type 1 | 8.09E−10 |
| domain: Ig-like C2-type 2 | 8.88E−10 |
| IPR003598: Immunoglobulin subtype 2 | 1.24E−08 |
| IPR013098: Immunoglobulin I-set | 1.64E−08 |
| Immunoglobulin domain | 1.46E−08 |
| domain: Ig-like C2-type 3 | 1.39E−07 |
| IPR013151: Immunoglobulin | 8.02E−08 |
| domain: Ig-like C2-type 5 | 1.20E−05 |
| SM00408: IGc2 | 1.51E−06 |
| domain: Ig-like C2-type 4 | 1.63E−05 |
| IPR007110: Immunoglobulin-like | 2.15E−05 |
| IPR013783: Immunoglobulin-like fold | 1.34E−04 |
| IPR003599: Immunoglobulin subtype | 1.71E−04 |
| domain: Fibronectin type-III 2 | 0.002634843 |
| domain: Fibronectin type-III 1 | 0.00282371 |
| domain: Fibronectin type-III 3 | 0.004969958 |
| IPR008957: Fibronectin, type III-like fold | 0.01383263 |
| Enrichment Score: 6.513631012511141 | |
| | |
| GO: 0030334~regulation of cell migration | 3.24E−08 |
| GO: 0040012~regulation of locomotion | 3.80E−08 |
| GO: 0051270~regulation of cell motion | 3.32E−07 |
| GO: 0040017~positive regulation of locomotion | 6.87E−07 |
| GO: 0030335~positive regulation of cell migration | 2.27E−06 |
| GO: 0051272~positive regulation of cell motion | 7.66E−06 |
| GO: 0008284~positive regulation of cell proliferation | 2.59E−04 |
| Enrichment Score: 6.382973768072646 | |
| | |
| gpi-anchor | 7.76E−08 |
| propeptide: Removed in mature form | 1.05E−05 |
| lipoprotein | 0.001999218 |
| GO: 0031225~anchored to membrane | 0.005219445 |
| lipid moiety-binding region: GPI-anchor amidated serine | 0.03344798 |
| Enrichment Score: 6.381892989930859 | |
| | |
| GO: 0050727~regulation of inflammatory response | 1.19E−09 |
| GO: 0031348~negative regulation of defense response | 0.002426561 |
| GO: 0050728~negative regulation of inflammatory response | 0.014941367 |
| Enrichment Score: 5.766209887182889 | |
| | |
| GO: 0048589~developmental growth | 0.002009295 |
| GO: 0040007~growth | 0.002141443 |
| GO: 0031099~regeneration | 0.002418875 |
| GO: 0042246~tissue regeneration | 0.018123619 |
| Enrichment Score: 5.093484237271428 | |
| | |
| GO: 0030334~regulation of cell migration | 3.24E−08 |
| GO: 0051270~regulation of cell motion | 3.32E−07 |
| GO: 0014910~regulation of smooth muscle cell migration | 2.42E−05 |
| Enrichment Score: 5.03912245884617 | |
| | |
| GO: 0043067~regulation of programmed cell death | 7.06E−05 |
| GO: 0010941~regulation of cell death | 7.74E−05 |
| GO: 0042981~regulation of apoptosis | 1.81E−04 |
| GO: 0043069~negative regulation of programmed cell death | 0.02653394 |
| GO: 0060548~negative regulation of cell death | 0.027885969 |
| Enrichment Score: 5.007846862267697 | |
| | |
| Antimicrobial | 5.64E−04 |
| GO: 0042742~defense response to bacterium | 0.020111498 |
| antibiotic | 0.004714378 |
| Enrichment Score: 4.847304827557594 | |
| | |
| GO: 0007584~response to nutrient | 0.003955906 |
| GO: 0048545~response to steroid hormone stimulus | 0.019987437 |
| GO: 0031667~response to nutrient levels | 0.026212926 |
| Enrichment Score: 4.652312171554018 | |
| | |
| glycosylation site: N-linked (Glc) (glycation) | 1.01E−05 |
| glycation | 3.05E−05 |
| Enrichment Score: 4.569289937199638 | |
| | |
| GO: 0031012~extracellular matrix | 0.005426686 |
| extracellular matrix | 0.008814367 |
| GO: 0005578~proteinaceous extracellular matrix | 0.007324162 |
| Enrichment Score: 4.441341170694785 | |
| | |
| GO: 0002526~acute inflammatory response | 6.45E−14 |
| GO: 0048584~positive regulation of response to stimulus | 3.27E−08 |
| GO: 0002684~positive regulation of immune system process | 6.92E−05 |
| GO: 0006959~humoral immune response | 7.56E−05 |
| GO: 0006956~complement activation | 4.80E−04 |
| GO: 0002541~activation of plasma proteins involved in acute inflammatory response | 5.82E−04 |
| GO: 0050778~positive regulation of immune response | 8.69E−04 |
| GO: 0002252~immune effector process | 0.016200769 |
| GO: 0016485~protein processing | 0.020111498 |
| GO: 0045087~innate immune response | 0.021422415 |
| complement alternate pathway | 0.004054285 |
| GO: 0002253~activation of immune response | 0.031999554 |
| complement pathway | 0.006599395 |
| GO: 0051604~protein maturation | 0.042326373 |
| innate immunity | 0.011613247 |
| h_alternativePathway: Alternative Complement Pathway | 0.011241058 |
| IPR016060: Complement control module | 0.04106339 |
| h_compPathway: Complement Pathway | 0.021008529 |
| Enrichment Score: 4.130616183620647 | |
| | |
| IPR000010: Proteinase inhibitor I25, cystatin | 3.30E−05 |
| SM00043: CY | 7.98E−05 |
| domain: Cystatin 1 | 0.005588456 |
| domain: Cystatin 2 | 0.005588456 |
| GO: 0004869~cysteine-type endopeptidase inhibitor activity | 0.005881805 |
| Enrichment Score: 4.052462047448763 | |
| | |
| GO: 0042592~homeostatic process | 1.17E−04 |
| GO: 0048878~chemical homeostasis | 8.30E−04 |

TABLE 3-continued

DAVID analysis - Paired sample data set

| Annotation Cluster | | p-value (Bonferroni Corrected) |
|---|---|---|
| | GO: 0030005~cellular di-, tri-valent inorganic cation homeostasis | 0.026234271 |
| | GO: 0055066~di-, tri-valent inorganic cation homeostasis | 0.046516885 |
| | Enrichment Score: 4.041695851166527 | |
| | GO: 0001501~skeletal system development | 0.02123564 |
| | GO: 0001503~ossification | 0.025372783 |
| | GO: 0060348~bone development | 0.045384573 |
| | Enrichment Score: 3.9213291824047216 | |
| | IPR000562: Type II fibronectin, collagen-binding | 2.85E−04 |
| | SM00059: FN2 | 4.81E−04 |
| | Enrichment Score: 3.8727407217543153 | |
| | GO: 0006928~cell motion | 1.15E−05 |
| | Enrichment Score: 3.7683817948224463 | |
| | GO: 0051050~positive regulation of transport | 0.00444447 |
| | GO: 0051222~positive regulation of protein transport | 0.018855521 |
| | GO: 0032880~regulation of protein localization | 0.021422415 |
| | Enrichment Score: 3.6480936797487855 | |
| | growth factor | 1.41E−05 |
| | mitogen | 9.96E−05 |
| | Enrichment Score: 3.638806829653257 | |
| | kringle | 0.016478159 |
| | IPR018059: Kringle, subgroup | 0.019261763 |
| | IPR018056: Kringle, conserved site | 0.031522348 |
| | IPR000001: Kringle | 0.031522348 |
| | SM00130: KR | 0.03548799 |
| | Enrichment Score: 3.5255469961665273 | |
| | GO: 0010033~response to organic substance | 1.24E−05 |
| | GO: 0009725~response to hormone stimulus | 0.009694324 |
| | GO: 0009719~response to endogenous stimulus | 0.010969202 |
| | GO: 0048545~response to steroid hormone stimulus | 0.019987437 |
| | Enrichment Score: 3.4007875204513938 | |
| | GO: 0014910~regulation of smooth muscle cell migration | 2.42E−05 |
| | Enrichment Score: 3.3534540539683504 | |
| | metalloprotease inhibitor | 0.028637424 |
| | metalloenzyme inhibitor | 0.042292475 |
| | Enrichment Score: 3.3314605750410893 | |
| | GO: 0034358~plasma lipoprotein particle | 0.005392824 |
| | GO: 0032994~protein-lipid complex | 0.005392824 |
| | Enrichment Score: 3.2795760321542433 | |
| | h_amiPathway: Acute Myocardial Infarction | 1.78E−04 |
| | gamma-carboxyglutamic acid | 7.12E−04 |
| | beta-hydroxyaspartic acid | 7.42E−04 |
| | carboxyglutamic acid | 7.42E−04 |
| | calcium binding | 0.001081267 |
| | h_extrinsicPathway: Extrinsic Prothrombin Activation Pathway | 0.001023605 |
| | IPR002383: Coagulation factor, Gla region | 0.005499108 |
| | domain: Gla | 0.014684251 |
| | IPR000294: Gamma-carboxyglutamic acid-rich (GLA) domain | 0.010862324 |
| | vitamin K | 0.018148778 |
| | thrombophilia | 0.018148778 |
| | SM00069: GLA | 0.012479961 |
| | h_intrinsicPathway: Intrinsic Prothrombin Activation Pathway | 0.021008529 |
| | Enrichment Score: 3.2363675396592373 | |
| | GO: 0040007~growth | 0.002141443 |
| | Enrichment Score: 2.8661130704947184 | |
| | GO: 0010035~response to inorganic substance | 0.001535929 |
| | Enrichment Score: 2.8570723350751956 | |
| | GO: 0007167~enzyme linked receptor protein signaling pathway | 3.72E−05 |
| | tyrosine-specific protein kinase | 2.51E−05 |
| | IPR008266: Tyrosine protein kinase, active site | 2.48E−04 |
| | phosphotransferase | 2.27E−04 |
| | tyrosine-protein kinase | 2.28E−04 |
| | ATP | 2.37E−04 |
| | GO: 0007169~transmembrane receptor protein tyrosine kinase signaling pathway | 0.004712502 |
| | IPR001245: Tyrosine protein kinase | 0.001511608 |
| | GO: 0004714~transmembrane receptor protein tyrosine kinase activity | 0.002367407 |
| | SM00219: TyrKc | 0.009888893 |
| | Enrichment Score: 2.832111814427249 | |
| | GO: 0010743~regulation of foam cell differentiation | 0.003906039 |
| | GO: 0034381~lipoprotein particle clearance | 0.007062906 |
| | Enrichment Score: 2.632089925155713 | |
| | extracellular matrix | 0.008814367 |
| | Enrichment Score: 2.589728231561291 | |
| | GO: 0030162~regulation of proteolysis | 0.035240925 |
| | Enrichment Score: 2.541055191143139 | |
| | calcium | 5.08E−06 |
| | GO: 0005509~calcium ion binding | 0.005178201 |
| | Enrichment Score: 2.536907630353502 | |
| | propeptide: Activation peptide | 1.52E−04 |
| | metal ion-binding site: Calcium 1 | 0.011635726 |
| | collagen degradation | 0.012956123 |
| | metal ion-binding site: Calcium 2 | 0.037112738 |
| | Enrichment Score: 1.8866108235227257 | |
| | GO: 0014910~regulation of smooth muscle cell migration | 2.42E−05 |
| | Enrichment Score: 1.6588499771985241 | |
| | GO: 0034381~lipoprotein particle clearance | 0.007062906 |
| | GO: 0034358~plasma lipoprotein particle | 0.005392824 |
| | GO: 0032994~protein-lipid complex | 0.005392824 |
| | Enrichment Score: 1.3901891582691086 | |
| | GO: 0005577~fibrinogen complex | 0.035496696 |

TABLE 4

Unpaired analysis of proteins showing differential expression between baseline and week 8 in n = 39 TB patients.

| Target | Swiss Prot* | KS-distance (Signed) | p-value | q-value |
|---|---|---|---|---|
| 1) TSP4 | P35443 | 0.821 | 1.37e−12 | 1.06e−09 |
| 2) SEPR | Q12884 | 0.769 | 4.08e−11 | 1.05e−08 |
| 3) MRC2 | Q9UBG0 | 0.769 | 4.08e−11 | 1.05e−08 |
| 4) Antithrombin III | P01008 | 0.744 | 2.05e−10 | 3.15e−08 |
| 5) PCI | P05154 | 0.744 | 2.05e−10 | 3.15e−08 |
| 6) LBP | P18428 | −0.718 | 9.73e−10 | 6.25e−08 |
| 7) a2-HS-Glycoprotein | P02765 | 0.718 | 9.73e−10 | 6.25e−08 |
| 8) NPS-PLA2 | P14555 | −0.718 | 9.73e−10 | 6.25e−08 |
| 9) Haptoglobin, Mixed Type | P00738 | −0.718 | 9.73e−10 | 6.25e−08 |
| 10) Kallistatin | P29622 | 0.718 | 9.73e−10 | 6.25e−08 |
| 11) MMP-2 | P08253 | 0.718 | 9.73e−10 | 6.25e−08 |
| 12) NCAM-L1 | P32004 | 0.718 | 9.73e−10 | 6.25e−08 |
| 13) CDON | Q4KMG0 | 0.692 | 4.38e−09 | 2.60e−07 |
| 14) Fibronectin | P02751 | 0.667 | 1.87e−08 | 1.03e−06 |
| 15) Cathepsin G | P08311 | −0.641 | 7.53e−08 | 2.23e−06 |
| 16) gp130, soluble | P40189 | 0.641 | 7.53e−08 | 2.23e−06 |
| 17) Nectin-like protein 2 | Q9BY67 | 0.641 | 7.53e−08 | 2.23e−06 |
| 18) LEAP-1 | P81172 | −0.641 | 7.53e−08 | 2.23e−06 |
| 19) CRP | P02741 | −0.641 | 7.53e−08 | 2.23e−06 |
| 20) Fibrinogen g-chain dimer | P02679 | −0.641 | 7.53e−08 | 2.23e−06 |
| 21) TIMP-2 | P16035 | 0.641 | 7.53e−08 | 2.23e−06 |
| 22) IL-19 | Q9UHD0 | 0.641 | 7.53e−08 | 2.23e−06 |
| 23) CDK8/cyclin C | P49336, P24863 | −0.641 | 7.53e−08 | 2.23e−06 |
| 24) CHL1 | O00533 | 0.641 | 7.53e−08 | 2.23e−06 |
| 25) D-dimer | P02671, P02675, P02679 | −0.641 | 7.53e−08 | 2.23e−06 |
| 26) CATZ | Q9UBR2 | 0.641 | 7.53e−08 | 2.23e−06 |
| 27) TrkC | Q16288 | 0.615 | 2.88e−07 | 7.15e−06 |
| 28) Fibrinogen | P02671, P02675, P02679 | −0.615 | 2.88e−07 | 7.15e−06 |
| 29) Angiopoietin-1 | Q15389 | −0.615 | 2.88e−07 | 7.15e−06 |
| 30) Lipocalin 2 | P80188 | −0.615 | 2.88e−07 | 7.15e−06 |
| 31) C9 | P02748 | −0.615 | 2.88e−07 | 7.15e−06 |
| 32) MMP-9 | P14780 | −0.590 | 1.04e−06 | 1.82e−05 |
| 33) I-TAC | O14625 | −0.590 | 1.04e−06 | 1.82e−05 |
| 34) BMP-1 | P13497 | 0.590 | 1.04e−06 | 1.82e−05 |
| 35) BMPER | Q8N8U9 | 0.590 | 1.04e−06 | 1.82e−05 |
| 36) Plasminogen | P00747 | 0.590 | 1.04e−06 | 1.82e−05 |
| 37) PHI | P06744 | −0.590 | 1.04e−06 | 1.82e−05 |
| 38) TrkB | Q16620 | 0.590 | 1.04e−06 | 1.82e−05 |
| 39) Coagulation Factor IX | P00740 | −0.590 | 1.04e−06 | 1.82e−05 |
| 40) GOT1 | P17174 | −0.590 | 1.04e−06 | 1.82e−05 |
| 41) RBP | P02753 | 0.590 | 1.04e−06 | 1.82e−05 |
| 42) Albumin | P02768 | 0.590 | 1.04e−06 | 1.82e−05 |
| 43) Sphingosine kinase 1 | Q9NYA1 | −0.590 | 1.04e−06 | 1.82e−05 |
| 44) Afamin | P43652 | 0.590 | 1.04e−06 | 1.82e−05 |
| 45) TIMP-1 | P01033 | −0.564 | 3.56e−06 | 4.58e−05 |
| 46) GFRa-2 | O00451 | 0.564 | 3.56e−06 | 4.58e−05 |
| 47) Azurocidin | P20160 | −0.564 | 3.56e−06 | 4.58e−05 |
| 48) Lactoferrin | P02788 | −0.564 | 3.56e−06 | 4.58e−05 |
| 49) amyloid precursor protein | P05067 | −0.564 | 3.56e−06 | 4.58e−05 |
| 50) RET | P07949 | 0.564 | 3.56e−06 | 4.58e−05 |
| 51) LRIG3 | Q6UXM1 | 0.564 | 3.56e−06 | 4.58e−05 |
| 52) CD30 Ligand | P32971 | 0.564 | 3.56e−06 | 4.58e−05 |
| 53) Osteoblast-specific transcription factor 2 | Q13950 | 0.564 | 3.56e−06 | 4.58e−05 |
| 54) Proteinase-3 | P24158 | −0.564 | 3.56e−06 | 4.58e−05 |
| 55) MASP3 | P48740 | 0.564 | 3.56e−06 | 4.58e−05 |
| 56) HNRPQ | O60506 | −0.564 | 3.56e−06 | 4.58e−05 |
| 57) SAA | P02735 | −0.564 | 3.56e−06 | 4.58e−05 |
| 58) PLXC1 | O60486 | 0.564 | 3.56e−06 | 4.58e−05 |
| 59) Coagulation Factor IX | P00740 | −0.564 | 3.56e−06 | 4.58e−05 |
| 60) CAPG | P40121 | −0.564 | 3.56e−06 | 4.58e−05 |

*Swiss Prot is a large protein sequence database widely used for protein resources

TABLE 5

Unpaired analysis of proteins showing differential expression between baseline and week 8 in n = 39 TB patients.

| | Target | Swiss Prot[a] | KS-distance (Signed) | p-value | q-value |
|---|---|---|---|---|---|
| 1) | TSP4 | P35443 | 0.821 | 1.37e−12 | 1.06e−09 |
| 2) | SEPR | Q12884 | 0.769 | 4.08e−11 | 1.05e−08 |
| 3) | MRC2 | Q9UBG0 | 0.769 | 4.08e−11 | 1.05e−08 |
| 4) | Antithrombin III | P01008 | 0.744 | 2.05e−10 | 3.15e−08 |
| 5) | PCI | P05154 | 0.744 | 2.05e−10 | 3.15e−08 |
| 6) | LBP | P18428 | −0.718 | 9.73e−10 | 6.25e−08 |
| 7) | a2-HS-Glycoprotein | P02765 | 0.718 | 9.73e−10 | 6.25e−08 |
| 8) | NPS-PLA2 | P14555 | −0.718 | 9.73e−10 | 6.25e−08 |
| 9) | Haptoglobin, Mixed Type | P00738 | −0.718 | 9.73e−10 | 6.25e−08 |
| 10) | Kallistatin | P29622 | 0.718 | 9.73e−10 | 6.25e−08 |
| 11) | MMP-2 | P08253 | 0.718 | 9.73e−10 | 6.25e−08 |
| 12) | NCAM-L1 | P32004 | 0.718 | 9.73e−10 | 6.25e−08 |
| 13) | CDON | Q4KMG0 | 0.692 | 4.38e−09 | 2.60e−07 |
| 14) | Fibronectin | P02751 | 0.667 | 1.87e−08 | 1.03e−06 |
| 15) | Cathepsin G | P08311 | −0.641 | 7.53e−08 | 2.23e−06 |
| 16) | gp130, soluble | P40189 | 0.641 | 7.53e−08 | 2.23e−06 |
| 17) | Nectin-like protein 2 | Q9BY67 | 0.641 | 7.53e−08 | 2.23e−06 |
| 18) | LEAP-1 | P81172 | −0.641 | 7.53e−08 | 2.23e−06 |
| 19) | CRP | P02741 | −0.641 | 7.53e−08 | 2.23e−06 |
| 20) | Fibrinogen g-chain dimer | P02679 | −0.641 | 7.53e−08 | 2.23e−06 |
| 21) | TIMP-2 | P16035 | 0.641 | 7.53e−08 | 2.23e−06 |
| 22) | IL-19 | Q9UHD0 | 0.641 | 7.53e−08 | 2.23e−06 |
| 23) | CDK8/cyclin C | P49336, P24863 | −0.641 | 7.53e−08 | 2.23e−06 |
| 24) | CHL1 | O00533 | 0.641 | 7.53e−08 | 2.23e−06 |
| 25) | D-dimer | P02671, P02675, P02679 | −0.641 | 7.53e−08 | 2.23e−06 |
| 26) | CATZ | Q9UBR2 | 0.641 | 7.53e−08 | 2.23e−06 |
| 27) | TrkC | Q16288 | 0.615 | 2.88e−07 | 7.15e−06 |
| 28) | Fibrinogen | P02671, P02675, P02679 | −0.615 | 2.88e−07 | 7.15e−06 |
| 29) | Angiopoietin-1 | Q15389 | −0.615 | 2.88e−07 | 7.15e−06 |
| 30) | Lipocalin 2 | P80188 | −0.615 | 2.88e−07 | 7.15e−06 |
| 31) | C9 | P02748 | −0.615 | 2.88e−07 | 7.15e−06 |
| 32) | MMP-9 | P14780 | −0.590 | 1.04e−06 | 1.82e−05 |
| 33) | I-TAC | O14625 | −0.590 | 1.04e−06 | 1.82e−05 |
| 34) | BMP-1 | P13497 | 0.590 | 1.04e−06 | 1.82e−05 |
| 35) | BMPER | Q8N8U9 | 0.590 | 1.04e−06 | 1.82e−05 |
| 36) | Plasminogen | P00747 | 0.590 | 1.04e−06 | 1.82e−05 |
| 37) | PHI | P06744 | −0.590 | 1.04e−06 | 1.82e−05 |
| 38) | TrkB | Q16620 | 0.590 | 1.04e−06 | 1.82e−05 |
| 39) | Coagulation Factor IX | P00740 | −0.590 | 1.04e−06 | 1.82e−05 |
| 40) | GOT1 | P17174 | −0.590 | 1.04e−06 | 1.82e−05 |
| 41) | RBP | P02753 | 0.590 | 1.04e−06 | 1.82e−05 |
| 42) | Albumin | P02768 | 0.590 | 1.04e−06 | 1.82e−05 |
| 43) | Sphingosine kinase 1 | Q9NYA1 | −0.590 | 1.04e−06 | 1.82e−05 |
| 44) | Afamin | P43652 | 0.590 | 1.04e−06 | 1.82e−05 |
| 45) | TIMP-1 | P01033 | −0.564 | 3.56e−06 | 4.58e−05 |
| 46) | GFRa-2 | O00451 | 0.564 | 3.56e−06 | 4.58e−05 |
| 47) | Azurocidin | P20160 | −0.564 | 3.56e−06 | 4.58e−05 |
| 48) | Lactoferrin | P02788 | −0.564 | 3.56e−06 | 4.58e−05 |
| 49) | amyloid precursor protein | P05067 | −0.564 | 3.56e−06 | 4.58e−05 |
| 50) | RET | P07949 | 0.564 | 3.56e−06 | 4.58e−05 |
| 51) | LRIG3 | Q6UXM1 | 0.564 | 3.56e−06 | 4.58e−05 |
| 52) | CD30 Ligand | P32971 | 0.564 | 3.56e−06 | 4.58e−05 |
| 53) | Osteoblast-specific transcription factor 2 | Q13950 | 0.564 | 3.56e−06 | 4.58e−05 |
| 54) | Proteinase-3 | P24158 | −0.564 | 3.56e−06 | 4.58e−05 |
| 55) | MASP3 | P48740 | 0.564 | 3.56e−06 | 4.58e−05 |
| 56) | HNRPQ | O60506 | −0.564 | 3.56e−06 | 4.58e−05 |
| 57) | SAA | P02735 | −0.564 | 3.56e−06 | 4.58e−05 |
| 58) | PLXC1 | O60486 | 0.564 | 3.56e−06 | 4.58e−05 |
| 59) | Coagulation Factor IX | P00740 | −0.564 | 3.56e−06 | 4.58e−05 |
| 60) | CAPG | P40121 | −0.564 | 3.56e−06 | 4.58e−05 |
| 61) | HSP 90a | P07900 | −0.538 | 1.15e−05 | 1.27e−04 |
| 62) | TNF sR-I | P19438 | −0.538 | 1.15e−05 | 1.27e−04 |
| 63) | Angiostatin | P00747 | 0.538 | 1.15e−05 | 1.27e−04 |
| 64) | Gelsolin | P06396 | 0.538 | 1.15e−05 | 1.27e−04 |
| 65) | MAPK14 | Q16539 | −0.538 | 1.15e−05 | 1.27e−04 |
| 66) | PBEF | P43490 | −0.538 | 1.15e−05 | 1.27e−04 |
| 67) | Contactin-4 | Q8IWV2 | 0.538 | 1.15e−05 | 1.27e−04 |
| 68) | IGFBP-7 | Q16270 | 0.538 | 1.15e−05 | 1.27e−04 |
| 69) | PGRP-S | O75594 | −0.538 | 1.15e−05 | 1.27e−04 |
| 70) | FN1.3 | P02751 | 0.538 | 1.15e−05 | 1.27e−04 |
| 71) | Myeloperoxidase | P05164 | −0.513 | 3.54e−05 | 2.94e−04 |

TABLE 5-continued

Unpaired analysis of proteins showing differential expression between baseline and week 8 in n = 39 TB patients.

| | Target | Swiss Prot[a] | KS-distance (Signed) | p-value | q-value |
|---|---|---|---|---|---|
| 72) | ROR1 | Q01973 | 0.513 | 3.54e−05 | 2.94e−04 |
| 73) | Cadherin-5 | P33151 | 0.513 | 3.54e−05 | 2.94e−04 |
| 74) | Carbonic anhydrase 6 | P23280 | 0.513 | 3.54e−05 | 2.94e−04 |
| 75) | FETUB | Q9UGM5 | 0.513 | 3.54e−05 | 2.94e−04 |
| 76) | FN1.4 | P02751 | 0.513 | 3.54e−05 | 2.94e−04 |
| 77) | DKK3 | Q9UBP4 | 0.513 | 3.54e−05 | 2.94e−04 |
| 78) | BPI | P17213 | −0.513 | 3.54e−05 | 2.94e−04 |
| 79) | Factor B | P00751 | −0.513 | 3.54e−05 | 2.94e−04 |
| 80) | Lysozyme | P61626 | −0.513 | 3.54e−05 | 2.94e−04 |
| 81) | bFGF-R | P11362 | 0.513 | 3.54e−05 | 2.94e−04 |
| 82) | Protein S | P07225 | −0.513 | 3.54e−05 | 2.94e−04 |
| 83) | Apo A-I | P02647 | 0.513 | 3.54e−05 | 2.94e−04 |
| 84) | MPIF-1 | P55773 | −0.513 | 3.54e−05 | 2.94e−04 |
| 85) | GDF-9 | O60383 | −0.513 | 3.54e−05 | 2.94e−04 |
| 86) | BGH3 | Q15582 | 0.513 | 3.54e−05 | 2.94e−04 |
| 87) | α1-Antitrypsin | P01009 | −0.513 | 3.54e−05 | 2.94e−04 |
| 88) | CYTD | P28325 | 0.513 | 3.54e−05 | 2.94e−04 |
| 89) | RACK1 | P63244 | 0.513 | 3.54e−05 | 2.94e−04 |
| 90) | C6 | P13671 | −0.513 | 3.54e−05 | 2.94e−04 |
| 91) | 14-3-3 eta | Q04917 | −0.513 | 3.54e−05 | 2.94e−04 |
| 92) | ITI heavy chain H4 | Q14624 | −0.513 | 3.54e−05 | 2.94e−04 |
| 93) | HRG | P04196 | 0.513 | 3.54e−05 | 2.94e−04 |
| 94) | SDF-1a | P48061 | 0.487 | 1.03e−04 | 6.84e−04 |
| 95) | SAP | P02743 | −0.487 | 1.03e−04 | 6.84e−04 |
| 96) | Thyroxine-Binding Globulin | P05543 | 0.487 | 1.03e−04 | 6.84e−04 |
| 97) | NAP-2 | P02775 | −0.487 | 1.03e−04 | 6.84e−04 |
| 98) | contactin-1 | Q12860 | 0.487 | 1.03e−04 | 6.84e−04 |
| 99) | TIG2 | Q99969 | −0.487 | 1.03e−04 | 6.84e−04 |
| 100) | CATC | P53634 | −0.487 | 1.03e−04 | 6.84e−04 |
| 101) | C2 | P06681 | −0.487 | 1.03e−04 | 6.84e−04 |
| 102) | CD109 | Q6YHK3 | 0.487 | 1.03e−04 | 6.84e−04 |
| 103) | Thrombin | P00734 | −0.487 | 1.03e−04 | 6.84e−04 |
| 104) | 14-3-3 protein gamma | P61981 | −0.487 | 1.03e−04 | 6.84e−04 |
| 105) | C3b | P01024 | −0.487 | 1.03e−04 | 6.84e−04 |
| 106) | CTAP-III | P02775 | −0.487 | 1.03e−04 | 6.84e−04 |
| 107) | C3d | P01024 | −0.487 | 1.03e−04 | 6.84e−04 |
| 108) | HGF | P14210 | −0.487 | 1.03e−04 | 6.84e−04 |
| 109) | Alkaline phosphatase, bone | P05186 | −0.487 | 1.03e−04 | 6.84e−04 |
| 110) | HAI-1 | O43278 | 0.487 | 1.03e−04 | 6.84e−04 |
| 111) | PAI-1 | P05121 | −0.487 | 1.03e−04 | 6.84e−04 |
| 112) | IP-10 | P02778 | −0.487 | 1.03e−04 | 6.84e−04 |
| 113) | AK1A1 | P14550 | −0.487 | 1.03e−04 | 6.84e−04 |
| 114) | ZAP70 | P43403 | −0.487 | 1.03e−04 | 6.84e−04 |
| 115) | VEGF121 | P15692 | −0.487 | 1.03e−04 | 6.84e−04 |
| 116) | Sonic Hedgehog | Q15465 | 0.487 | 1.03e−04 | 6.84e−04 |

TABLE 6

Disease severity score calculation

| Parameter | Range (min-max) | Normalization factor | Normalized Range (min-max) | Weigh factor | Scoring |
|---|---|---|---|---|---|
| CXRCLASS | 1-3 | 1 | 1-3 | 1 | added |
| CXREXTNT | A-C (1-3) | 1 | 1-3 | 1 | added |
| dtd_base | 3.67-17.5 | 0.2 | 0.734-3.5 | 1 | subtracted |
| smearb | 2-4 | 1 | 2-4 | 1 | added |
| bmi | 15.2-26.7 | 0.25 | 3.8-6.675 | 2 | subtracted |
| anycav | 0-1 | 1 | 0-1 | 1 | added |
| bilatcav | 0-1 | 1 | 0-1 | 2 | added |
| bilatabn | 0-1 | 1 | 0-1 | 1 | added |

TABLE 7

Calculation of the disease severity score

| pid | CXR-CLASS | CXREX-TNT | dtd_base | smearb | anycav | bilatcav | bilatabn | bmi | Score |
|---|---|---|---|---|---|---|---|---|---|
| 1016 | 1 | 2 | 6.21 | 2 | 0 | 0 | 0 | 26.7 | 0.026 |
| 1029 | 1 | 1 | 17.5 | 3 | 0 | 0 | 0 | 19 | 0.125 |
| 1015 | 1 | 2 | 10.46 | 3 | 0 | 0 | 0 | 23.1 | 0.147 |

TABLE 7-continued

Calculation of the disease severity score

| pid | CXR-CLASS | CXREX-TNT | dtd_base | smearb | anycav | bilatcav | bilatabn | bmi | Score |
|---|---|---|---|---|---|---|---|---|---|
| 1039 | 1 | 1 | 5.67 | 3 | 0 | 0 | 0 | 19.3 | 0.264 |
| 1021 | 1 | 1 | 5.9 | 3 | 0 | 0 | 0 | 19.2 | 0.264 |
| 1020 | 2 | 2 | 8.38 | 2 | 1 | 0 | 0 | 21.1 | 0.298 |
| 1038 | 1 | 3 | 8.33 | 2 | 0 | 0 | 1 | 20.8 | 0.308 |
| 1026 | 1 | 2 | 5.96 | 3 | 0 | 0 | 0 | 19.7 | 0.310 |
| 1034 | 1 | 2 | 9.54 | 4 | 0 | 0 | 0 | 20 | 0.318 |
| 1009 | 1 | 3 | 4.21 | 4 | 0 | 0 | 1 | 26 | 0.322 |
| 1004 | 1 | 2 | 7.38 | 4 | 0 | 0 | 0 | 20.5 | 0.330 |
| 1033 | 1 | 2 | 6.71 | 4 | 0 | 0 | 0 | 20 | 0.354 |
| 1040 | 1 | 2 | 7.54 | 4 | 0 | 0 | 0 | 19.1 | 0.371 |
| 1023 | 2 | 2 | 7.29 | 4 | 1 | 0 | 0 | 21.6 | 0.421 |
| 1019 | 3 | 2 | 5.5 | 3 | 1 | 0 | 0 | 22.1 | 0.428 |
| 1011 | 1 | 3 | 5.33 | 4 | 0 | 0 | 1 | 21.6 | 0.446 |
| 1012 | 2 | 2 | 5.83 | 3 | 1 | 0 | 0 | 19 | 0.458 |
| 1010 | 1 | 3 | 7.63 | 3 | 0 | 0 | 1 | 18.2 | 0.461 |
| 1006 | 1 | 3 | 7.92 | 3 | 0 | 0 | 1 | 17.9 | 0.467 |
| 1024 | 2 | 2 | 7.25 | 3 | 1 | 0 | 0 | 17.3 | 0.494 |
| 1031 | 1 | 2 | 4.38 | 4 | 0 | 0 | 1 | 18.3 | 0.498 |
| 1032 | 2 | 2 | 5.63 | 3 | 1 | 0 | 1 | 18.8 | 0.530 |
| 1022 | 3 | 2 | 13.17 | 4 | 1 | 0 | 1 | 19.6 | 0.535 |
| 1037 | 1 | 3 | 5.71 | 4 | 0 | 0 | 1 | 18.5 | 0.538 |
| 1028 | 2 | 3 | 5.5 | 3 | 1 | 0 | 1 | 18.8 | 0.594 |
| 1030 | 3 | 2 | 4.29 | 4 | 1 | 0 | 0 | 19.1 | 0.600 |
| 1027 | 3 | 2 | 8.96 | 4 | 1 | 0 | 0 | 17.1 | 0.604 |
| 1017 | 2 | 2 | 3.67 | 4 | 1 | 0 | 0 | 17.1 | 0.607 |
| 1014 | 3 | 3 | 6.13 | 4 | 1 | 0 | 0 | 19.9 | 0.614 |
| 1001 | 3 | 2 | 4.42 | 4 | 1 | 0 | 0 | 18.1 | 0.629 |
| 1003 | 2 | 3 | 9.58 | 3 | 1 | 0 | 1 | 15.9 | 0.633 |
| 1036 | 3 | 2 | 4.67 | 4 | 1 | 0 | 1 | 17.9 | 0.695 |
| 1025 | 3 | 3 | 5.46 | 4 | 1 | 0 | 1 | 19.3 | 0.704 |
| 1005 | 2 | 3 | 5.38 | 4 | 1 | 0 | 1 | 16.9 | 0.717 |
| 1018 | 3 | 3 | 6.92 | 4 | 1 | 0 | 1 | 18 | 0.726 |
| 1002 | 3 | 3 | 5.25 | 4 | 1 | 0 | 1 | 16.6 | 0.791 |
| 1007 | 3 | 2 | 4.5 | 4 | 1 | 1 | 1 | 17.1 | 0.847 |
| 1008 | 3 | 3 | 5.67 | 4 | 1 | 1 | 1 | 17.4 | 0.885 |
| 1013 | 3 | 3 | 5.33 | 4 | 1 | 1 | 1 | 15.2 | 0.958 |
| min | 1 | 1 | 3.67 | 2 | 0 | 0 | 0 | 15.2 | |
| max | 3 | 3 | 17.5 | 4 | 1 | 1 | 1 | 26.7 | |
| a* | x 1 | x 1 | x 0.2 | x 1 | x 1 | x 1 | x 1 | c* | |
| b* | 1 | 1 | 1 | 1 | 1 | 2 | 2 | 2 | |

$^a$scale/normalize
$^b$weight factor
$^c$(bmi − 12)/4

TABLE 8

Biomarkers for overall TB treatment changes, without specific analysis*

| Protein | SwissProt | KS Distance | Empirical P-Value | Q-Value |
|---|---|---|---|---|
| MRC2 | Q9UBG0 | 0.8947 | 2.829e−011 | 7.859e−010 |
| TSP4 | P35443 | 0.8947 | 2.829e−011 | 7.859e−010 |
| gp130, soluble | P40189 | 0.8947 | 2.829e−011 | 7.859e−010 |
| SEPR | Q12884 | 0.8421 | 2.829e−011 | 7.859e−010 |
| CATZ | Q9UBR2 | 0.8421 | 2.829e−011 | 7.859e−010 |
| CDON | Q4KMG0 | 0.8421 | 2.829e−011 | 7.859e−010 |
| LEAP-1 | P81172 | 0.8421 | 2.829e−011 | 7.859e−010 |
| Antithrombin III | P01008 | 0.8421 | 2.829e−011 | 7.859e−010 |
| Nectin-like protein 2 | Q9BY67 | 0.8421 | 2.829e−011 | 7.859e−010 |
| LBP | P18428 | 0.8421 | 2.829e−011 | 7.859e−010 |
| CRP | P02741 | 0.7895 | 2.829e−011 | 7.859e−010 |
| NCAM-L1 | P32004 | 0.7895 | 2.829e−011 | 7.859e−010 |
| MMP-2 | P08253 | 0.7895 | 2.829e−011 | 7.859e−010 |
| Fibronectin | P02751 | 0.7895 | 2.829e−011 | 7.859e−010 |
| a2-HS-Glycoprotein | P02765 | 0.7895 | 2.829e−011 | 7.859e−010 |
| Osteoblast-specif transcr fact 2 | Q13950 | 0.7895 | 2.829e−011 | 7.859e−010 |
| Kallistatin | P29622 | 0.7895 | 2.829e−011 | 7.859e−010 |
| CD30 Ligand | P32971 | 0.7895 | 2.829e−011 | 7.859e−010 |
| PCI | P05154 | 0.7895 | 2.829e−011 | 7.859e−010 |
| BGH3 | Q15582 | 0.7895 | 2.829e−011 | 7.859e−010 |
| Haptoglobin, Mixed Type | P00738 | 0.7895 | 2.829e−011 | 7.859e−010 |
| TrkB | Q16620 | 0.7368 | 9.569e−006 | 0.0001861 |
| BMPER | Q8N8U9 | 0.7368 | 9.569e−006 | 0.0001861 |
| Contactin-4 | Q8IWV2 | 0.7368 | 9.569e−006 | 0.0001861 |
| NPS-PLA2 | P14555 | 0.7368 | 9.569e−006 | 0.0001861 |
| Coagulation Factor IX | P00740 | 0.7368 | 1.914e−005 | 0.0001861 |
| Afamin | P43652 | 0.7368 | 1.914e−005 | 0.0001861 |
| SAA | P02735 | 0.7368 | 1.914e−005 | 0.0001861 |
| LRIG3 | Q6UXM1 | 0.7368 | 1.914e−005 | 0.0001861 |
| RET | P07949 | 0.7368 | 1.914e−005 | 0.0001861 |
| I-TAC | O14625 | 0.7368 | 1.914e−005 | 0.0001861 |
| ROR1 | Q01973 | 0.7368 | 1.914e−005 | 0.0001861 |
| GFRa-2 | O00451 | 0.7368 | 1.914e−005 | 0.0001861 |
| Cathepsin G | P08311 | 0.7368 | 1.914e−005 | 0.0001861 |
| bFGF-R | P11362 | 0.7368 | 1.914e−005 | 0.0001861 |
| Fibrinogen g-chain dimer | P02679 | 0.6842 | 1.914e−005 | 0.0001861 |

TABLE 8-continued

Biomarkers for overall TB treatment changes, without specific analysis*

| Protein | SwissProt | KS Distance | Empirical P-Value | Q-Value |
|---|---|---|---|---|
| Lysozyme | P61626 | 0.6842 | 1.914e−005 | 0.0001861 |
| GOT1 | P17174 | 0.6842 | 1.914e−005 | 0.0001861 |
| D-dimer | P02671 | 0.6842 | 1.914e−005 | 0.0001861 |
| Coagulation Factor IX | P43652 | 0.6842 | 1.914e−005 | 0.0001861 |
| ITI heavy chain H4 | Q14624 | 0.6842 | 1.914e−005 | 0.0001861 |
| Gelsolin | P06396 | 0.6842 | 1.914e−005 | 0.0001861 |
| PHI | P06744 | 0.6842 | 1.914e−005 | 0.0001861 |
| HSP 70 | P08107 | 0.6842 | 1.914e−005 | 0.0001861 |
| Albumin | P02768 | 0.6842 | 1.914e−005 | 0.0001861 |
| MASP3 | P48740 | 0.6842 | 1.914e−005 | 0.0001861 |
| a1-Antitrypsin | P01009 | 0.6842 | 1.914e−005 | 0.0001861 |
| CDK8/cyclin C | P49336 | 0.6842 | 1.914e−005 | 0.0001861 |
| BMP-1 | P13497 | 0.6842 | 1.914e−005 | 0.0001861 |
| C9 | P02748 | 0.6842 | 1.914e−005 | 0.0001861 |
| IL-19 | Q9UHD0 | 0.6842 | 1.914e−005 | 0.0001861 |
| HAI-1 | O43278 | 0.6842 | 1.914e−005 | 0.0001861 |
| Protein S | P07225 | 0.6842 | 1.914e−005 | 0.0001861 |
| Myeloperoxidase | P05164 | 0.6842 | 1.914e−005 | 0.0001861 |
| TRAIL R1 | O00220 | 0.6842 | 1.914e−005 | 0.0001861 |
| DKK3 | Q9UBP4 | 0.6842 | 1.914e−005 | 0.0001861 |
| amyloid precursor protein | P05067 | 0.6842 | 1.914e−005 | 0.0001861 |
| Angiopoietin-1 | Q15389 | 0.6842 | 1.914e−005 | 0.0001861 |
| Fibrinogen | P02671, P02675 | 0.6842 | 1.914e−005 | 0.0001861 |
| MMP-9 | P14780 | 0.6842 | 1.914e−005 | 0.0001861 |
| MAPK14 | Q16539 | 0.6316 | 0.0005856 | 0.0028 |
| HRG | P04196 | 0.6316 | 0.0005856 | 0.0028 |
| CAPG | P40121 | 0.6316 | 0.0005856 | 0.0028 |
| PLXC1 | O60486 | 0.6316 | 0.0005856 | 0.0028 |
| PDGF-BB | P01127 | 0.6316 | 0.0005856 | 0.0028 |
| C6 | P13671 | 0.6316 | 0.0005856 | 0.0028 |
| BPI | P17213 | 0.6316 | 0.0005856 | 0.0028 |
| CYTD | P28325 | 0.6316 | 0.0005856 | 0.0028 |
| a2-Macroglobulin | P01023 | 0.6316 | 0.0005856 | 0.0028 |
| RBP | P02753 | 0.6316 | 0.0005856 | 0.0028 |
| CHL1 | O00533 | 0.6316 | 0.0005856 | 0.0028 |
| Proteinase-3 | P24158 | 0.6316 | 0.0005856 | 0.0028 |
| FETUB | Q9UGM5 | 0.6316 | 0.0005856 | 0.0028 |
| Carbonic anhydrase 6 | P23280 | 0.6316 | 0.0005856 | 0.0028 |
| RGMB | Q6NW40 | 0.6316 | 0.0005856 | 0.0028 |
| IGFBP-7 | Q16270 | 0.6316 | 0.0005856 | 0.0028 |
| CD23 | P06734 | 0.6316 | 0.0005856 | 0.0028 |
| CD109 | Q6YHK3 | 0.6316 | 0.0005856 | 0.0028 |
| TGF-b R III | Q03167 | 0.6316 | 0.0005856 | 0.0028 |
| NAP-2 | P02775 | 0.6316 | 0.0005856 | 0.0028 |
| Lipocalin 2 | P80188 | 0.6316 | 0.0005856 | 0.0028 |
| Cadherin-5 | P33151 | 0.6316 | 0.0005856 | 0.0028 |
| Azurocidin | P20160 | 0.6316 | 0.0005856 | 0.0028 |
| Apo A-I | P02647 | 0.6316 | 0.0005856 | 0.0028 |
| CNTFR alpha | P26992 | 0.6316 | 0.0005856 | 0.0028 |
| Thyroxine-Binding Globulin | P05543 | 0.6316 | 0.0005856 | 0.0028 |
| HGF | P14210 | 0.6316 | 0.0005856 | 0.0028 |
| TrkC | Q16288 | 0.6316 | 0.0005856 | 0.0028 |
| SDF-1a | P48061 | 0.6316 | 0.0005856 | 0.0028 |
| TIMP-2 | P16035 | 0.6316 | 0.0005856 | 0.0028 |
| TSG-6 | P98066 | 0.5789 | 0.0005856 | 0.0028 |
| JAK2 | O60674 | 0.5789 | 0.0005856 | 0.0028 |
| C3d | P01024 | 0.5789 | 0.0005856 | 0.0028 |
| 14-3-3 eta | P63104 | 0.5789 | 0.0005856 | 0.0028 |
| CTAP-III | P02775 | 0.5789 | 0.0005856 | 0.0028 |
| BOC | Q9BWV1 | 0.5789 | 0.0005856 | 0.0028 |
| HNRPQ | O60506 | 0.5789 | 0.0005856 | 0.0028 |
| PSA-ACT | P07288 | 0.5789 | 0.0005856 | 0.0028 |
| Plasminogen | P00747 | 0.5789 | 0.0005856 | 0.0028 |
| IP-10 | P02778 | 0.5789 | 0.0005856 | 0.0028 |
| BASI | P35613 | 0.5789 | 0.0005856 | 0.0028 |
| FN1.4 | P02751 | 0.5789 | 0.0005856 | 0.0028 |
| FN1.3 | P02751 | 0.5789 | 0.0005856 | 0.0028 |
| PGRP-S | O75594 | 0.5789 | 0.0005856 | 0.0028 |
| Contactin-5 | O94779 | 0.5789 | 0.0005856 | 0.0028 |
| C2 | P06681 | 0.5789 | 0.0005856 | 0.0028 |
| IDUA | P35475 | 0.5789 | 0.0005856 | 0.0028 |
| TIG2 | Q99969 | 0.5789 | 0.0005856 | 0.0028 |
| GDF-9 | O60383 | 0.5789 | 0.0005856 | 0.0028 |
| LSAMP | Q13449 | 0.5789 | 0.0005856 | 0.0028 |
| NG36 | Q96KQ7 | 0.5789 | 0.0005856 | 0.0028 |
| PAI-1 | P05121 | 0.5789 | 0.0005856 | 0.0028 |
| MPIF-1 | P55773 | 0.5789 | 0.0005856 | 0.0028 |
| Lactoferrin | P02788 | 0.5789 | 0.0005856 | 0.0028 |
| Sonic Hedgehog | Q15465 | 0.5789 | 0.0005856 | 0.0028 |
| MIA | Q16674 | 0.5789 | 0.0005856 | 0.0028 |
| IGFBP-6 | P24592 | 0.5789 | 0.0005856 | 0.0028 |
| IGFBP-5 | P24593 | 0.5789 | 0.0005856 | 0.0028 |
| HSP 90a | P07900 | 0.5789 | 0.0005856 | 0.0028 |
| SCF sR | P07900 | 0.5789 | 0.0005856 | 0.0028 |
| SAP | P02743 | 0.5789 | 0.0005856 | 0.0028 |
| TIMP-1 | P01033 | 0.5789 | 0.0005856 | 0.0028 |
| Sphingosine kinase | Q9NYA1 | 0.5789 | 0.0005856 | 0.0028 |

*Based upon 8-week treatment response

TABLE 9

Top candidate biomarkers for predicting treatment response at 8 weeks*

| Analysis | Protein | SwissProt | Signed KS | p-value | q-value |
|---|---|---|---|---|---|
| Baseline | PSME1 | Q06323 | 0.639 | 0.000307 | 0.29 |
| | IL-11 RA | Q14626 | −0.597 | 0.00094 | 0.29 |
| | HSP 70 | P11142 | 0.589 | 0.00115 | 0.29 |
| | Galectin-8 | O00214 | −0.584 | 0.00131 | 0.29 |
| | a2-Antiplasmin | P08697 | 0.582 | 0.0014 | 0.29 |
| | IFN-lambda 2 | Q8IZJ0 | 0.545 | 0.00342 | 0.60 |
| | MMP-13 | P45452 | −0.532 | 0.00463 | 0.64 |
| | iC3b | P01024 | −0.529 | 0.00492 | 0.64 |
| | APRIL | O75888 | −0.495 | 0.0104 | 0.99 |
| | MMP-12 | P39900 | 0.495 | 0.0104 | 0.99 |
| Week 8 | Coagulation Factor V | P12259 | 0.645 | 0.000266 | 0.28 |
| | XPNPEP1 | Q9NQW7 | 0.589 | 0.00115 | 0.60 |
| | gp130, soluble | P40189 | 0.547 | 0.00321 | 0.80 |
| | BGH3 | Q15582 | 0.539 | 0.00386 | 0.80 |
| | TIMP-2 | P16035 | 0.532 | 0.00463 | 0.80 |
| | APRIL | O75888 | −0.500 | 0.00932 | 0.80 |
| | ECM1 | Q16610 | 0.500 | 0.00932 | 0.80 |
| | IFN-aA | P01563 | 0.495 | 0.0104 | 0.80 |
| | Vasoactive Intestinal Peptide | P01282 | 0.495 | 0.0104 | 0.80 |
| | IL-11 | P20809 | 0.492 | 0.011 | 0.80 |
| Log2 ratio of baseline-to-wk8 | | | | | |
| | EphA1 | P21709 | −0.550 | 0.00302 | 0.85 |
| | gp130, soluble | P40189 | −0.547 | 0.00321 | 0.85 |
| | TIMP-1 | P01033 | 0.537 | 0.0041 | 0.85 |
| | MMP-8 | P22894 | 0.534 | 0.00436 | 0.85 |
| | AMPM2 | P50579 | 0.532 | 0.00463 | 0.85 |
| | MMP-12 | P39900 | 0.492 | 0.011 | 0.85 |
| | Macrophage scavenger receptor | P21757 | 0.487 | 0.0123 | 0.85 |
| | Nectin-like protein 2 | Q9BY67 | −0.487 | 0.0123 | 0.85 |

TABLE 9-continued

Top candidate biomarkers for predicting treatment response at 8 weeks*

| Analysis | Protein | SwissProt | Signed KS | p-value | q-value |
|---|---|---|---|---|---|
| | CNDP1 | Q96KN2 | −0.487 | 0.0123 | 0.85 |
| | DKK3 | Q9UBP4 | −0.487 | 0.0123 | 0.85 |

*Ranked according to KS score. For the analyses at baseline and at 8 weeks, positive KS values indicate higher protein levels in responders than slow-responders. For the analysis using the Log2 ratio of baseline-to-wk8 signals, positive KS values indicate a larger differential change between the two time points in the responders compared to slow-responders.

TABLE 10

Top candidate biomarkers for predicting treatment response at 8 weeks*

| Rank | Protein | SwissProt | Rank Sum Z score | p-value | q-value |
|---|---|---|---|---|---|
| 1 | Nectin-like protein 1 | Q9BY67 | 3.301 | 0.00096 | 0.37 |
| 2 | EphA1 | P21709 | 3.077 | 0.0021 | 0.65 |
| 3 | gp130, soluble | P40189 | 2.852 | 0.0044 | 0.65 |
| 4 | CATZ | Q9UBR2 | 2.768 | 0.0057 | 0.65 |
| 5 | CNDP1 | Q96KN2 | 2.627 | 0.0086 | 0.65 |
| 6 | TGF-β R III | Q03167 | 2.599 | 0.0094 | 0.65 |
| 7 | MRC2 | Q9UBG0 | 2.515 | 0.012 | 0.65 |
| 8 | ADAM 9 | Q13443 | 2.459 | 0.014 | 0.76 |
| 9 | CDON | Q4KMG0 | 2.459 | 0.014 | 0.76 |
| 10 | IL-2 sRα | P01589 | −2.430 | 0.015 | 0.76 |

*Ranked according to their Rank Sum Z-score. Positive rank sum values indicate a larger differential change between the two time points in the responders compared to slow-responders.

TABLE 11

Additional TB treatment response markers*

| Protein | SwissProt |
|---|---|
| BGN | P21810 |
| IL-7 | P13232 |
| LYNB | P07948 |
| YES | P07947 |

*Identified by comparison of week-8 responders to slow-responders vs. week 8 slow-responders to all baseline

TABLE 12

Top 10 proteins at baseline and at 8 weeks that correlate with TTCC in univariate regression of log10 RFU on TTCC (measured in weeks), ranked by $R^2$

| Analysis | Protein | SwissProt | Slope* | $R^2$ | p-value | q-value |
|---|---|---|---|---|---|---|
| Baseline | | | | | | |
| | ERP29 | P30040 | −0.012 | 0.30 | 0.00037 | 0.39 |
| | Peroxiredoxin-5 | P30044 | −0.0078 | 0.24 | 0.0018 | 0.69 |
| | HSP 70 | P08107 | −0.016 | 0.23 | 0.002 | 0.69 |
| | α2-Antiplasmin | P08697 | −0.0058 | 0.21 | 0.0035 | 0.90 |
| | RANTES | P13501 | 0.0059 | 0.19 | 0.0051 | 1.00 |
| | IgG | P01857 | 0.0063 | 0.19 | 0.0091 | 1.00 |
| | Transketolase | P29401 | −0.01 | 0.17 | 0.0095 | 1.00 |
| | NKG2D (KLRK1) | P26718 | 0.0041 | 0.17 | 0.0096 | 1.00 |
| | Coagulation Factor V | P12259 | −0.0089 | 0.16 | 0.012 | 1.00 |
| | Coagulation Factor IX | P00740 | −0.0056 | 0.15 | 0.014 | 1.00 |
| 8 weeks | | | | | | |
| | NKG2D (KLRK1) | P26718 | 0.0043 | 0.26 | 0.00081 | 0.65 |
| | XPNPEP1 | Q9NQW7 | −0.0024 | 0.32 | 0.0012 | 0.65 |
| | BGH3 (TGFBI) | Q15582 | −0.0085 | 0.22 | 0.0026 | 0.71 |
| | CDK8/cyclin C | P49336 | 0.0041 | 0.23 | 0.0027 | 0.71 |
| | SAA | P02735 | 0.076 | 0.19 | 0.0051 | 0.83 |
| | Coagulation Factor V | P12259 | −0.0069 | 0.19 | 0.0053 | 0.83 |
| | YES | P07947 | −0.0038 | 0.19 | 0.0059 | 0.83 |
| | PARC | P55774 | 0.019 | 0.17 | 0.0095 | 0.83 |
| | CD39 | P49961 | 0.0031 | 0.17 | 0.011 | 0.83 |
| | LRIG3 | Q6UXM1 | −0.0055 | 0.16 | 0.011 | 0.83 |

*Linear model coefficient gives change in log RFU signal per week

The invention claimed is:

1. A kit for identifying the tuberculosis (TB) status of an individual, the kit comprising four aptamers for detecting the level of the protein biomarkers kallistatin, Complement component 9, afamin, and TSP4 in a sample from an individual;
 wherein the TB status of the individual is TB-positive or TB-negative; and
 wherein, each aptamer has specific affinity for a different protein of the protein biomarkers.

2. The kit of claim 1, wherein the aptamers are capable of binding a solid support or are bound to a solid support.

3. The kit of claim 1 further comprising a solid support.

4. The kit of claim 1 further comprising a labeling agent, wherein the labeling agent labels the aptamers.

* * * * *